(12) United States Patent
Abate et al.

(10) Patent No.: US 10,434,507 B2
(45) Date of Patent: Oct. 8, 2019

(54) HIGH DEFINITION MICRODROPLET PRINTER

(71) Applicant: The Regents of the University of California, Oakland, CA (US)

(72) Inventors: Adam R. Abate, San Francisco, CA (US); Adam R. Sciambi, San Francisco, CA (US); Russell Cole, San Francisco, CA (US); Zev Jordan Gartner, Pacifica, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/520,056

(22) PCT Filed: Oct. 21, 2015

(86) PCT No.: PCT/US2015/056743
§ 371 (c)(1),
(2) Date: Apr. 18, 2017

(87) PCT Pub. No.: WO2016/065056
PCT Pub. Date: Apr. 28, 2016

(65) Prior Publication Data
US 2018/0056288 A1    Mar. 1, 2018

Related U.S. Application Data

(60) Provisional application No. 62/067,314, filed on Oct. 22, 2014, provisional application No. 62/112,068, filed on Feb. 4, 2015.

(51) Int. Cl.
*B01L 3/02* (2006.01)
*G01N 15/14* (2006.01)
(Continued)

(52) U.S. Cl.
CPC ....... *B01L 3/0268* (2013.01); *B01L 3/502784* (2013.01); *G01N 15/1459* (2013.01);
(Continued)

(58) Field of Classification Search
CPC ............. B01L 3/0268; B01L 3/502784; G01N 15/1459
See application file for complete search history.

(56) References Cited

U.S. PATENT DOCUMENTS 7,638,276 B2    12/2009   Griffiths et al.
RE41,780 E       9/2010   Anderson et al.
(Continued)

FOREIGN PATENT DOCUMENTS

AU    2013203624    5/2013
DE      10339452    3/2005
(Continued)

OTHER PUBLICATIONS

Wheeler et al, Digital Microfluidics with In-Line Sample Purification for Proteomics Analyses with MALDI-MS, Anal. Chem. 2005, 77, 534-540. (Year: 2005).*
(Continued)

*Primary Examiner* — Narayan K Bhat
(74) *Attorney, Agent, or Firm* — Michael B. Rubin; Bozicevic, Field & Francis LLP

(57) ABSTRACT

Methods for delivering discrete entities including, e.g., cells, media or reagents to substrates are provided. In certain aspects, the methods include manipulating and/or analyzing qualities of the entities or biological components thereof. In some embodiments, the methods may be used to create arrays of microenvironments and/or for two and three-dimensional printing of tissues or structures. Systems and devices for practicing the subject methods are also provided.

27 Claims, 12 Drawing Sheets

(51) Int. Cl.
 *B01L 3/00* (2006.01)
 *G01N 15/10* (2006.01)
 *G01N 35/10* (2006.01)

(52) U.S. Cl.
 CPC .. *G01N 15/1484* (2013.01); *B01L 2200/0673* (2013.01); *B01L 2300/0645* (2013.01); *B01L 2300/0829* (2013.01); *B01L 2300/0864* (2013.01); *B01L 2400/0427* (2013.01); *B01L 2400/086* (2013.01); *G01N 15/1463* (2013.01); *G01N 2015/1006* (2013.01); *G01N 2015/149* (2013.01); *G01N 2035/1034* (2013.01)

(56) References Cited

U.S. PATENT DOCUMENTS

| | | |
|---|---|---|
| 8,067,159 B2 | 11/2011 | Brown et al. |
| 8,257,925 B2 | 9/2012 | Brown et al. |
| 8,765,485 B2 | 7/2014 | Link et al. |
| 9,150,852 B2 | 10/2015 | Samuels et al. |
| 2003/0156993 A1 | 8/2003 | Staats |
| 2005/0019902 A1 | 1/2005 | Mathies et al. |
| 2005/0112639 A1 | 5/2005 | Wang et al. |
| 2007/0039866 A1* | 2/2007 | Schroeder ........ G01N 27/44769 210/265 |
| 2007/0077572 A1 | 4/2007 | Tawfik et al. |
| 2007/0141593 A1 | 6/2007 | Lee et al. |
| 2007/0231880 A1 | 10/2007 | Chang-Yen et al. |
| 2008/0014589 A1 | 1/2008 | Link et al. |
| 2009/0045064 A1 | 2/2009 | Simmons et al. |
| 2009/0098555 A1 | 4/2009 | Roth et al. |
| 2010/0015614 A1* | 1/2010 | Beer ................. B01L 3/502792 435/6.12 |
| 2010/0028915 A1 | 2/2010 | Gualberto et al. |
| 2010/0055677 A1 | 3/2010 | Colston, Jr. et al. |
| 2010/0173394 A1 | 7/2010 | Colston, Jr. et al. |
| 2010/0285975 A1 | 11/2010 | Mathies et al. |
| 2011/0053798 A1 | 3/2011 | Hindson et al. |
| 2011/0056575 A1 | 3/2011 | Hong et al. |
| 2011/0059556 A1 | 3/2011 | Strey et al. |
| 2011/0103176 A1 | 5/2011 | Van Dam et al. |
| 2011/0104816 A1 | 5/2011 | Pollack et al. |
| 2011/0118151 A1 | 5/2011 | Eshoo et al. |
| 2011/0160078 A1 | 6/2011 | Fodor et al. |
| 2011/0217736 A1 | 9/2011 | Hindson |
| 2011/0311978 A1 | 12/2011 | Makarewicz et al. |
| 2012/0010086 A1 | 1/2012 | Froehlich et al. |
| 2012/0045765 A1 | 2/2012 | Curran et al. |
| 2012/0122714 A1 | 5/2012 | Samuels et al. |
| 2012/0309002 A1 | 6/2012 | Link |
| 2012/0190032 A1 | 7/2012 | Ness et al. |
| 2012/0190033 A1 | 7/2012 | Ness et al. |
| 2012/0196288 A1 | 8/2012 | Beer |
| 2012/0219947 A1 | 8/2012 | Yurkovetsky et al. |
| 2012/0220494 A1 | 8/2012 | Samuels et al. |
| 2012/0258870 A1 | 10/2012 | Schwartz et al. |
| 2012/0264646 A1 | 10/2012 | Link et al. |
| 2012/0316074 A1 | 12/2012 | Saxonov et al. |
| 2013/0032235 A1 | 2/2013 | Johnstone et al. |
| 2013/0084572 A1 | 4/2013 | Hindson et al. |
| 2013/0095469 A1 | 4/2013 | Koltay et al. |
| 2013/0116130 A1 | 5/2013 | Fu et al. |
| 2013/0130919 A1 | 5/2013 | Chen et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0236901 A1 | 9/2013 | Potier et al. |
| 2014/0057799 A1 | 2/2014 | Johnson et al. |
| 2014/0154695 A1 | 6/2014 | Raindance |
| 2014/0155295 A1 | 6/2014 | Hindson et al. |
| 2014/0179544 A1 | 6/2014 | Steenblock et al. |
| 2014/0199731 A1 | 7/2014 | Agresti et al. |
| 2014/0272988 A1 | 9/2014 | Zador et al. |
| 2014/0323316 A1 | 10/2014 | Drmanac et al. |
| 2014/0378349 A1 | 12/2014 | Hindson et al. |
| 2015/0232942 A1 | 5/2015 | Abate et al. |
| 2015/0298091 A1 | 10/2015 | Weitz et al. |
| 2016/0177375 A1 | 6/2016 | Abate et al. |
| 2017/0009274 A1 | 1/2017 | Abate et al. |
| 2017/0022538 A1 | 1/2017 | Abate et al. |
| 2017/0121756 A1 | 5/2017 | Abate et al. |

FOREIGN PATENT DOCUMENTS

| | | |
|---|---|---|
| EP | 1547677 | 6/2005 |
| EP | 2145955 | 2/2012 |
| WO | WO 1994012216 | 6/1994 |
| WO | 2007140015 | 12/2007 |
| WO | 2009050512 | 4/2009 |
| WO | WO 2009054870 | 4/2009 |
| WO | WO 2009111014 | 9/2009 |
| WO | 2010148039 | 12/2010 |
| WO | 2011047307 | 4/2011 |
| WO | WO 2012011091 | 1/2012 |
| WO | WO 2012/048341 * | 4/2012 |
| WO | WO 2012162267 | 5/2012 |
| WO | WO 2012083225 | 6/2012 |
| WO | 2012109600 | 8/2012 |
| WO | WO 2012142213 | 10/2012 |
| WO | 2013119753 | 8/2013 |
| WO | WO 2013126741 | 8/2013 |
| WO | WO 2013130512 | 9/2013 |
| WO | WO 2013134261 | 9/2013 |
| WO | WO 2013173394 | 11/2013 |
| WO | WO 2014028378 | 2/2014 |
| WO | WO 2014028537 | 2/2014 |
| WO | WO 2014047556 | 3/2014 |
| WO | WO 2014083435 | 6/2014 |
| WO | WO 2014093676 | 6/2014 |
| WO | 2014108323 | 7/2014 |
| WO | 2014153071 | 9/2014 |
| WO | WO 2014138132 | 9/2014 |
| WO | WO 2014151658 | 9/2014 |
| WO | WO 2015120398 | 2/2015 |
| WO | 2015031691 | 3/2015 |
| WO | WO 2015200717 | 6/2015 |
| WO | 2015157369 | 10/2015 |
| WO | WO 2016064755 | 4/2016 |
| WO | WO 2016126865 | 8/2016 |
| WO | WO 2016126871 | 8/2016 |

OTHER PUBLICATIONS

Grover, et al. (2009) "Multiple displacement amplification as a pre-polymerase chain reaction (pre-PCR) to detect ultra low population of Ralstonia solanacearum (Smith 1896) Yabuchi et al. (1996)"; Lett Appl Microbiol. 49(5); pp. 539-543.

Kawasaki (1990) "Sample Preparation From Blood, Cells, and Other Fluids"; Chapter 18; pp. 146-152 in PCR protocols: A guide to methods and Applications, edited by Michael A. Innis, David H. Gelfand, John J. Sninsky, Thomas J. White.

Nunes et al. (2013) "Dripping and jetting in microfluidic multiphase flows applied to particle and fiber synthesis"; J Phys D Appl Phys. 46(11); pii: 114002.

Sidore, et al (2016) "Enhanced sequencing coverage with digital droplet multiple displacement amplification"; Nucleic. Acids Res. 44(7):e66.; pp. 1-9.

Tamminen, et al (2015) "Single gene-based distinction of individual microbial genomes from a mixed population of microbial cells"; Front Microbiol. 6:195; pp. 1-10.

Yu, et al (2014) "Mung bean nuclease treatment increases capture specificity of microdroplet-PCR based targeted DNA enrichment"; PLoS One 9(7):e103491; pp. 1-7.

U.S. Appl. No. 15/753,132, filed Feb. 15, 2018, Abate, Adam et al.
U.S. Appl. No. 15/940,850, filed Mar. 29, 2018, Abate, Adam et al.

Zhu Z, et al (2012) "Highly sensitive and quantitative detection of rare pathogens through agarose droplet microfluidic emulsion PCR at the single-cell lever"; Lab on a Chip 12(20); pp. 3907-3913.

Küster, et al (2013) "Interfacing droplet microfluidics with matrix-assisted laser desorption/ionization mass spectrometry: label-free content analysis of single droplets"; Anal Chem. 5;85(3); pp. 1285-1289.

(56) References Cited

OTHER PUBLICATIONS

Abate Adam. R, et al; (2010) "Microfluidic sorting with high-speed single-layer membrane valves"; *Applied Physics Letters* 96; pp. 203509-1-203509-3.
Abate Adam. R., et al; "High-throughput injection with microfluidics using picoinjectors"; *PNAS* vol. 107 1 No. 45; Nov. 9, 2010; pp. 19163-19166.
Abate AR, et al; (2011) "Efficient encapsulation with plug-triggered drop formation"; *Physical Review E.*;84(3):031502.
Abate AR and Weitz DA; (2011) "Faster multiple emulsification with drop splitting". *Lab on a Chip*;11(11); pp. 1911-1915.
Abate AR, et al; (2011) "One-step formation of multiple emulsions in microfluidics"; *Lab on a Chip*11(2); pp. 253-258.
Abate AR, et al; (2008) "Photoreactive coating for high-contrast spatial patterning of microfluidic device wettability"; *Lab on a Chip* 8(12); pp. 2157-2160.
Ali et al. "Rolling circle amplification: a versatile tool for chemical biology, materials science and medicine"; *Chem Soc Rev.* vol. 43; Mar. 18, 2014; pp. 3324-3341.
Agresti JJ, et al; "Ultrahigh-throughput screening in drop-based microfluidics for directed evolution"; *PNAS* vol. 107, No. 9; Mar. 2, 2010; pp. 4004-4009.
Agresti J. et al; (2010) "Correction for Ultrahigh-throughput screening in drop-based microfluidics for directed evolution"; *Proc. Nati Acad. Sci. USA*, 107; pp. 6550-6551.
Ahn K, et al; (2006) "Electrocoalescence of drops synchronized by size-dependent flow in microfluidic channels"; *Appl Phys Lett* 88; pp. 264105-1-264105-3.
Allen LZ, et al; (2011) "Single virus genomics: a new tool for virus discovery"; *PLoS One* 6(3):e17722.
Arriaga LR, et al. (2013) "Ultrathin Shell Double Emulsion Templated Giant Unilamellar Lipid Vesicles with Controlled Microdomain Formation"; *Small* 10(5); pp. 950-956.
Atten P; (1993) "Electrocoalescence of Water Droplets in an Insulating Liquid"; *J Electrostat* 30; pp. 259-269.
Barenholz Y, et al; (1977) "A simple method for the preparation of homogeneous phospholipid vesicles" *Biochemistry* 16(12); pp. 2806-2810.
Baret J-C, et al. (2009) "Fluorescence-activated droplet sorting (FADS): efficient microfluidic cell sorting based on enzymatic activity"; *Lab on a Chip*;9(13); pp. 1850-1858.
Battaglia G, et al; (2006) "Polymeric vesicle permeability: a facile chemical assay"; *Langmuir* 22(11); pp. 4910-4913.
Beer NR, et al; (2008) "On-chip single-copy real-time reverse-transcription PCR in isolated picoliter droplets"; *Anal Chem* 80; pp. 1854-1858.
Bernath, et al; (2004) "In vitro compartmentalization by double emulsions: sorting and gene enrichment by fluorescence activated cell sorting"; *Analytical Biochemistry* 325; pp. 151-157.
Bird et al., (1988) "Single-chain antigen-binding proteins"; *Science* 242; pp. 423-426.
Blainey PC. (2013) "The future is now: single-cell genomics of bacteria and archaea"; *FEMS microbiology reviews* 37(3); pp. 407-427.
Brouzes E, et al; "Droplet microfluidic technology for single-cell high-throughput screening"; *PNAS* vol. 106, No. 34; Aug. 25, 2009; pp. 14195-14200.
Brown, R. B. et al: (2008) "Current techniques for single-cell lysis"; *J. R. Soc. Interface* 5; pp. S131-S138.
Caron G.; (1998) "Assessment of bacterial viability status by flow cytometry and single cell sorting"; *Journal of applied microbiology* 84(6): pp. 988-998.
Chaffer C. L. and Weinberg R. A.; "A Perspective on Cancer Cell Metastasis"; *Science*, vol. 331; Mar. 25, 2011; pp. 1559-1564.
Chabert M, et al; (2005) "Droplet fusion by alternating current (AC) field electrocoalescence in microchannels"; *Electrophoresis* 26; pp. 3706-3715.

Chen C-M, et al; (2000) "Influence of pH on the stability of oil-in-water emulsions stabilized by a splittable surfactant"; *Colloids and Surfaces A: Physicochemical and Engineering Aspects* 170(2); pp. 173-179.
Chung, C. et al; (2010) "Droplet dynamics passing through obstructions in confined microchannel flow"; *Microfluidics Nanofluidics*, 9(6), pp. 1151-1163.
Clausell-Tormos, Jennifer, et al; "Droplet-based microfluidic platforms for the encapsulation and screening of Mammalian cells and multicellular organisms"; *Chemistry and Biology* 15; (May 2008); pp. 427-437.
Dejournette CJ, et al; (2013) "Creating Biocompatible Oil—Water Interfaces without Synthesis: Direct Interactions between Primary Amines and Carboxylated Perfluorocarbon Surfactants"; *Analytical chemistry.*;85(21); pp. 10556-10564.
Dietrich et al; "Effects of UV irradiation and hydrogen peroxide on DNA fragmentation, motility and fertilizing ability of rainbow trout (*Oncorhynchus mykiss*) spermatozoa"; *Theriogenology*. vol. 64; (Nov. 2005) pp. 1809-1822.
Duffy DC, et al; (1998) "Rapid Prototyping of Microfluidic Systems in Poly(dimethylsiloxane)"; *Anal. Chem.* 70; 4974-4984.
Eastburn Dennis J., et al; (2013) "Ultrahigh-Throughput Mammalian Single-Cell Reverse-Transcriptase Polymerase Chain Reaction in Microfluidic Drops"; *Anal. Chem.* 85; pp. 8016-8021.
Eastburn DJ,et al; (2013) "Picoinjection Enables Digital Detection of RNA with Droplet RT-PCR"; *PloS one.*;8(4):e62961.
Edd et al., (2008) Controlled encapsulation of single cells into monodisperse picoliter drop *Lab on a Chip*, 8(8); pp. 1262-1264.
European search report and opinion dated Feb. 8, 2016 for EP Application No. 13829925.
Frenz L, et al; (2009) "Reliable microfluidic on-chip incubation of droplets in delay-lines"; *Lab on a Chip* 9(10); pp. 1344-1348.
Garstecki P. et al; "Formation of droplets and bubbles in a microfluidic T-junction-scaling and mechanism of break-up"; *Lab Chip* 6; (2006); pp. 437-446.
Gevensleben H, et al; (2013) "Noninvasive Detection of HER2 Amplification with Plasma DNA Digital PCR"; *Clinical Cancer Research.*; 19(12); pp. 3276-3284.
Gribskov, et al; (1986) "Sigma factors from *E. coli*, B. subtilis, phage SP01, and phage T4 are homologous proteins"; *Nucl. Acids Res.* 14(6):6745-6763.
Hayward RC, et al; (2006) "Dewetting instability during the formation of polymersomes from block-copolymer-stabilized double emulsions"; *Langmuir* 22(10); pp. 4457-4461.
Herminghaus S, "Dynamical Instability of Thin Liquid Films Between Conducting Media"; *Physical Review Letter*, vol. 83, No. 12; Sep. 20, 1999; pp. 2359-2361.
Holland, et al; (1991) "Detection of specific polymerase chain reaction product by utilizing the 5'—3' exonuclease activity of Thermus aquaticus DNA polymerase"; *PNAS*, 88 (16); 7276-7280.
Holtze C., et al; (2008) "Biocompatible surfactants for water-in-fluorocarbon emulsions"; *Lab Chip* 8; pp. 1632-1639.
Horton et al; "Gene splicing by overlap extension: tailor-made genes using the polymerase chain reaction"; *Biotechniques*, vol. 54; Mar. 1, 2013; pp. 129-133.
Hu, Hoa et al; (2009) "Mutation screening in 86 known X-linked mental retardation genes by droplet-based multiplex PCR and massive parallel sequencing"; *HUGO J.*3; pp. 41-49.
Huebner et al; (2008) "Microdroplets: A sea of applications?"; *Lab on a Chip*, 8; pp. 1244-1254.
Hunkapiller and Hood, (1986) "Immunology: The growing immunoglobulin gene superfamily"; *Nature*, 323; pp. 15-16.
Hunt JA, et al; (1994) "Effect of pH on the stability and surface composition of emulsions made with whey protein isolate"; *Journal of Agricultural and Food Chemistry.*;42(10); pp. 2131-2135.
Huston et al; (1988) "Protein engineering of antibody binding sites: recovery of specific activity in an anti-digoxin single-chain Fv analogue produced in *Escherichia coli*"; *Proc. Natl. Acad. Sci. U.S.A.*, 85; pp. 5879-5883.
International search report and written opinion dated Feb. 21, 2014 for PCT/US2013/054517.
Ki, JS., et al. (2005) "Integrated method for single-cell DNA extraction, PCR amplification, and sequencing of ribosomal DNA

(56) References Cited

OTHER PUBLICATIONS from harmful Dinoflagellates Cochlodium polykrikoides and Alexandrium catenella"; Marine Biotechnology, vol. 6; pp. 587-593.
Kiss MM, et al.(2008) "High-Throughput Quantitative Polymerase Chain Reaction in Picoliter Droplets"; *Anal Chem* 80(23); pp. 8975-8981.
Kritikou Ekat; "It's cheaper in the Picolab"; *Nat Rev Genet*, 6; (Sep. 2005); pp. 668.
Lagally ET, et al; (2001) "Single-Molecule DNA Amplification and Analysis in an Integrated Microfluidic Device"; *Analytical Chemistry.*; 73(3); pp. 565-570.
Lanzavecchia et al; (1987) "The use of hybrid hybridomas to target human cytotoxic T lymphocytes"; *Eur. J. Immunol.* 17(1); pp. 105-111.
Leary JF. (1994) "Strategies for rare cell detection and isolation"; *Methods Cell Biol.*;42(Pt B); pp. 331-358.
Lim, Shuan and Abate Adam, (2013) "Ultrahigh-throughput sorting of microfluidic drops with flow cytometry"; *Lab Chip*13; pp. 4563-4572.
Link, et al; (2004) "Geometrically mediated breakup of drops in microfluidic devices"; *Phys Rev Lett.* 92(5):054503.
Livak KJ and Schmittgen TD; (2001) "Analysis of Relative Gene Expression Data Using Real-Time Quantitative PCR and the 2<sup>−ΔΔCT</sup> Method"; *methods.*; 25(4); pp. 402-408.
Longo MC, et al; (1990) "Use of uracil DNA glycosylase to control carry-over contamination in polymerase chain reactions"; *Gene.*; 93(1); pp. 125-128.
Malloggi F, et al; "Electrowetting-controlled droplet generation in a microfluidic flow-focusing device"; *J. Phys.: Condens. Matter* 19; (2007); 462101; 7 pages.
Markou Athina,et al; (2011) "Molecular Characterization of Circulating Tumor Cells in Breast Cancer by a Liquid Bead Array Hybridization Assay"; *Clinical Chemistry* 57:3; pp. 421-430.
Marcus et al., "Parallel Picoliter RT-PCR Assays Using Microfluidics"; *Analytical Chemistry*, 78(3); (2006); pp. 956-958.
Mary P Pascaline, et al; "Controlling droplet incubation using close-packed plug flow"; *Biomicrofluidics* 5; (2011); pp. 024101-1-024101-6.
Mazutis L, et al; (2013) "Single-cell analysis and sorting using droplet-based microfluidics"; *Nature protocols.*8(5); pp. 870-891.
McDonald, et al; (2000) "Fabrication of microfluidic systems in poly(dimethylsiloxane"; *Electrophoresis*, 21(1); pp. 27-40.
Medkova, Martina et al; "Analyzing Cancer at Single Cell Resolution with Droplet Technology"; *American Association of Cancer Research (AACR)*; Apr. 19, 2010; 1 page.
Metzker, Michael L. "Sequencing technologies—the next generation"; *Nature Reviews Genetics*, vol. 11 (Jan. 2010); pp. 31-46.
Miyazaki, K; (2002) "Random DNA fragmentation with endonuclease V: application to DNA shuffling"; *Nucleic Acids Res.* 30(24); e139.
Miyazaki et al. (2013) "A new large-DNA-fragment delivery system based on integrase activity from an integrative and conjugative element"; *Appl Environ Microbiol* 79(14); pp. 4440-4447.
Moon Sangjun, et al; "Drop-on-Demand Single Cell Isolation and Total RNA Analysis"; *PloS ONE*, vol. 6, Issue 3; e17455 (Mar. 2011); pp. 1-10.
Morton et al; (2008) "Crossing microfluidic streamlines to lyse, label and wash cells†"; *Lab on a Chip*, 8(9); pp. 1448-1453.
Mui B, et al; (1993) "Osmotic properties of large unilamellar vesicles prepared by extrusion"; *Biophysical journal* 64(2); pp. 443-453.
Nagrath Sunitha, et al; "Isolation of rare circulating tumour cells in cancer patients by microchip technology"; *Nature* 450(7173); Dec. 20, 2007; pp. 1235-1239.
Nakano M, et al. (2005) "Single-molecule reverse transcription polymerase chain reaction using water-in-oil emulsion"; *J Biosci Bioeng* 99; pp. 293-295.
Nikolova AN and Jones MN; (1996) "Effect of grafted PEG-2000 on the size and permeability of vesicles"; *Biochimica et Biophysica Acta (BBA)-Lipids and Lipid Metabolism.*;1304(2); pp. 120-128.

Novak, et al; (2011) "Single-cell multiplex gene detection and sequencing with microfluidically generated agarose emulsions"; *Angew Chem Int Ed Engl.* 50(2):390-395.
Oberholzer,Thomas, et al; (1995) "Polymerase chain reaction in liposomes"; *Chemistry & Biology* vol. 2 No. 10; pp. 677-682.
O'Donovan B, et al; (2012) "Electrode-free picoinjection of microfluidic drops"; *Lab Chip* 12; pp. 4029-4032.
Okochi M et al; (2010) "Droplet-based gene expression analysis using a device with magnetic force-based-droplet-handling system"; *J Biosci Bioeng.* 109(2); pp. 193-197.
Perry DJ; (1999) "Solid-Phase Sequencing of Biotinylated PCR Products with Streptavidin-Coated Magnetic Beads"; *Hemostasis and Thrombosis Protocols: Springer*; . p. 49-54.
Piatek AS, et al; (1998) "Molecular beacon sequence analysis for detecting drug resistance in Mycobacterium tuberculosis";. *Nat Biotechnol.*16(4); pp. 359-363.
Priest Craig, et al; (2006) "Controlled electrocoalescence in microfluidics: Targeting a single lamella"; *Appl Phys Lett*, 89; pp. 134101-1-134101-3.
Sciambi et al. (2013) "Adding reagent to droplets with controlled rupture of encapsulated double emulsions"; Biomicrofluidics 7(4); pp. 1-6.
Scott S. H, et al; (2011) "Microfluidic immunomagnetic multi-target sorting—a model for controlling deflection of paramagnetic beads"; *Lab Chip* 11; pp. 2577-2582.
Seemann R, et al; (2012) "Droplet based microfluidics"; *Rep Prog Phys* 75; pp. 016601.
Shui et al; (2011) "Microfluidic DNA fragmentation for on-chip genomic analysis" *Nanotechnology* 22(49): 494013. 7 pages.
Siegel Adam C,et al; (2007) "Microsolidics: Fabrication of Three-Dimensional Metallic Microstructures in Poly( dimethylsiloxane )"; *Adv Mater* 19; pp. 727-733.
Song H, et al; (2006) "Reactions in droplets in microfluidic channels" *Angew Chem Int Ed Engl* 45; pp. 7336-7356.
Squires Tom M.; "Microfluidics: Fluid physics at the nanoliter scale"; *Reviews of modern physics.*; 77(3); (Jul. 2005) pp. 977-1026.
Stone HA, et al; (2004) "Engineering flows in small devices: microfluidics toward a lab-on-a-chip"; *Annu Rev Fluid Mech.*; 36; pp. 381-411.
Stott Shannon L.; et al; "Isolation of circulating tumor cells using a microvortex-generating herringbone-chip"; *PNAS* vol. 107, No. 43; Oct. 26, 2010; pp. 18392-18397.
Syed et al. (2009) "Next-generation sequencing library preparation: simultaneous fragmentation and tagging using in vitro transposition"; *Nature Methods* vol. 6; pp. 1-2.
Tadmor AD, et al; (2011) "Probing individual environmental bacteria for viruses by using microfluidic digital PCR"; *Science.*;333(6038); pp. 58-62.
Takagi et al. (2005) "Continuous particle separation in a microchannel having asymmetrically arranged multiple branches" *Lab Chip*, 5(7); pp. 778-784.
Teh SY,et al; (2008) "Droplet microfluidics"; *Lab Chip* 8; pp. 198-220.
Tewhey Ryan, et al; "Microdroplet-based PCR enrichment for large-scale targeted sequencing"; *Nature Biotechnology*, vol. 27 No. 11; (Nov. 2009); pp. 1025-1035.
Thomann Y, et al; (2005) "PMMA Gradient Materials and in situ Nanocoating via Self-Assembly of Semifluorinated Hyperbranched Amphiphiles"; *Macromolecular Chemistry and Physics.*;206(1); pp. 135-141.
Thorsen T, et al; (2001) "Dynamic pattern formation in a vesicle-generating microfluidic device"; *Phys Rev Lett* 86; pp. 4163-4166.
Tsai Scott S. H., et al; (2011) "Microfluidic immunomagnetic multi-target sorting—a model for controlling deflection of paramagnetic beads"; *Lab Chip* 11; pp. 2577-2582.
Ullal, et al; (2014) "Cancer cell profiling by barcoding allows multiplexed protein analysis in fine needle aspirates"; *Sci Transl Med.* 6(219):219ra9; pp. 1-22.
Utada, et al; (2007) "Dripping to jetting transitions in coflowing liquid streams"; *Phys Rev Lett.* Aug. 31, 2007;99(9); pp. 094502-1-094502-4.

(56) References Cited

OTHER PUBLICATIONS

Vanapalli SA, et al; "Hydrodynamic resistance of single confined moving drops in rectangular microchannels"; *Lab Chip* 9 (2009); pp. 982-990.

Vickers, et al., (2006) "Generation of Hydrophilic Poly(dimethylsiloxane) for High-Performance Microchip Electrophoresis"; *Anal. Chem*, 78(21); pp. 7446-7452.

Wang C, et al; (2012) "Amphiphilic building blocks for self-assembly: from amphiphiles to supra-amphiphiles"; *Accounts of Chemical Research* 45(4); pp. 608-618.

Whitcombe D, et al; (1999) "Detection of PCR products using self-probing amplicons and fluorescence"; *Nature biotechnology* 17(8); pp. 804-807.

Whitesides GM. (2006) The origins and the future of microfluidics. *Nature* 442(7101); pp. 368-373.

Xia YN, et al; (1998) "Soft lithography"; *Angew Chem Int Edit* 37; pp. 551-575.

Zeng Yong, et al; "High-Performance Single Cell Genetic Analysis Using Microfluidic Emulsion Generator Arrays"; *Anal Chem*. 82(8); Apr. 15, 2010; pp. 3183-3190.

Zheng B, et al; (2004) "Formation of droplets of in microfluidic channels alternating composition and applications to indexing of concentrations in droplet-based assays"; *Anal Chem* 76; pp. 4977-4982.

Zhu et al., (2001) "Reverse transcriptase template switching: a SMART approach for full-length cDNA library construction"; *BioTechniques* 30: pp. 892-897.

Zien TF; (1969) "Hydrodynamics of bolus flow—an analytical approach to blood flow in capillaries"; *Math Biophys*, 31; pp. 681-694.

Zhong Qun, et al; (2011) "Multiplex digital PCR: breaking the one target per color barrier of quantitative PCR"; *Lab Chip* 11; pp. 2167-2174.

Fu, Yusi et al (2015) "Uniform and accurate single-cell sequencing based on emulsion whole-genome amplification"; Proc Natl Acad Sci U S A. 112(38); pp. 11923-11928.

Nishikawa, Yohei et al (2015) "Monodisperse Picoliter Droplets for Low-Bias and Contamination-Free Reactions in Single-Cell Whole Genome Amplification"; PLoS One 10(9); pp. e0138733.

Sciambia Adam and Abate Adam R., (2015) "Accurate microfluidic sorting of droplets at 30 kHz"; Lab Chip 15(1); pp. 47-51.

* cited by examiner

FIG. 8 Printer configuration

HIGH DEFINITION MICRODROPLET PRINTER

CROSS-REFERENCE

This application is a 35 U.S.C. 371 national stage entry of International Application No. PCT/US2015/056743, filed Oct. 21, 2015, which application claims priority benefit of U.S. Provisional Application No. 62/112,068, filed Feb. 4, 2015, and U.S. Provisional Application No. 62/067,314, filed Oct. 22, 2014, which applications are incorporated herein by reference in their entireties and for all purposes.

GOVERNMENT SUPPORT

This invention was made with government support under grant nos. HG007233, AR068129 and R01 EB019453 awarded by the National Institutes of Health; grant no. DBI1253293 awarded by the National Science Foundation; grant nos. HR0011-12-C-0065 and HR0011-12-C-0066 awarded by the Department of Defense, Defense Advanced Research Projects Agency; and grant no. N66001-12-C-4211, awarded by the Space Naval War Systems Center. The government has certain rights in the invention.

INTRODUCTION

Developments in droplet microfluidics have provided a robust tool set for the high-throughput manipulation and analysis of single cells and small reagent volumes. However, measurements and droplet manipulations are generally performed on droplets flowing single file through sub-regions of a microfluidic device, thus providing a limited ability to perform measurements over extended periods of time or to make targeted reagent additions to specific droplets.

SUMMARY

Methods for delivering discrete entities including, e.g., cells, media and/or reagents encapsulated therein to substrates are provided. In certain aspects, the methods include manipulating and/or analyzing qualities of the discrete entities or biological materials encapsulated therein. In some embodiments, the methods may be used to create arrays of microenvironments and/or for two and three-dimensional printing of tissues or structures. Systems and devices for practicing the subject methods are also provided.

The present disclosure provides methods of delivering discrete entities to a substrate, for example, by: flowing a plurality of discrete entities through a microfluidic device in a carrier fluid, wherein the discrete entities are insoluble and/or immiscible in the carrier fluid; directing the carrier fluid and one or more of the plurality of discrete entities through a delivery orifice to the substrate; and affixing the one or more of the plurality of discrete entities to the substrate.

The present disclosure also provides methods of printing one or more cell layers, for example, by: encapsulating cells in droplets including an aqueous fluid to provide cell-comprising droplets; flowing a plurality of droplets comprising the cell-comprising droplets through a microfluidic device in a carrier fluid, wherein the carrier fluid is immiscible with the aqueous fluid; directing the carrier fluid and a plurality of the cell-comprising droplets through a delivery orifice to a substrate; and affixing the plurality of the cell-comprising droplets to the substrate to provide a first layer of cell-comprising droplets, wherein the substrate comprises on a first surface a layer of fluid which is miscible with the carrier fluid and immiscible with the aqueous fluid, and wherein the plurality of the cell-comprising droplets are affixed to the first surface of the substrate following introduction into the layer of fluid on the first surface of the substrate.

The present disclosure also provides methods of printing and detecting one or more cells, for example, by: encapsulating cells in droplets including an aqueous fluid to provide cell-comprising droplets; flowing a plurality of droplets comprising the cell-comprising droplets through a microfluidic device in a carrier fluid, wherein the carrier fluid is immiscible with the aqueous fluid; directing the carrier fluid and a plurality of the cell-comprising droplets through a delivery orifice to the substrate; affixing the plurality of the cell-comprising droplets to the substrate, wherein the substrate includes on a first surface a layer of fluid which is miscible with the carrier fluid and immiscible with the aqueous fluid, and wherein the plurality of the cell-comprising droplets are affixed to the first surface of the substrate following introduction into the layer of fluid on the first surface of the substrate; and detecting one or more of the cells in the affixed cell-comprising droplets, a component of one or more of the cells in the affixed cell-comprising droplets, or a product of one or more of the cells in the affixed cell-comprising droplets.

The present disclosure also provides methods of printing a three-dimensional structure, for example, by: flowing discrete entities through a microfluidic device in a carrier fluid, wherein the discrete entities are insoluble and/or immiscible in the carrier fluid; and directing the carrier fluid and a first plurality of the discrete entities through a delivery orifice to a substrate to provide a first layer thereon; directing the carrier fluid and a second plurality of the discrete entities through the delivery orifice to the first layer to provide a second layer thereon; and one or more additional directing steps in which a plurality of the discrete entities are directed through the delivery orifice to an immediately preceding layer to provide a subsequent layer thereon, wherein a multilayer, three-dimensional structure is provided.

The present disclosure also provides methods of delivering droplets from a delivery orifice, for example, by: flowing a plurality of droplets through a microfluidic device in a carrier fluid, wherein the microfluidic device includes a sorter; detecting one or more of the plurality of droplets to provide one or more detected droplets; sorting via the sorter the one or more detected droplets from the plurality of droplets; and directing the carrier fluid and the one or more detected droplets through the delivery orifice.

The present disclosure also provides methods of affixing a droplet to a substrate, for example, by: delivering a droplet in a first carrier fluid from a microfluidic device, through an orifice, to a substrate surface; positioning the droplet in a second carrier fluid on the substrate surface; and affixing the droplet to the substrate surface via a force.

The present disclosure also provides methods of moving an affixed droplet on a substrate, for example, by: delivering a droplet in a first carrier fluid from a microfluidic device, through an orifice, to a substrate surface; positioning the droplet in a second carrier fluid on the substrate surface; affixing the droplet to the substrate surface via a force; and modulating the force so as to move the droplet from its affixed location to another location and/or applying a second force, which is sufficient, either alone or in combination with the modulated force, to move the droplet from its affixed location to another location.

The present disclosure also provides methods of adding reagents to a droplet, for example, by: delivering a first droplet in a first carrier fluid from a microfluidic device, through an orifice, to a substrate surface; positioning the droplet in a second carrier fluid on the substrate surface; affixing the droplet to the substrate surface via a force; delivering a second droplet to the same location as the first droplet affixed to the substrate surface or a location adjacent or proximate the first droplet on the substrate surface; and coalescing the first droplet and the second droplet such that the contents of the first droplet and the second droplet are combined.

The present disclosure also provides methods of adding reagents to a droplet, for example, by: delivering a droplet in a first carrier fluid from a microfluidic device, through a first orifice, to a substrate surface; positioning the droplet in a second carrier fluid on the substrate surface; affixing the droplet to the substrate surface via a force; inserting a second orifice fluidically connected to a reagent source into the droplet; and injecting via the second orifice one or more reagents into the droplet.

The present disclosure also provides methods of recovering all or a portion of an affixed droplet, for example, by: delivering a droplet in a first carrier fluid from a microfluidic device, through an orifice, to a substrate surface; positioning the droplet in a second carrier fluid on the substrate surface; affixing the droplet to the substrate surface via a force; and recovering all or a portion of the affixed droplet.

The present disclosure also provides methods of manipulating an affixed droplet, for example, by: delivering a droplet in a first carrier fluid from a microfluidic device, through an orifice, to a substrate surface; positioning the droplet in a second carrier fluid on the substrate surface; affixing the droplet to the substrate surface via a force; and modulating the immediate environment of the droplet, thereby modulating the contents of the droplet.

The present disclosure also provides methods of manipulating an affixed droplet by delivering a droplet in a first carrier fluid from a microfluidic device, through an orifice, to a substrate surface; positioning the droplet in a second carrier fluid on the substrate surface; affixing the droplet to the substrate surface via a force; at least partially solidifying the affixed droplet; removing the second carrier fluid from the substrate surface, wherein the second carrier fluid is immiscible with the contents of the affixed droplet prior to the at least partial solidification of the affixed droplet; replacing the removed second carrier fluid with a miscible fluid; and modulating a chemical composition of the miscible fluid, thereby modulating the affixed droplet.

The present disclosure also provides methods of porating a cell within an affixed droplet, for example, by: delivering a droplet in a first carrier fluid from a microfluidic device, through an orifice, to a substrate surface, wherein the droplet includes a cell; positioning the droplet in a second carrier fluid on the substrate surface; affixing the droplet to the substrate surface via a force; and porating the cell within the droplet.

The present disclosure also provides methods of analyzing a droplet on a substrate, for example, by: delivering a droplet in a first carrier fluid from a microfluidic device, through an orifice, to a substrate surface; positioning the droplet in a second carrier fluid on the substrate surface; affixing the droplet to the substrate surface via a force; and detecting one or more components of the affixed droplet.

The present disclosure also provides methods of delivering discrete entities to a substrate, for example, by: flowing a plurality of first discrete entities through a first microfluidic device in a first carrier fluid, wherein the first discrete entities are insoluble and/or immiscible in the first carrier fluid, and wherein the first microfluidic device includes a first delivery orifice; directing the first carrier fluid and one or more of the plurality of first discrete entities through the first delivery orifice to the substrate; flowing a plurality of second discrete entities through a second microfluidic device in a second carrier fluid, wherein the second discrete entities are insoluble and/or immiscible in the second carrier fluid, and wherein the second microfluidic device includes a second delivery orifice; directing the second carrier fluid and one or more of the plurality of second discrete entities through the second delivery orifice to the substrate; and affixing the one or more of the plurality of first discrete entities and the one or more of the plurality of second discrete entities to the substrate.

The present disclosure also provides methods of delivering discrete entities to a substrate, for example, by: flowing a plurality of discrete entities through a microfluidic device in a carrier fluid, wherein the discrete entities are insoluble and/or immiscible in the carrier fluid, and wherein the microfluidic device includes a plurality of delivery orifices; directing the carrier fluid and a first one or more of the plurality of discrete entities through a first delivery orifice of the plurality of delivery orifices to the substrate; directing the carrier fluid and a second one or more of the plurality of discrete entities through a second delivery orifice of the plurality of delivery orifices to the substrate; and affixing the first one or more of the plurality of first discrete entities and the second one or more of the plurality of discrete entities to the substrate.

The present disclosure also provides methods of analyzing a droplet, for example, by: flowing a plurality of droplets through a microfluidic device in a carrier fluid, encapsulating or incorporating unique identifier molecules into the plurality of droplets, such that each droplet of the plurality of droplets includes a different unique identifier molecule; delivering the plurality of droplets in a first carrier fluid from a microfluidic device, through an orifice, to a substrate surface; positioning the plurality of droplets in a second carrier fluid on the substrate surface; affixing the plurality of droplets to the substrate surface via a force; for each of the affixed plurality of droplets, recovering all or a portion of the affixed droplet and the unique identifier for each droplet; analyzing the recovered droplets or recovered portions thereof in conjunction with the unique identifier, wherein results of the analysis are identified as specific to material originating from particular droplets based on the presence of the unique identifier.

The present disclosure also provides methods of performing quantitative PCR, for example, by: partitioning a heterogeneous population of nucleic acids into a plurality of droplets including an aqueous fluid; encapsulating or incorporating quantitative PCR reagents into the plurality of droplets; flowing the plurality of droplets through a microfluidic device in a carrier fluid, wherein the carrier fluid is immiscible with the aqueous fluid; directing the carrier fluid and a plurality of droplets through a delivery orifice to a substrate; affixing the plurality of droplets to the substrate, wherein the substrate includes on a first surface a layer of fluid which is miscible with the carrier fluid and immiscible with the aqueous fluid, and wherein the plurality of droplets are affixed to the first surface of the substrate following introduction into the layer of fluid on the first surface of the substrate; incubating the affixed plurality of droplets under conditions sufficient for amplification of nucleic acids; and detecting nucleic acid amplification over time.

The present disclosure also provides methods of sequencing single cell nucleic acids, for example, by: partitioning a heterogeneous plurality of cells into a plurality of droplets including an aqueous fluid, such that each droplet includes not more than one cell; subjecting the plurality of droplets to conditions sufficient for lysis of the cells contained therein and release of cellular nucleic acids; encapsulating or incorporating unique nucleic acid identifier molecules into the plurality of droplets, such that each droplet of the plurality of droplets includes a different unique nucleic acid identifier molecule; linking the unique nucleic acid identifier molecules to one or more cellular nucleic acids in the plurality of droplets or to amplification products thereof; flowing the plurality of droplets through a microfluidic device in a first carrier fluid; delivering the plurality of droplets in the first carrier fluid from the microfluidic device, through an orifice, to a substrate surface; positioning the plurality of droplets in a second carrier fluid on the substrate surface; affixing the plurality of droplets to the substrate surface via a force; for each of the affixed plurality of droplets, recovering all or a portion of the affixed droplet, including cellular nucleic acids and the unique nucleic acid identifier for each droplet; sequencing nucleic acids from the recovered droplets or recovered portions thereof together with the unique identifier molecules, wherein the presence of the sequence of a unique identifier molecule in the sequence read of a nucleic acid molecule identifies the nucleic acid molecule as originating from a particular cell.

The present disclosure also provides methods of synthesizing a polymer on a substrate, for example, by: flowing a first droplet including a first droplet fluid through a microfluidic device in a carrier fluid, wherein the first droplet includes a first polymer or a first monomer; directing the carrier fluid and the first droplet through a delivery orifice to the substrate; affixing the first droplet to the substrate wherein the substrate includes on a first surface a layer of fluid which is miscible with the carrier fluid and immiscible with the first droplet fluid, and wherein the first droplet is affixed to the first surface of the substrate at a predetermined location following introduction into the layer of fluid on the first surface of the substrate; flowing a second droplet through the microfluidic device in the carrier fluid, wherein the second droplet includes a second polymer or a second monomer; directing the carrier fluid and the second droplet through the delivery orifice to the first droplet affixed at the predetermined location; incubating the first and second droplets under conditions sufficient for the contents of the first and second droplets to come into contact and for the first polymer or first monomer to form a covalent bond with the second polymer or monomer, thereby generating a synthesized polymer.

The present disclosure also provides methods of analyzing a droplet on a substrate, for example, by: partitioning a molecular library including a plurality of library members into a plurality of droplets including an aqueous fluid; delivering the plurality of droplets in a first carrier fluid from a microfluidic device, through an orifice, to a substrate surface; positioning the droplets in a second carrier fluid on the substrate surface; affixing the droplets to the substrate surface via a force; and performing one or more reactions in the affixed droplets with the library members; detecting the results of the one or more reactions in the affixed droplets and/or recovering all or a portion of the affixed droplets for further analysis.

The present disclosure also provides methods of printing microarrays, for example, by: delivering a plurality of droplets in a first carrier fluid from a microfluidic device, through an orifice, to a substrate surface, wherein each of the plurality of droplets includes a molecule; positioning the droplets in a second carrier fluid on the substrate surface; affixing the droplets at predetermined locations to the substrate surface via a force; incubating the substrate under conditions suitable for chemical bonding of the molecules comprised by the affixed droplets to the substrate surface, thereby providing an array of substrate-bound molecules.

The present disclosure also provides methods of performing in situ sequencing, for example, by: flowing a plurality of droplets through a microfluidic device in a carrier fluid, encapsulating or incorporating unique nucleic acid identifier molecules into the plurality of droplets, such that each droplet of the plurality of droplets includes one or more copies of a different unique nucleic acid identifier molecule; delivering the plurality of droplets in a first carrier fluid from a microfluidic device, through an orifice, to a surface of a tissue substrate; positioning the plurality of droplets in a second carrier fluid on the surface of the tissue substrate; affixing the plurality of droplets to the surface of the tissue substrate via a force; incubating the tissue substrate under conditions sufficient for the unique nucleic acid identifier molecules from each affixed droplet to bind to nucleic acids contained within the tissue substrate in proximity to the affixed droplet; sequencing the unique nucleic acid identifier molecules and the nucleic acids to which they are bound; and identifying and/or quantitating, using the unique nucleic acid identifier molecules, nucleic acids contained within the tissue substrate at locations corresponding to locations where particular droplets were affixed.

The present disclosure also provides methods of manipulating cells or embryos, for example, by: flowing a plurality of droplets through a microfluidic device in a carrier fluid, wherein each droplet of the plurality of droplets includes an aqueous fluid and a fertilized egg cell or embryo, and wherein the carrier fluid is immiscible with the aqueous fluid; directing the carrier fluid and the plurality of droplets through a delivery orifice to a substrate; affixing the plurality of droplets to the substrate, wherein the substrate includes on a surface thereof a layer of fluid which is miscible with the carrier fluid and immiscible with the aqueous fluid, and wherein the plurality of droplets is affixed to the surface of the substrate following introduction into the layer of fluid on the surface of the substrate; detecting within the affixed plurality of droplets the development of one or more embryos; and selecting and recovering an embryo from the affixed droplets.

The present disclosure also provides methods of manipulating cells or embryos, for example, by: flowing a plurality of droplets through a microfluidic device in a carrier fluid, wherein each droplet of the plurality of droplets includes an aqueous fluid and an unfertilized egg cell, and wherein the carrier fluid is immiscible with the aqueous fluid; directing the carrier fluid and the plurality of droplets through a delivery orifice to a substrate; fertilizing one or more of the egg cells in the plurality of droplets; affixing the plurality of droplets to the substrate, wherein the substrate includes on a surface thereof a layer of fluid which is miscible with the carrier fluid and immiscible with the aqueous fluid, and wherein the plurality of droplets are affixed to the surface of the substrate following introduction into the layer of fluid on the surface of the substrate; detecting within the affixed droplets the development of an embryo; and selecting and recovering specific embryos from the affixed droplets.

The present disclosure also provides systems and devices which may be utilized in the implementation of the methods describe herein. For example, the present disclosure provides a droplet printer including, for example: a microfluidic device including one or more droplet makers and one or more flow channels, wherein the one or more flow channels are fluidically connected to the one or more droplet makers and configured to receive one or more droplets therefrom; a delivery orifice fluidically connected to one or more of the one or more flow channels; and an automated system integrated with the delivery orifice, wherein the automated system (a) selectively positions the delivery orifice in proximity to a substrate during operation or (b) selectively positions the substrate in proximity to the delivery orifice during operation, such that a droplet can be ejected from the delivery orifice and deposited on the substrate.

The present disclosure also provides a system including, for example, a droplet printer including a substrate surface for receiving one or more droplets deposited by the delivery orifice of the droplet printer; and one or more of: (a) a temperature control module operably connected to the droplet printer, (b) a detection means operably connected to the droplet printer, (c) an incubator operably connected to the droplet printer, and (d) a sequencer operably connected to the droplet printer; and a conveyor configured to convey the substrate from a first droplet receiving position to one or more of (a)-(d).

The present disclosure also provides substrates which may be provided using the methods, devices and systems described herein, for example, a substrate including: a substrate surface comprising an immiscible phase fluid; and an ordered array of droplets positioned in the immiscible phase fluid, wherein the droplets are affixed to the substrate surface, and wherein the ordered array of droplets comprises at least 10,000 individual droplets.

The present disclosure also provides electrode array systems, for example, an electrode array system including: an array of individually controllable electrodes embedded in a substrate material; a power source; and a controller, wherein the controller is configured to selectively enable or disable an electrical connection between the power source and each individually controllable electrode in the array thereby providing an active an inactive electrode respectively, and wherein, each active electrode is capable of affixing a discrete entity to a surface of the substrate material in proximity to the active electrode when said discrete entity is deposited in proximity to the active electrode.

BRIEF DESCRIPTION OF THE DRAWINGS

The invention may be best understood from the following detailed description when read in conjunction with the accompanying drawings. Included in the drawings are the following figures.

DETAILED DESCRIPTION

Figure 1:
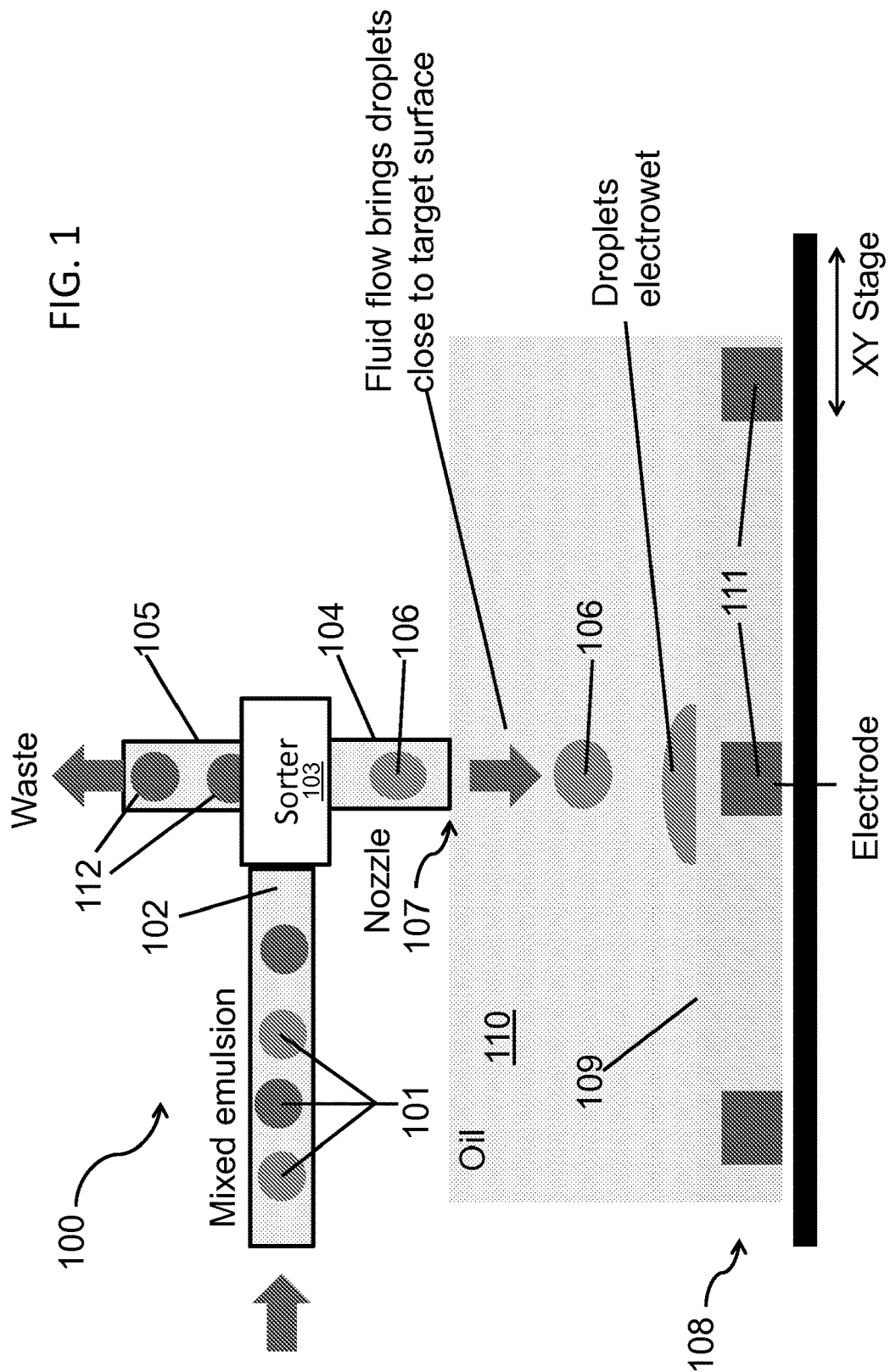
FIG. 1 provides a simplified depiction of a microfluidic system and method of the instant disclosure.

Methods for delivering discrete entities including, e.g., cells, media and/or reagents encapsulated therein to substrates are provided. In certain aspects, the methods include manipulating and/or analyzing qualities of the discrete entities or biological materials encapsulated therein. In some embodiments, the methods may be used to create arrays of microenvironments and/or for two and three-dimensional printing of tissues or structures. Systems and devices for practicing the subject methods are also provided.

The subject methods and devices may find use in a wide variety of applications, such as increasing the accuracy and/or efficiency of printing, e.g., microdroplet printing, and in assays involving, for example, well-plate analysis. Assays which can be performed in accordance with the subject disclosure may be relevant for the detection of cancer or other diseases, monitoring disease progression, analyzing the DNA or RNA content of cells, and a variety of other applications in which it is desired to detect and/or quantify specific components of a discrete entity.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a droplet" includes a plurality of such droplets and reference to "the discrete entity" includes reference to one or more discrete entities, and so forth.

It is further noted that the claims may be drafted to exclude any element, e.g., any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Further, the dates of publication provided may be different from the actual publication dates which may need to be independently confirmed. To the extent the definition or usage of any term herein conflicts with a definition or usage of a term in an application or reference incorporated by reference herein, the instant application shall control.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the disclosed subject matter include methods for the delivery of discrete entities, such as droplets, to one or more substrates and in some embodiments, affixing the discrete entities thereto. Aspects of the present disclosure include methods for printing one or more medium or cell layers as well as the detection of one or more qualities of components which are applied to a substrate. For example, some embodiments include methods for the detection, quantification, and/or genotyping of cells, e.g. normal cells (i.e., non-tumor cells), or tumor cells positioned on a substrate.

The subject methods, in some embodiments, include flowing one or more discrete entities through a microfluidic device in a carrier fluid, such as a carrier fluid in which the discrete entities are insoluble and/or immiscible. The methods also may include directing the carrier fluid and one or more of the discrete entities through a portion of a microfluidic device, such as a delivery orifice, to a substrate and/or affixing the one or more discrete entities to a substrate. Discrete entities may be affixed to a substrate, for example, by one or more forces, such as an electrical (e.g., dielectrophoretic), gravitational, and/or magnetic force.

Discrete entities as used or generated in connection with the subject methods, devices, and/or systems may be sphere shaped or they may have any other suitable shape, e.g., an ovular or oblong shape. Discrete entities as described herein may include a liquid phase and/or a solid phase material. In some embodiments, discrete entities according to the present disclosure include a gel material. In some embodiments, the subject discrete entities have a dimension, e.g., a diameter, of or about 1.0 μm to 1000 μm, inclusive, such as 1.0 μm to 750 μm, 1.0 μm to 500 μm, 1.0 μm to 100 μm, 1.0 μm to 10 μm, or 1.0 μm to 5 μm, inclusive. In some embodiments, discrete entities as described herein have a dimension, e.g., diameter, of or about 1.0 μm to 5 μm, 5 μm to 10 μm, 10 μm to 100 μm, 100 μm to 500 μm, 500 μm to 750 μm, or 750 μm to 1000 μm, inclusive. Furthermore, in some embodiments, discrete entities as described herein have a volume ranging from about 1 fL to 1 nL, inclusive, such as from 1 fL to 100 pL, 1 fL to 10 pL, 1 fL to 1 pL, 1 fL to 100 fL, or 1 fL to 10 fL, inclusive. In some embodiments, discrete entities as described herein have a volume of 1 fL to 10 fL, 10 fL to 100 fL, 100 fL to 1 pL, 1 pL to 10 pL, 10 pL to 100 pL or 100 pL to 1 nL, inclusive. In addition, discrete entities as described herein may have a size and/or shape such that they may be produced in, on, or by a microfluidic device and/or flowed from or applied by a microfluidic device.

In some embodiments, the discrete entities as described herein are droplets. The terms "drop," "droplet," and "microdroplet" are used interchangeably herein, to refer to small, generally spherically structures, containing at least a first fluid phase, e.g., an aqueous phase (e.g., water), bounded by a second fluid phase (e.g., oil) which is immiscible with the first fluid phase. In some embodiments, droplets according to the present disclosure may contain a first fluid phase, e,g, oil, bounded by a second immiscible fluid phase, e.g. an aqueous phase fluid (e.g, water). In some embodiments, the second fluid phase will be an immiscible phase carrier fluid. Thus droplets according to the present disclosure may be provided as aqueous-in-oil emulsions or oil-in-aqueous emulsions. Droplets may be sized and/or shaped as described herein for discrete entities. For example, droplets according to the present disclosure generally range from 1 μm to 1000 μm, inclusive, in diameter. Droplets according to the present disclosure may be used to encapsulate cells, nucleic acids (e.g., DNA), enzymes, reagents, and a variety of other components. The term droplet may be used to refer to a droplet produced in, on, or by a microfluidic device and/or flowed from or applied by a microfluidic device.

As used herein, the term "carrier fluid" refers to a fluid configured or selected to contain one or more discrete entities, e.g., droplets, as described herein. A carrier fluid may include one or more substances and may have one or more properties, e.g., viscosity, which allow it to be flowed through a microfluidic device or a portion thereof, such as a delivery orifice. In some embodiments, carrier fluids include, for example: oil or water, and may be in a liquid or gas phase. Suitable carrier fluids are described in greater detail herein.

FIG. 1 presents a non-limiting, simplified representation of one type of a microfluidics system and method according to the present disclosure. The particular embodiment depicted in FIG. 1 shows the delivery of discrete entities (droplets are illustrated by way of example) to a substrate. In one such method, discrete entities 101, e.g., droplets, are prepared using a device, e.g., a microfluidic device 100, and a carrier fluid 102 to produce a mixed emulsion including the discrete entities. A variety of suitable droplet makers are known in the art, which may be used to prepare the mixed emulsion, e.g., droplet makers described in PCT Publication No. WO 2014/028378, the disclosure of which is incorporated by reference herein in its entirety and for all purposes.

In some embodiments, the discrete entities are of more than one type, e.g., more than one composition and/or size, such as a first type, e.g., a type containing one or more cells of interest, and a second type, e.g., a type not containing one or more cells of interest. In some embodiments, the discrete entities may contain one or more beads, such as magnetic beads and/or conductive beads.

In some embodiments of the disclosed methods, microfluidic devices are utilized which include one or more droplet makers configured to form droplets from a fluid stream. Suitable droplet makers include selectively activatable droplet makers and the methods may include forming one or more discrete entities via selective activation of the droplet maker. The methods may also include forming discrete entities using a droplet maker, wherein the discrete entities include one or more entities which differ in composition.

Once prepared, a mixed emulsion may be moved, e.g., moved and/or flowed to another portion of the microfluidic device 100, such as a sorter 103. A subset of the discrete entities 101 may be separated using a sorter 103. A sorter 103 may be configured to detect and/or separate discrete entities, e.g., discrete entities present in a carrier fluid, having different types, e.g., different compositions and/or sizes, such as a first type, e.g., a type containing one or more cells of interest, and a second type, e.g., a type not containing one or more cells of interest. As such, a sorter 103 may provide one or more sorted discrete entities 106 (e.g., one or more discrete entities including a cell and/or nucleic acid of interest) and direct them via a first channel 104 to a nozzle including a delivery orifice 107 for delivery to a substrate 108. A sorter 103 may also provide one or more sorted discrete entities 112 (e.g., one or more discrete entities not including a cell and/or nucleic acid of interest) and direct them via a second channel 105 to a waste outlet.

In some embodiments, the discrete entities not sorted for delivery via a delivery orifice, are recovered and/or recycled by, for example, being re-injected into the carrier fluid upstream of the sorter 103. Various embodiments of the methods disclosed herein include repeated recycling of discrete entities not selected for delivery through the delivery orifice in a particular pass through the sorter. Sorting, according to the subject embodiments, is described in further detail below. Also, in various embodiments, one or more discrete entities, e.g., all the discrete entities present in a mixed emulsion, remain contained e.g., encapsulated, in a carrier fluid, e.g., a hydrophobic solution (e.g., oil), or a hydrophilic solution (e.g., an aqueous solution), prior to sorting and/or throughout a sorting process carried out by the sorter 103 and/or throughout the process of directing the one or more entities through a portion of a microfluidic device, e.g., a delivery orifice, and/or throughout a process of affixing the entities to a substrate.

As discussed above, a sorted subset of discrete entities of interest, e.g., discrete entities 106, (e.g., discrete entities containing one or more cells of interest), may in some embodiments, be directed through a delivery orifice 107 of a microfluidic device 100 to a substrate 108. In some embodiments of the methods, a microfluidic device 100, or a portion thereof, e.g., a delivery orifice 107, contacts a substrate, e.g., a substrate 108, or a portion thereof, to which it delivers discrete entities. In other embodiments, a microfluidic device 100, or a portion thereof, e.g., a delivery orifice 107, delivers discrete entities to a substrate, e.g., a substrate 108, or a portion thereof, by dispensing the discrete entities in a carrier fluid, e.g., a carrier fluid 102, in proximity to a surface of the substrate, for example into a fluid on the surface of the substrate (e.g., substrate fluid 110), which fluid is miscible with the carrier fluid and immiscible with the discrete entities.

A delivery orifice as described herein, e.g., a delivery orifice of a microfluidic nozzle as described herein, will generally have dimensions that are similar to the size of the droplets to be delivered therethrough. Accordingly, in some embodiments, a delivery orifice as described herein has a diameter of from about 1 μm to about 1000 μm, inclusive, e.g., from about 10 μm to about 300 μm, inclusive. In some embodiments, a delivery orifice as described herein has a diameter of from about 1 μm to about 10 μm, from about 10 μm to about 100 μm, from about 100 μm to about 500 μm, or from about 500 μm to about 1000 μm, inclusive.

The nozzle can be molded as part of a microfluidic sorter as described herein, or can be a separate part that is mated with a microfluidic sorter as described herein. Suitable materials for the nozzle may include, e.g., polymeric tubing, small bore hypodermic tubing, and modified glass capillaries.

Figure 2:
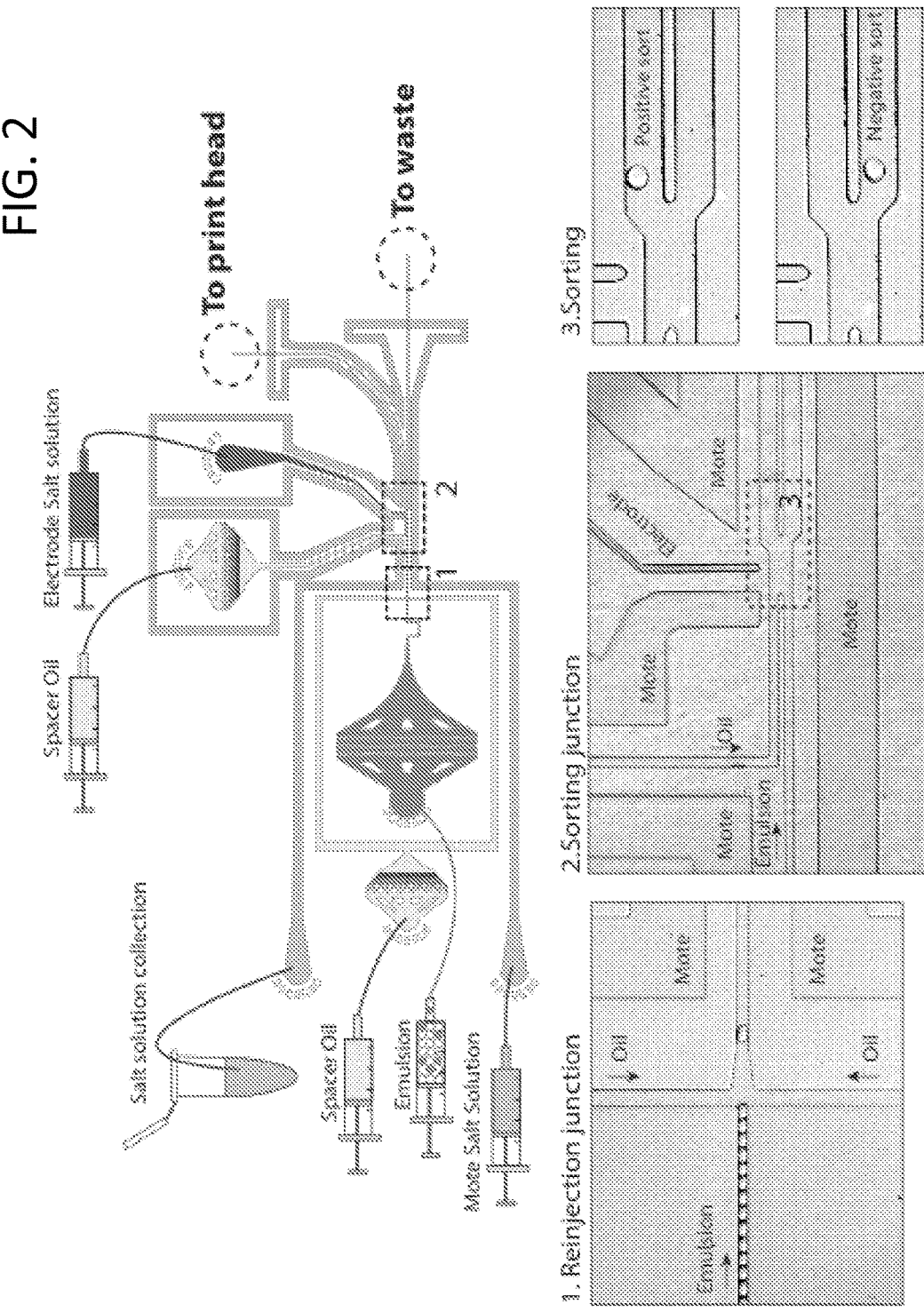
FIG. 2 depicts one embodiment of a subject device and associated methods, including methods of sorting discrete entities. An embodiment of a reinjection junction, sorting junction and a process of sorting by making a positive or negative sort are specifically illustrated in panels 1-3.

One embodiment of the subject systems, devices and methods is now described with reference to FIG. 2, which illustrates a microfluidic system including a microfluidic device including a sorting junction. As shown in FIG. 2, a microfluidic device is employed to apply and sort a mixed emulsion in order to deliver select discrete entities, e.g., droplets, to a delivery orifice, e.g., a delivery orifice of a print head. The microfluidic device utilizes a moat salt solution (to generate the field gradient used for dielectrophoretic deflection and to limit stray fields that can cause unintended droplet merger), spacer oil, and an electrode salt solution to facilitate sorting. The microfluidic device depicted provides junctions including a reinjection junction for providing a discrete entity-containing emulsion to be sorted and a sorting junction including a sorter for sorting, e.g., by making positive and negative sorts of discrete entities. Sorting may be accomplished, e.g., by applying an electric field via an electrode, e.g., a liquid electrode including, e.g., an electrode salt solution.

In certain embodiments, liquid electrodes include liquid electrode channels filled with a conducting liquid (e.g. salt water or buffer) and situated at positions in the microfluidic device where an electric field is desired. In particular embodiments, the liquid electrodes are energized using a power supply or high voltage amplifier. In some embodiments, the liquid electrode channel includes an inlet port so that a conducting liquid can be added to the liquid electrode channel. Such conducting liquid may be added to the liquid electrode channel, for example, by connecting a tube filled with the liquid to the inlet port and applying pressure. In particular embodiments, the liquid electrode channel also includes an outlet port for releasing conducting liquid from the channel.

The microfluidic device depicted in FIG. 2 also includes outlets to one or more print heads and to a waste container or channel.

As discussed above, some embodiments, such as those described in connection with FIG. 1, include affixing one or more discrete entities 101 to a substrate 108. Substrate 108 includes a surface, e.g., a surface 109, upon which a layer of fluid, e.g., substrate fluid 110, e.g., oil, may be provided or deposited. Suitable substrate fluids may include, for example, one or more liquids in which discrete entities are insoluble and/or immiscible, such as water and/or oil depending on the nature of the discrete entities. Substrate fluids may be the same type of fluid as a carrier fluid, e.g., a fluid having the same composition as a carrier fluid, e.g., a fluid including water and/or oil, or may be a different type of fluid than the carrier fluid, e.g., a fluid including water and/or oil.

In some embodiments, the disclosed methods may include moving one or more discrete entities through a device and/or affixing one or more discrete entities to a substrate and/or removing the discrete entities from the substrate by changing the buoyancy of the discrete entities and/or exerting one or more forces on one or more components, e.g., beads, of the discrete entities. Embodiments of the methods also include releasing one or more discrete entities, e.g., an affixed discrete entity, from a substrate by, for example, modulating, e.g., modulating by removing, one or more force affixing the entity to the substrate. In some instances, discrete entities are removed from a substrate by removing an electric field affixing them thereto.

To facilitate the above manipulations, the present disclosure provides, in some embodiments, a substrate which includes an array of individually controllable electrodes. Such substrates may be configured such that individual electrodes in the array can be selectively activated and deactivated, e.g., by applying or removing a voltage or current to the selected electrode. In this manner, a specific discrete entity affixed via a force applied by the electrode may be selectively released from a substrate surface, while unselected discrete entities remain affixed via application of the force. The electrodes of such an array may be embedded in a substrate material (e.g., a suitable polymer material), e.g., beneath a surface of the substrate to which the discrete entities are affixed via application of the force. A variety of suitable conductive materials are known in the art which may be utilized in connection with the disclosed electrode arrays, including various metals. Liquid electrodes as described previously herein may also be used for such an application.

Figure 6:
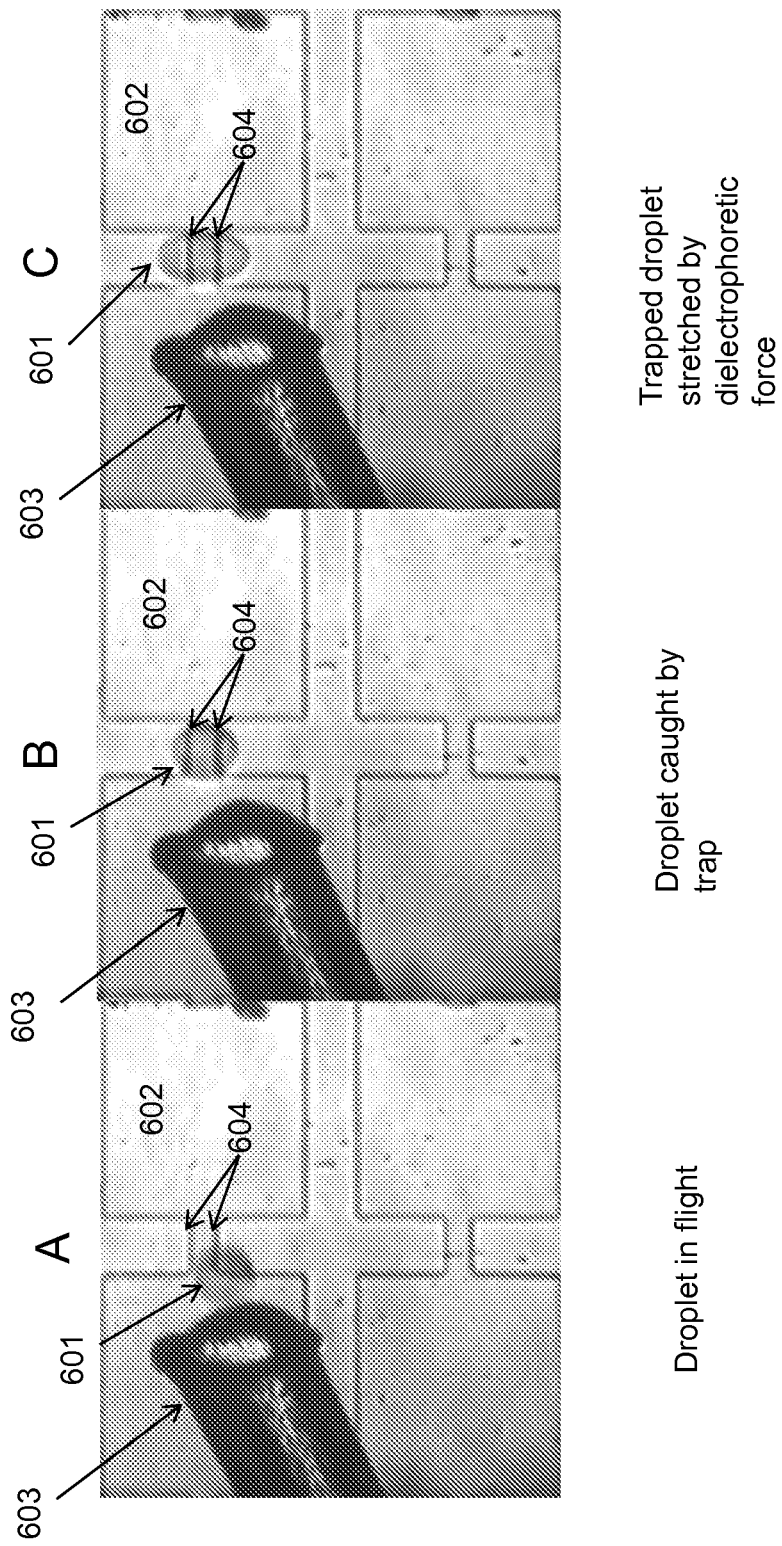
FIG. 6, Panels A-C, illustrate one embodiment of affixing a discrete entity, e.g., a droplet, generated in a microfluidic device to a substrate by applying a force, e.g., a dielectrophoretic force. Panel A shows a droplet being ejected from a microfluidic nozzle. Panel B shows the droplet caught at a gap separating electrode features. Panel C illustrates stretching of the trapped droplet via the application of dielectrophoretic force.

Methods and devices for affixing discrete entities to a substrate are now described. One embodiment of affixing a discrete entity, e.g., a droplet 601, generated in a microfluidic device, to a substrate 602, by applying a force, e.g., a dielectrophoretic force, is shown in FIG. 6, panels A-C. FIG. 6, panel A, shows a droplet 601 being ejected from a delivery orifice of a microfluidic nozzle 603 of a microfluidic device and prior to affixation to a substrate 602. Imbedded electrodes features 604 are patterned beneath the surface of substrate 602. FIG. 6, panel B, shows the droplet caught at a gap separating electrode features 604. Panel C illustrates the stretching of the trapped droplet via the application of dielectrophoretic force. Positioning of the substrate 602 relative to the nozzle 603 is achieved, for example, with a computer controlled mechanical stage. Alternatively, or in addition, the nozzle 603 may be provided as part of a print head, e.g., a computer controlled print head, which is movable relative to substrate 602.

The subject methods also include methods of adding reagents to a discrete entity, e.g., a droplet, e.g., a droplet affixed to a substrate. Such methods may include delivering and/or affixing a first discrete entity in a first carrier fluid to a substrate or a portion thereof, e.g., a substrate surface. The methods may also include delivering one or more other discrete entities, e.g., a second droplet, such as a discrete entity in a second carrier fluid and/or including one or more reagents, to a location on the substrate which is the same location as the first discrete entity or a location adjacent or in proximity to that of the first discrete entity. The first and subsequent applied discrete entities may then be coalesced such that the contents, including, for example, one or more reagents, of the first and subsequent discrete entities are combined. In some embodiments, coalescence is spontaneous and in other embodiments, coalescing discrete entities includes applying a force, such as an electrical force, to one or more of the discrete entities. For example, applying an electrical field to two or more droplets in close proximity can induce dynamic instability at the oil-water interfaces that results in droplet merger to reduce the surface energy of the oil-water system. The first and second carrier fluids, as described above, may be the same type of fluid or different types of fluids.

Some embodiments of this disclosure also include methods of adding one or more reagent and/or components, such as one or more beads, to one or more discrete entities, e.g., droplets, by delivering one or more discrete entities in a first carrier fluid via a first orifice of a device to a surface of a substrate. The methods may also include positioning one or more of such discrete entities in a second carrier fluid, e.g., a carrier fluid which is of the same or a different type than the first carrier fluid, on the substrate surface and/or affixing the discrete entities to the substrate via a force. According to the subject methods, an orifice of a device, such as an orifice operably connected, e.g., fluidically connected, to a reagent source, may then be inserted into one or more of the affixed discrete entities. Upon insertion, the orifice may be utilized to inject one or more reagents into the one or more discrete entities.

Embodiments of the methods may include modulating the environment of a discrete entity and thereby modulating the contents of the discrete entity, e.g., by adding and/or removing contents of the droplet. Such modulation may include modulating a temperature, pH, pressure, chemical composition, and/or radiation level of an environment of one or more discrete entities. Such modulation may also be of the immediate environment of one or more discrete entities, such as an emulsion in which the discrete entities are provided and/or one or more space, such as a conduit, channel, or container, within a microfluidic device. An immediate environment of a discrete entity which may be modulated may also include a fluid volume, such as a fluid flow, in which the discrete entity is provided. One or more discrete entities may also be stored in a modulated environment.

The methods of this disclosure may also include recovering all or a portion of one or more discrete entities which have been affixed to a substrate. For example, one or more materials, such as one or more solvents and/or reagents may be recovered from a droplet via, for example, extraction. Such a recovery may be conducted by contacting one or more affixed discrete entities with a portion of a device, such as a microfluidic orifice connected to a suction device for sucking one or more material, such as one or more solvent and/or reagent from one or more affixed discrete entity. A microfluidic orifice may be inserted into a discrete entity and/or placed in proximity to a discrete entity, e.g., placed at a distance from a discrete entity having an order of magnitude of a discrete entity or smaller, for performing recovery from the entity. Embodiments of the methods of recovery from a discrete entity may also include shearing, e.g., detaching, a discrete entity from a substrate surface by, e.g., increasing the buoyancy of one or more discrete entities. The buoyancy of a discrete entity can be increased by increasing the volume of the discrete entity by, for example, injecting aqueous fluid or non-aqueous fluid into the discrete entity.

In some embodiments, the methods may include concentrating one or more components, e.g., beads, present in a discrete entity at a location within a discrete entity. Such concentrated components or alternatively, portions of the discrete entity not containing the components, may then be selectively removed, e.g., removed by suction, from the discrete entity. One or more components removed from discrete entities may then be conveyed into one or more isolated containers via, for example, a delivery orifice.

In various aspects, substrates for use in connection with the disclosed methods include one or more channels filled with one or more conductive, e.g., electrically conductive, liquid or solid materials, e.g., an electrode material. In some embodiments, such substrates may also include an insulating sheet positioned between the channels and the carrier fluid. In some embodiments, one or more channels are configured, e.g., patterned, to generate an electric field above a portion of a substrate, such as an insulating sheet, upon application of a voltage to the one or more channels. In some embodiments, such a voltage and a resulting electrical field or an aspect thereof, e.g., a dielectrophoretic force, is sufficient to affix one or more discrete entities to the substrate. In some embodiments, a substrate, or a portion thereof, includes one or more electrodes having a net charge which is opposite in polarity, e.g., negative or positive, relative to the polarity of one or more discrete entities, e.g., droplets, being affixed to the substrate.

As shown in FIG. 1, in some embodiments, surfaces of substrates include one or more electrodes 111. In various embodiments, one or more electrodes are pre-formed on a substrate or portion thereof, e.g., a substrate surface. Substrates may, in various embodiments, be mounted upon and/or adjacently to, e.g., contacting, a stage, such as a movable stage, such as a stage movable in an X-Y and/or Z direction. In some embodiments, a stage is movable in a direction toward and/or or away from a microfluidic device, or a portion thereof, e.g., a delivery orifice 107. Also, in some embodiments, a microfluidic device, or a portion thereof, e.g., a delivery orifice 107 is movable in a direction toward and/or or away from another portion of a device, e.g., a stage, and/or a substrate. A stage and/or a microfluidic device, or a portion thereof, e.g., a delivery orifice, may be movable in constant movement or in increments on a scale of a diameter or radius of one or more discrete entities, e.g., 5 or less, 10 or less, 50 or less, or 100 or less discrete entities. A stage and/or a microfluidic device, or a portion thereof, may be movable in one or more direction, e.g., an X and/or Y and/or Z direction, in one or more increments having a distance of, for example, 1 µm to 1000 µm, inclusive, such as 1.0 µm to 750 µm, 10 µm to 500 µm, 1 µm to 50 µm, or 1 µm to 10 µm, inclusive. In some embodiments, the devices may me movable in constant movement or one or more increments on a scale to correspond with positions on a substrate where discrete entities may be attached, such as wells on a well plate including any of the well plates described herein.

In some embodiments, the methods include affixing one or more discrete entities 101 to a substrate 108, or a portion thereof, e.g., a surface 109, via wetting, e.g., electrowetting. In some embodiments, wetting includes moving, e.g., flowing, one or more discrete entities 106 from a delivery orifice 107, through a substrate fluid 110, to a substrate surface 109 of a substrate. In some embodiments, the wettability of a substrate is sufficient to attach one or more discrete entities to the substrate via, for example, wetting forces. In some embodiments, the methods include modifying, e.g., increasing or decreasing, the wettability of a substrate so as to be sufficient to affix a discrete entity to the substrate via wetting forces. Various aspects of the methods may also include applying exogenous electromagnetic radiation in an amount sufficient to affix a discrete entity to a specific location on a substrate.

In some embodiments, the subject methods include patterning one or more channels, e.g., channels of a substrate or aspects thereof, to provide a plurality of charged electrode features in a grid pattern. Such an arrangement is shown, for example, in FIG. 4, which depicts a substrate 401, including electrode features 402 and 403. A nozzle including delivery orifice 406 is also shown. Droplets are affixed to the grid pattern using dielectrophoresis, which allows the application of forces to uncharged conductive droplets suspended in a nonconductive medium. For example, in one embodiment, unaffixed droplets 408 experience a net force towards the regions on the surface of the substrate with the highest electric field gradient, the gap 405 between oppositely charged features 402 and 403. Once droplets are brought to the substrate surface, the surfactant layer stabilizing the droplets is disrupted, and the droplet wets the region 405. Due to the abrupt changes in geometry, the highest electric field gradients occur at the boundaries between charged features 402 and 403 and the gap 405. Droplets wetting the region 405 experience a lateral force towards 402 and 403, which causes a flattening and elongation of the droplet that is proportionate to the applied electric field. The charged features 402 and 403, do not necessarily need to have constant and opposite polarities. For example, high electric field gradients in 405 can be created by electrifying feature 402 with a high voltage AC signal (1.5 kV, 30 kHZ) while grounding feature 403. As long as feature 403 is an adequate conductor, an ungrounded feature 403 will experience charge reorganization as a result of an applied AC signal on 402, and will provide a function similar to grounding this feature. This effect is known as electromagnetic shielding. The patterned substrate depicted in FIG. 4 may be fabricated using standard microfluidics techniques. For example, a molded PDMS device may be placed with microfluidic channels facing up and bonded to a thin polymer film. After punching, the channels may be filled with a saltwater solution and attached to a power supply, where one network of channels becomes feature 402 and the other network of channels becomes feature 403.

As illustrated in FIG. 1, affixing one or more discrete entities, e.g., discrete entities 101, to a substrate, e.g., a substrate 108, or a portion thereof, e.g., a surface 109, may include attaching the discrete entities to the substrate, e.g., substrate 108, via a force, such as a gravitational, electrical, and/or magnetic force. As such, in some embodiments, a delivery orifice, e.g., a delivery orifice 107, is positioned above a substrate 108. In some embodiments, the methods include applying an electrical voltage and/or current to electrodes, e.g., electrodes 111, positioned in or on the substrate, e.g., substrate 108. Affixing one or more discrete entities, e.g., discrete entities 101, to a substrate, e.g., a substrate 108, or a portion thereof, may also include affixing the entities to the substrate via interfacial tension.

Figure 5:
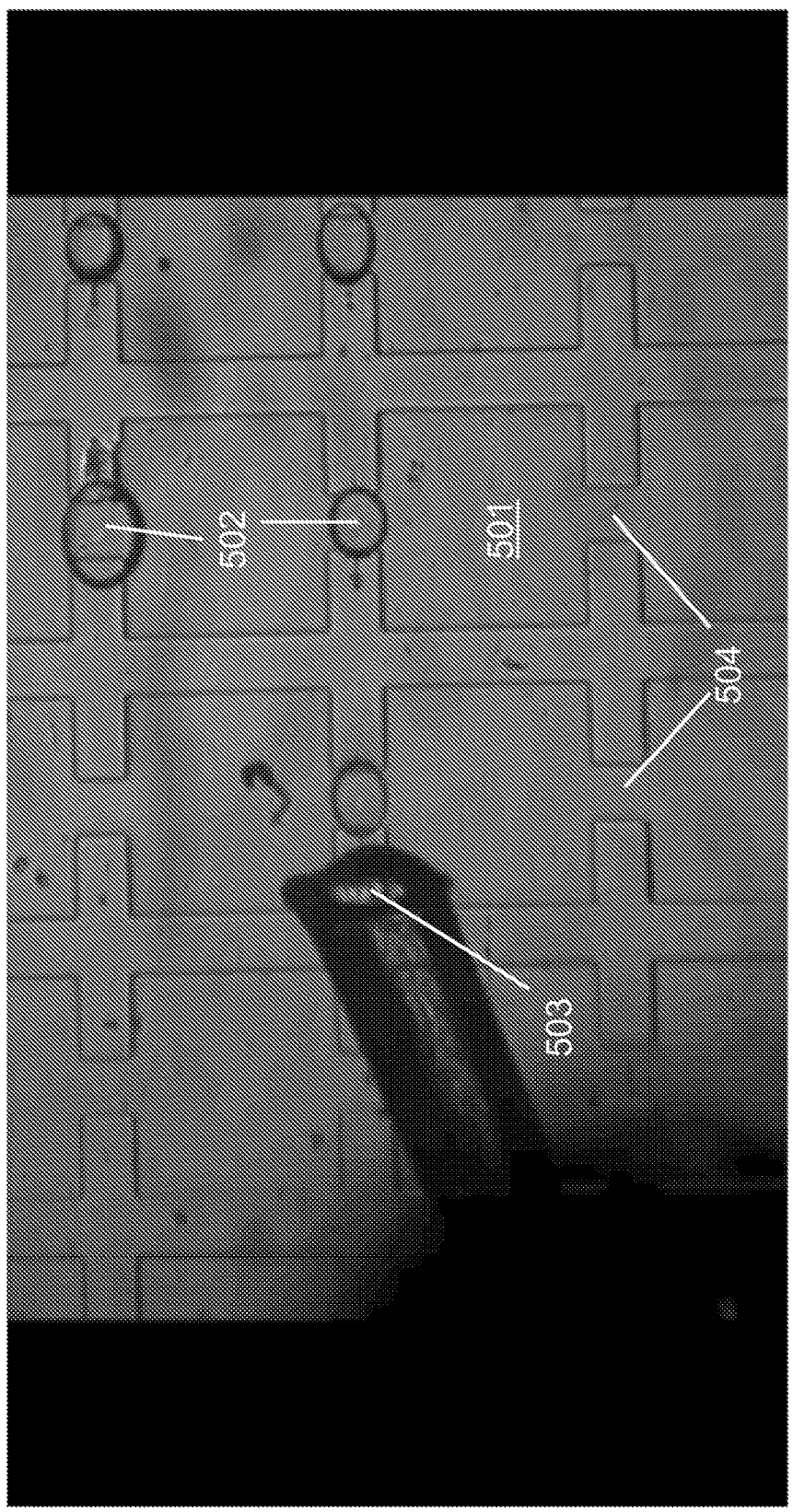
FIG. 5 illustrates aspects of the subject devices and methods including a patterned substrate having unfilled positions where discrete entities may be affixed and filled positions where discrete entities are affixed.

Methods of affixing are also shown in FIG. 5 wherein discrete entities 502 are delivered to a patterned substrate 501 via an orifice, e.g., a delivery orifice 503, of a microfluidic device. FIG. 5 also illustrates unfilled positions 504 on a substrate 501 where discrete entities may be affixed, e.g., affixed by a force, such as a dielectrophoretic force, to the substrate.

Embodiments of the disclosed methods, for example the disclosed methods as described with reference to FIG. 1, may also include a step or steps of storing one or more discrete entities, e.g., one or more discrete entities 106 which are affixed to a substrate, e.g., a substrate 108, or a portion thereof, e.g., a surface 109. Methods of storing the discrete entities may include maintaining one or more affixed entities under controlled environmental conditions, e.g., at a fixed temperature and/or pressure, for a storage period. In some embodiments, one or more forces are applied and/or maintained to maintain the one or more affixed entities in an affixed state for the entire storage period.

In some embodiments of the disclosed methods, one or more microfluidic devices are integrated with an automated system which selectively positions one or more portions of the microfluidic devices, e.g., one or more delivery orifices, relative to a substrate or a portion thereof, e.g., a substrate surface. Accordingly, in some embodiments the methods include selectively positioning, e.g., positioning at a particular location using an automated system, one or more delivery orifices relative to a substrate or a portion of a substrate to selectively deliver one or more discrete entities to one or more locations on or in proximity to the substrate or a portion thereof, e.g., a substrate surface. Automated systems as disclosed may include one or more control units, e.g., control units including a central processing unit, to control one or more aspects of applying discrete entities to a substrate, such as physical positioning of one or more delivery orifice and/or timing of discrete entity dispensing. Automated systems may be configured to position, e.g., position independently, one or more delivery orifices with respect to a stationary substrate or position a substrate with respect to one or more stationary delivery orifices. Aspects of the subject methods may include delivering a first member of a plurality of discrete entities to a first location on or in proximity to a substrate or a portion thereof, e.g., a substrate surface, and a second member of the plurality of discrete entities to the first location or a second location on or in proximity to the substrate.

The subject methods may also include modulating, e.g., changing one or more aspect of, one or more force, e.g., by modulating an electric field and/or buoyancy of a discrete entity in one or more carrier solution, to thereby move one or more discrete entities, e.g., a droplet, from a first affixed location on a substrate to another location. The methods may also include applying one or more additional, e.g., second, force which is sufficient to move one or more discrete entities from a first affixed location to a second location on a substrate and/or affix the one or more discrete entities at the second location. Aspects of the methods may also include applying a cross flow of fluid and/or exogenous electromagnetic radiation sufficient to move a discrete entity from a first location, e.g., a first affixed location, on a substrate to a second location on a substrate.

Embodiments of the subject methods may also include performing one or more assays, e.g., one or more biological assays, such as any of the assays described herein, on and/or in one or more of the discrete entities before and/or after delivery of a discrete entity to a substrate or a portion thereof, e.g., a substrate surface. In some embodiments, such substrates may include a well plate or a portion thereof. The term "well plate", is used broadly herein, to refer to a plate having one or more wells, e.g., divots or compartments, therein, such as a mictrotiter plate. However, as used herein, the term "well plate" may also refer to a patterned array of discrete entities, e.g., droplets, as described herein, which discrete entities are affixed to a substrate surface. In such embodiments, the substrate surface may include traditional wells, such as divots or compartments, but may alternatively be a flat surface.

Figure 7:
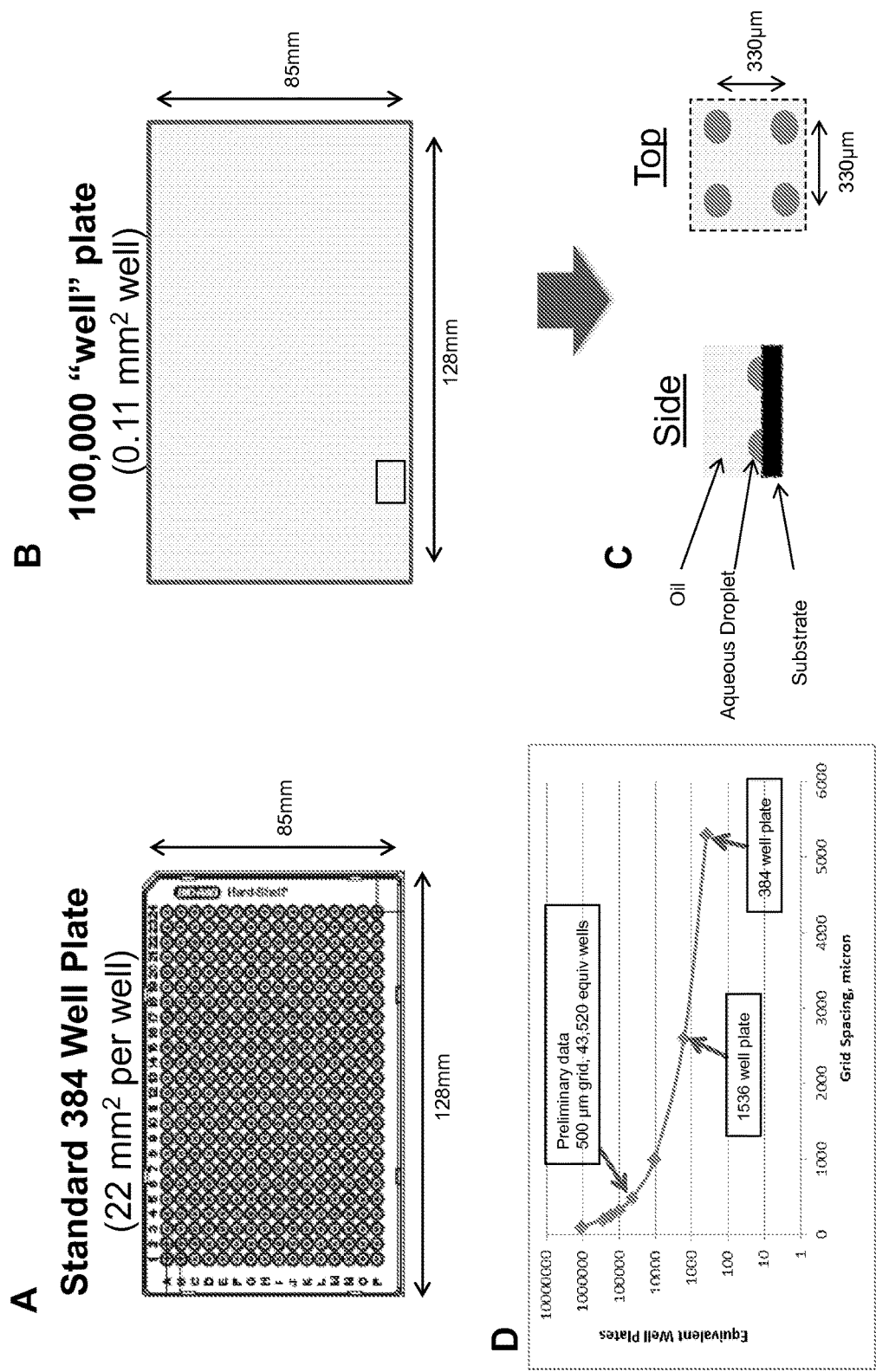
FIG. 7, Panels A-D, illustrate aspects of well plates and projected array densities which may be achieved using the methods, devices and systems of the present disclosure. Panel A: A standard 384 well plate. Panel B: A "well" plate which may be generated using the subject methods. Panel C: Side and top views of a substrate having of four proximately-affixed droplets thereon. Panel D: A graph demonstrating how the subject methods, for example using pico-drop printing, can increase the array density within a standard well plate footprint.

Standard assays employ well plates having, for example, a 384 well format, such as the well plate shown in FIG. 7, panel A. However, well plates which may be prepared and/or utilized in accordance with the subject methods and devices, e.g., well plates including ordered arrays of discrete entities, may include well plates having, for example, from 20,000 to 500,000, inclusive, wells, such as from 50,000 to 150,000, inclusive, such as from 80,000 to 120,000, inclusive, such as 100,000 wells. Such a well plate, which may have the same size footprint as the well plate of FIG. 7, panel A, is illustrated, for example, by FIG. 7, panel B (e.g., a 128 mm×85 mm footprint). In such a well plate, each well may have an area ranging, for example, from 0.01 $mm^2$ to 1 $mm^2$, inclusive, such as from 0.05 $mm^2$ to 0.5 $mm^2$, such as about 0.10 $mm^2$. Additionally, FIG. 7, panel C, illustrates magnified top and side views of a portion of the well plate shown in FIG. 7, panel B. FIG. 7, panel C, specifically illustrates an oil layer on a substrate having aqueous droplets affixed thereon.

Furthermore, FIG. 7, panel D, provides a graph demonstrating how the subject methods, for example using pico-drop printing, can increase the array density using a standard well plate footprint. Accordingly, the methods described herein enable a significantly increased array density within a standard well plate footprint allowing for the performance of a significantly increased number of assays and/or experiments. Such methods allow, for example, the performance of assays on a number of samples that is significantly higher than is achievable in a set amount of time and/or using a set amount of space according to standard methods.

Aspects of the disclosed methods may also include controlling, e.g., maintaining, the temperature of one or more discrete entities before and/or after delivery of the one or more entities to a substrate or a portion thereof, e.g., a substrate surface. For example, in some embodiments, one or more discrete entities are thermalcycled before and/or after delivery to a substrate or a portion thereof, e.g., a substrate surface.

The subject methods may also include printing a structure, e.g., a three-dimensional structure, by employing a device, such as the device depicted generally in FIG. 1. In some embodiments, the methods include directing a first layer and/or a second layer and/or one or more additional layers, e.g., 3 to 1000 layers, inclusive, such as 10 to 500 or 50 to 100 layers, of discrete entities, e.g., droplets, to a substrate or a portion thereof, e.g., a substrate surface. In some instances, a substrate, or a portion thereof, e.g., a substrate surface, includes thereon a layer of aqueous fluid which is miscible with a carrier fluid and immiscible with the fluid of the discrete entities, and wherein the droplets are affixed to a surface of a substrate, e.g., a substrate surface, following their introduction into the layer of aqueous fluid. In various embodiments, the discrete entities include one or more solid and/or gel materials, such as one or more polymers. Aspects of the disclosed methods may also include initiating and/or sustaining a reaction, e.g., a photopolymerization reaction, which causes discrete entities and/or a carrier fluid of discrete entities to solidify, e.g., solidify on a substrate to which the discrete entities are applied.

EXEMPLARY EMBODIMENTS

Exemplary, non-limiting embodiments of the present disclosure are provided below. While these are described with respect to droplets, droplet "printing", and related devices and systems, it should be understood that such embodiments may be equally applicable to the printing of non-droplet discrete entities as well.

In one embodiment of the present disclosure, an emulsion including droplets of different composition is "printed" to a substrate using a microfluidic print head, e.g., as described herein. The droplets are made ahead of time using a microfluidic or non-microfluidic technique, such as flow focusing or membrane emulsification, respectively. The pre-formed droplets are then introduced into the print head and sorted on demand according to their fluorescence. The droplet solutions are dyed with different solutions prior to being encapsulated as droplets so that, when injected into the print head, a detection technique, such as flow dropometry, can be used to identify each droplet's type and, using this information, a computer can determine which droplets to sort.

This allows dispensing of precise solutions to the substrate. Once dispensed by the print head, the droplets are affixed to the substrate using a force such as, for example, a dielectrophoretic force that is generated via electrodes fabricated under the substrate surface. A layer of oil above the substrate allows the droplets to remain in the carrier fluid at all times, that is, the droplets are in the carrier fluid after generation, flowed via carrier fluid throughout the print head, and then dispensed into a carrier-fluid coated substrate. This keeps the droplets encapsulated at all times and protects against evaporation. In addition to dielectrophoresis, other forces can also be applied to affix the droplets. For example, an electrical force can be applied in which the substrate can be charged oppositely to the droplets, creating an electrical attraction. The droplets can be charged as they pass through the microfluidic print head using a channel comprising charged fluid that contacts the droplets or, for example, a salt water electrode as described herein. Other forces that can be used are, for example, gravitational, in which the density of the droplets being larger than that of the carrier fluid causes them to sink into a well patterned on the substrate or float into a an upside-down well, if less dense than the carrier fluid. Magnetic forces can be used in similar ways. Wetting and chemical forces can also be used such that the droplets, upon contacting the substrate, wet the surface and are adhered to it via surface tension.

In addition to a suitably designed "emulsion ink" including droplets of different type labeled with detection components that make each type distinguishable, a "sorting on demand" microfluidic device for directing specific droplets to the substrate at controlled times, and a substrate constructed so as to maintain droplets at specific locations, a system which automates positioning of the substrate under the dispensing nozzle with the sorting on demand device helps provide for high-speed targeted dispensing of droplets. This can be accomplished using, for example, electrically-controlled microscope stages to position the substrate under the nozzle, and a computer to detect and sort droplets on demand and in registry with the substrate.

The droplet dispenser is, in essence, a highly miniaturized and extremely high throughput liquid handling robot and, as such, it is valuable for performing a variety of applications, particularly biological assays. For example, droplets comprising reagents, cells, and other components, can be dispensed to the substrate, subjected to changing environmental conditions, such as heating for incubation, and monitored over time to measure reaction activity. The results obtained from monitoring the system can be integrated together with the dispensing platform to, for example, change the conditions in specific droplets by adding additional reagents based on reaction progress.

In some embodiments of the present disclosure, the described system can be used to "print" cells and tissues. In such embodiments, the cells or tissue building blocks are first encapsulated in droplets labeled with detection components along with necessary biological reagents, such as matrigel or collagen. The resulting emulsion ink, which can contain cells of different types, cell aggregates, or biological reagents without cells, can then be sorted on demand via the print head and dispensed to the substrate, where they are affixed with a force. To localize cells on the array, traps can be positioned with space between them. To print tissues, the cells are preferably deposited sufficiently close so as to allow neighboring droplets to coalesce and the cells contained within them to interact with one another. This can be used, for example, to print a "red" cell next to a "green" cell next to a "blue" cell. These steps can be repeated to make a line of cells in a desired pattern. Additional lines can then be printed adjacent to the first line to print a flat layer of cells. Additional layers can then be printed above the first layer, to generate a 3D multi-layered "tissue". With proper selection or engineering of the cells, once the tissue is printed, the cells can interact with one another to further modify the structure. Additional droplets can be added to modulate the structures development, such as biological reagents or drugs.

In similar embodiments, cell aggregates of defined type can be localized on the array in separate droplets. For example, a first position on the array can be dispensed with a specific combination of cells, such as a red, then a green, and then a blue cell. These cells will be dispensed into the same droplet by droplet addition in which they can then interact to perform functions. This can be repeated at additional spots on the array to build multiple identical aggregates or different, defined aggregates. This can be used, for example, to build elementary tissue structures composed of just tens of thousands of cells, or to study interactions between different cell types such as bacterial and mammalian cells, or microbes with infecting virus. Drugs and other chemical and biological compounds can also be added to the droplets, for example, to study how to modulate the interactions between the organisms.

In some embodiments the described system can be used to analyze cells. In some such embodiments, cells are isolated in the droplets on the array and additional materials are added as needed. The materials can stimulate the cells to grow, express defined pathways associated proteins, or include a microbe or virus that can infect the cells. Using a detection technique, such as optical detection, fluorescence, Raman microscopy, or other spectrographic techniques that preserve the droplets and the cells within them, it would be possible to monitor the droplets over time. This could be used, for example, to detect a change in a specific reaction or time-dependent expression of a target pathway. Using other techniques, including destructive techniques like mass spectrometry, PCR, or sequencing, with or without molecular barcodes, it would be possible to detect molecular information.

In some embodiments, cell-free experiments can be performed in the arrayed droplets. For example, cell-free extracts such as transcription and translation machinery can be encapsulated in the droplets, along with other components, including, if desired, cells. These can then be incubated on the array and monitored over time, as described above, to track progress of the reaction. This can be used, for instance, to screen pathways for activity in cell-free extracts and to investigate how pathway activity is modulated with changing conditions, such as the application of heat or presence of different inducers, inhibitors, etc.

Synthetic Biology Screening:

The methods described herein can be used to perform screens for synthetic biology applications such as, for example, screening cells or cell-free extracts engineered to express biological pathways that produce molecules. By isolating the pathways in droplets on the array and tracking the production of the molecules using methods like microscopy, spectroscopy, or mass spectrometry, it is possible to test different pathway sequences for desired activity.

Mass Spectrometry Activated Sorting:

In another embodiment, the described system can be used to sort droplets or cells using a mass-spec read out. For example, droplets containing different materials or cells can be dispensed to the array. A portion of each droplet can then be sampled and introduced into a mass spectrometry, to analyze its contents. Based on the information obtained, all or a portion of the droplet can be recovered for additional use.

3D Printing with Materials:

In another embodiment of the disclosed methods, discrete materials comprising solids, liquids, or solidifiable materials can be printed to the substrate, to generate planar or "3D" structures. For example, solid particles can be generated using a variety of processes, such as emulsion polymerization or droplet-based templating in which the material is emulsified into droplets while liquid and then solidified to convert a liquid droplet into a solid particle of similar dimensions. An "ink" comprising these solid particles can be generated by mixing together multiple particles of different type with different labels that can be determined optically. The particle-based ink can then be introduced into the print head and sorted on demand to the substrate, thereby depositing solid particles to the substrate in the desired pattern. Trapping forces like electrostatic or magnetic forces can also be used to localize the particles at defined positions. A first layer of particles can be deposited, and afterwards, additional layers can be added, to generate 3D structures in which the composition of each particle in the structure is defined exactly. Once deposited, a variety of methods can be used to bond the particles together such as, for example, chemical bonding techniques or sintering of the particles. In a slightly different embodiment, the aforementioned "3D printer" can print liquid droplets that can be solidified after being dispensed using, for example, chemical cross linking, polymerization, or gelation. The materials that are printed can comprise hydrophilic or hydrophobic liquids, metals, and plastics, with the carrier fluid and forces being selected as needed to enable controlled sorting on demand and dispensing of the materials to the substrate.

Sorting on Demand:

In microfluidic and other applications it is often desirable to generate droplets of defined type on demand. One method for accomplishing this is using a microfluidic droplet generator controlled by a membrane valve. When the valve is closed, the dispersed phase does not flow and no droplets are generated. When it is opened, it flows and droplets are generated. This approach can generate droplets on demand as fast as the valve can opened and closed, which is often no faster than 100 Hz. In addition, the droplets are all formed of the same fluid; to enable generation of droplets on demand from multiple fluids, multiple devices, each with its own fluid, may be interfaced together; this is challenging for more than a handful of fluids. Such a challenge may be addressed by embodiments of the present disclosure wherein droplets are generated on demand by sorting them, from a preexisting emulsion, on demand. The droplets of the different desired fluids are first emulsified separately and combined into a single mixed emulsion. They are labeled to enable them to be differentiated from one another using optical detection, such as flow cytometry. This combined emulsion is then injected into a microfluidic sorter which scans the droplets and sorts them down two channels, a dispensing channel and a waste channel. From the perspective of the dispensing channel, this system includes a droplet on demand technique since, by diverting droplets down the dispensing channel on demand, droplets are ejected from the channel on demand. The emulsion that is sent into waste can be recycled through the sorter, to conserve reagents. The value of this droplet on demand technique is that it is limited in speed to the rate at which the droplets can be sorted. With new sorting geometries incorporating gapped dividers between the sorting outlets (as described in greater detail herein), it is possible to sort droplets at >30 kHz, which is more than two orders of magnitude faster than can be achieved with published droplet on demand techniques. In addition, the combined emulsion can contain droplets of many different types, not just tens of droplets but hundreds or thousands of droplets. This allows sequences of droplets of unprecedented complexity to be generated, which is important in connection with the described printing technology for allowing controlled dispensing and combining of different reagents at each substrate location.

The sorting on demand device provides the control which facilitates dispensing defined sequences of droplets, but the trapping substrate allows for the capture those droplets at specific locations so that one or more assays of interest can be performed on them. There are a variety of substrates that can be constructed for trapping the droplets. One such substrate uses dielectrophoresis to trap the droplets. To generate the dielectrophoretic traps, the substrate may be fabricated so as to contain electrodes with which to generate the requisite electric fields. This can be accomplished by patterning electrodes under a dielectric sheet; the electrodes can be energized with positive and negative charges to generate large electric fields with a spatial gradient; when droplets are dispensed above the substrate and in the region of the field, dielectrophoretic forces will cause them to be attracted to the substrate, and adhere. The electrodes can be patterned using conventional fabrication techniques, such as metal sputtering or deposition on the sheet, or by fabricating microfluidic channels that can be bonded face-side-up to the bottom side of the sheet such that the channels are below the sheet and not in fluidic communication with the fluids above the sheet. The channels can then be filled with conductive medium, such as solder or electrolyte solution and charged to generate the desired electric fields for dielectrophoretic droplet tapping. By modulating the shapes, widths, and heights of the microfluidic channels, it is possible to structure the electrodes, thereby providing control over the fields that are applied to the droplets above the sheet.

Affixing Droplets:

In some embodiments, it is desirable to affix liquid or solid entities to the surface of a substrate via application of a force. One such force that can be used is dielectrophoresis, in which a patterned array of electrodes under the dielectric substrate is used to generate electric fields that dielectrophoretically attract or repel the entities, trapping them at the desired locations.

Non-dielectrophoretic electrical forces can also be used. In such embodiments, the entities can be charged with, for example, a positive charge, either before, during, or after their flow through the print head. The substrate can then be charged oppositely, creating an electrical attraction between the entities and the substrate that will affix them. The polarity of the entities and substrate can also be modulated to generate a repulsive force allowing, for example, droplets to be ejected from the substrate. Electrodes can be used for these purposes. For example, the substrate can be uniformly charged with one polarity so that droplets of the opposite polarity will stick to the substrate. Provided a dielectric separates the electrode from the droplets, no charge will flow between the two and the force will remain; alternatively, if the two are allowed to come into electrical contact, then charge will flow, removing the force but allowing, for example, a droplet to wet to the electrode and be affixed by interfacial tension forces.

In another embodiment, the electrodes can be patterned so that each trap has a single or multiple electrodes with the same or different polarity and charge. This can be used, for example, to generate dielectrophoretic traps appropriate to affix single droplets. Each electrode can be addressable and a large array of the traps can be fabricated into the substrate, allowing each drop to be switched on or off as desired. This can be used, for example, to capture droplets to specific traps by modulating the strength of the field of the trap where the droplet is to be affixed relative to other traps in the vicinity. The traps can also be turned off, to selectively release drops.

Different affixing forces are also possible, such as wettability and interfacial tension forces. In such embodiments, the substrate can be patterned with regions that alternate between hydrophilic and hydrophobic. For example, the substrate can be natively hydrophobic but patterned with small islands large enough to accommodate one or multiple drops with hydrophilic wettability. The wettability patterning can be accomplished with, for example, spatially-modulated light-based polymer grafting or flow patterning of polyelectrolyte layers. Once the droplets are in contact with the hydrophilic patch, they may wet spontaneously or they may be induced to wet, for instance if surfactants are present, by applying a small, transient or long-lived electric field. Once wetted to the substrate, the droplets can be maintained for periods of time.

A method to trap droplets, which utilizes interfacial tension, may be accomplished with patterned features. For example, wells can be fabricated into the substrate and sized and/or shaped such that droplets fit therein and, due to buoyancy or density differences with the carrier fluid, sit within the wells. The droplets can also be dispensed within a concave feature with a narrow opening, or between posts with narrow gaps. Such droplets may be held in place due to their interfacial tension and preference for remaining spherical.

Other kinds of electromagnetic traps can be generated using, for example, laser tweezers. Using an array of lasers directed at controlled locations on the substrate, droplets dispensed near the lasers may experience a force attracting or repelling them to or from the lasers, again generating a series of traps that can be used to localize the droplets. Magnetic droplets or particles can be affixed using magnetic or electromagnetic forces such as, for example, with ferrofluids, permanent magnets, paramagnetism, or electromagnetism generated by flowing electric current through an electrode patterned under the substrate.

Modulating the Position of Droplets:

Once droplets are dispensed to the substrate, it is possible to change the position of the droplets on the substrate. This can be accomplished, e.g., magnetically, by modulating the magnetic field, electrically or dielectrophoretically, by modulating electric fields, via electrowetting on dielectric, or by varying the position of optical traps with the lasers, among other forces. The carrier fluid, e.g., oil, surrounding the droplets can also be flowed so as to apply a shear to the droplets affixed to the substrate, causing them in some instances to move in the direction of the flow. If the droplets have a different density from the carrier fluid, buoyancy can also be used to move the droplets by altering the orientation of the substrate in a gravitational field.

Adding Reagents to Droplets:

In some embodiments, it may be desirable to dispense multiple droplets or discrete entities to a single location on the substrate array. This is valuable, for example, for adding different reagents to localized droplets at different and defined times. This can be accomplished by, for example, dispensing a first droplet to the array and then dispensing a second droplet to the same position as the first droplet. In certain embodiments, such as when electric fields are used to trap the drops, the electric fields generated by the substrate are sufficient to induce the droplets to merge, thereby combining their contents. The contents of the droplets can be mixed via diffusion or convective flow in the droplets generated by, for example, convection of the carrier fluid over the surface of the droplet or motion of the droplet when the trap is moved. In other instances, droplets will merge spontaneously, such as when no surfactants are used. In other instances, merger can be induced via application of a laser or localized heating. Additional drops can be added to the same location to add, one, two, three, or more droplets to the same position. Using the droplet or sorting on demand techniques, the drops that are added and the sequence in which they are added can be controlled exactly. In another embodiment, a nozzle or capillary can be introduced into the affixed droplet to inject the desired reagent.

Recovering Droplets or Material Therefrom:

In certain applications, it is desirable to recover all or portions of the affixed droplets. This can be accomplished, for example, by bringing a nozzle close to the affixed droplet and drawing fluid into the nozzle, thereby drawing the droplet into the nozzle. Alternatively, the nozzle can be used to generate a localized flow of carrier fluid which can be used to dispel droplets from the surface by overcoming the affixing force. If the nozzle shape is designed appropriately and the fluid flow adequate, it is also possible to recover a portion of the droplet in a mechanism similar to microcapillary-based droplet generation. Alternatively, or in addition, droplets can be removed from the substrate by adding additional liquid to them to increase their buoyancy; once the buoyant force is larger than the affixing force, the droplet will detach from the substrate and float away. If the droplets are heavier than the carrier, a similar result can be accomplished by inverting the substrate. In embodiments in which the traps can be selectively switched on and off, droplets can also be recovered by switching off the force and using buoyancy or flow to remove them from the substrate and recover them into a collection container.

Concentrating Materials in Droplets:

In some embodiments, it is desirable to concentrate reagents or other materials in the droplets. This can be accomplished using available techniques for concentrating reagents such as, for example, placing beads in the droplets that can bind certain components in the droplets, and then either removing the bead or the portion of the droplet that does not contain the bead to achieve a concentration increase.

Secondary Manipulation of Droplets:

The portions or complete droplets recovered with any of the methods described herein can then be dispensed into a secondary container by flowing them from the array into the container. For example, using the section method, individual droplets or droplet portions can be recovered from the droplet array and these portions flowed through a tube into a well on a well plate, where they are dispensed. This can be done one droplet at a time, dispensing each droplet into a separate well and thereby preserving the isolation of the droplets from one another. Once in the well, other operations can be perfumed on the droplet, such as propagating cells contained therein or performing biological reactions, such as ELISA, PCR, etc. Molecular analysis using techniques like microscopy, spectroscopy, and mass spectrometry can also be performed on the recovered entities.

Manipulating Affixed Droplets:

Affixed droplets can be manipulated using a variety of techniques to modulate their environment. For example, in some embodiments, it is possible to modulate the chemical, temperature, or pressure environment of the droplets to perform, for example, PCR by thermocycling the droplets. The carrier fluid can also be replaced to modulate the chemical properties of the droplet and to transport materials in and out of the droplets. For example, carrier phases with surfactant may undergo micellar transport, allowing compounds to be transported into or out of the droplets without merging droplets together. This can be used, for example, to stain compounds, e.g., oil-based compounds, with dyes that have an affinity for oil, e.g., nile red, by saturating the carrier with nile red and flowing it over the droplets for a period. In some embodiments, once the droplets are affixed, surfactants may no longer be necessary since the droplets need not be in contact; the traps can be spaced as necessary to accomplish this. In this scenario, the micellar transport can be reduced by replacing the oil with an oil that contains no surfactant. This could be valuable for enhancing the containment of compounds in the droplets that otherwise would leak out due to micellar transport. Similarly, the droplets can be dispersed using a carrier phase that is optimized for this step, and then the carrier replaced with a different carrier that has other desirable properties, such as the ability to enhance or reduce the partitioning of reagents out of or into the droplets. These kinds of environmental manipulations can be used to prepare the droplets for longer-term storage, such as at low temperature, to preserve reagents within them.

Alternatively, or in addition, the substrate can be fabricated to have a semi-permeable membrane that allows chemical communication with the droplets from below the substrate (or above depending on the orientation of the substrate relative to the droplets). By modulating the fluids under the membrane, chemical partitioning can be used to modulate the contents of the droplets while still preserving the droplets intact. For example, this can be used to change the buffering properties of the droplets by dispensing the droplets with a first buffer, e.g., containing ions, and then using the membrane, placing the droplets in chemical communication with another buffer with different ions, allowing the ions in the droplets to be replaced with those from the new buffer solution. By controlling the permeability of the membrane, the types of compounds that are modulated can be controlled based on, for example, their size, hydrophobic, charge, or chemical properties.

Analyzing Affixed Droplets:

In some applications of the invention, it is desirable to analyze the contents of the affixed droplet. For example, this is valuable for monitoring the change of a detectable marker, such as a fluorescent signal resulting from, e.g., PCR amplification or the fluorescent product of an enzymatic substrate used in an ELISA. In these instances, the droplets may be analyzed in a similar way to which the volumes of a well plate are analyzed with a plate-reader. They can be monitored over time, to collect information of how these signals vary over time. This can be used, for example, to screen a pathway that produces a peak concentration in product as a function of time, in which the peak height and width are both important parameters for optimization of the pathway, or to perform quantitative PCR in the droplets on nucleic acids or cells.

Multiple measurement modalities can be used, such as bright field, fluorescence, and absorbance techniques. Spectrographic techniques can also be applied, such as Raman spectroscopy, NMR, and mass spectrometry. Separation techniques can also be used, such as capillary electrophoresis by making contact with the droplets through, for example, a nozzle or capillary. By recovering all or portions of the droplets, the material can also be subjected to destructive or non-destructive techniques, such as mass-spectrometry and chemical analysis. Importantly, since the nozzle position is known during the material recovery process, the signals and information recovered from these and other assays can be traced back to specific droplets on the array, allowing time-resolved information to be combined with powerful molecular analysis techniques, such as sequencing of the material in the droplet portions.

Parallel Print Heads:

A single print head is limited in the rate at which it can dispense droplets to the substrate. One technique for dispensing droplets more quickly is to parallelize the print heads. In this approach, multiple nozzles can be attached to a single droplet on demand device and/or sorter on demand device so that, when a droplet is triggered, it is split into multiple portions, each of which is dispensed to the substrate at a different, defined location. This can also be used to dispense groups of droplets that were known to originate from the same parent droplet, and are thus related in certain ways. Due to the modular nature of the print heads, it is also possible to assemble multiple print heads together into a single device. For example, the use of the fiber optics for the detection of the droplets allows the detection optics to be localized to a small region in the device, while the sorting or droplet on demand devices, themselves, are only hundreds of microns in total size. This allows multiple devices to be assembled on a single chip so as to dispense droplets out of a single combined nozzle, or multiple outlet nozzles. In theory, this should allow printing at rates increased by a factor equal to the number of devices assembled on the print head.

Tagging Droplets with a Unique Identifier:

In certain applications it is valuable to tag the contents of the printed droplets with a unique identifier. This allows for the contents of multiple droplets to be pooled together while keeping track of from which droplet each entity originated. One such example of this is nucleic acid tagging, or barcoding. In this approach, for example, single cells can be localized in the droplets, lysed, and their nucleic acids tagged with unique identifiers relating from which droplet, and thus, from which cell (in the case of single cell encapsulation), each nucleic acid originated. The nucleic acids can then all be pooled and sequenced and the tags used to group them according to single droplets and cells. Other examples in which this would be valuable would be the tagging of different segments of a viral genome or the amplification, fragmentation, and tagging the portions of a long DNA molecule, allowing, in essence, long sequence reads to be generated from short, tagged reads.

Multiple Fibers for Detection:

To analyze the fluorescence of a droplet, it is necessary to provide excitation light, e.g., in the form of a laser, and read the generated emission light. In some embodiments of the invention, this can be accomplished using a single optical fiber that serves both to funnel the excitation light into the device and also collects the emitted light in the reverse direction. A drawback of this approach, however, is that the optical properties that are ideal for excitation light guidance may not be the same as for emission light capture. For example, to excite a narrow beam, a fiber with a narrow tip is preferred, but to collect the largest number of emitted photons, a wide fiber with a large collecting cone angle is preferred. In these instances, multiple fibers can be used. For example, a narrow fiber can be used to provide a concentrated, excitation signal, while a wide fiber can collect the emitted fluorescent light.

qPCR in Printed Droplets:

In some embodiments, the methods, devices, and/or systems described herein can be used to quantitate nucleic acids. In this approach, sample droplets comprising nucleic acids are dispensed to the substrate. Reagents necessary for amplification are also added to the droplets, either by combining them with the sample droplets prior to dispensing, or by dispensing additional droplets to the positions of the sample containing droplets, wherein the additional droplets include the necessary reagents and a detection component, where the detection component signals the amplification. The droplet are then incubated under conditions suitable for amplification and monitored to read the detection component. This provides, for each droplet, a rate of change of the detection component which can be used to quantitate the nucleic acids in the droplets. In addition to quantitating DNA and RNA, this approach can also be used to quantitate the nucleic acids within living organisms, including viruses and single cells. In such embodiments, additional steps suitable for efficient cell lysis, such as the inclusion of lysis buffers, may be implemented using droplet addition.

Single Cell Barcoding:

In some embodiments, the methods, devices, and/or systems described herein can be used to sequence single cells. For example, individual cells can be encapsulated in the droplets and dispensed to the substrate as described herein. The cells can then be lysed and subjected to molecular biological processing to amplify and/or tag their nucleic acids with barcodes. The material from all the droplets can then be pooled for all cells and sequenced and the barcodes used to sort the sequences according to single droplets or cells. These methods can be used, for example, to sequence the genomes or transcriptomes of single cells in a massively parallel format. Alternatively, the cells, prior to encapsulation, can be bound with antibodies that are themselves labeled with tags relating the type of anybody they are. For example, a cocktail of tens or thousands of antibodies, each labeled with a tag relating the type of antibody it is, can be used to stain a collection of cells. The cells can then be dispensed and subjected to a barcoding protocol where the tags on the antibodies are additionally labeled with a tag/barcode relating the droplet/cell it originated from. This protocol is similar to the single cell sequencing protocol except that rather than labeling nucleic acids originating in the cell, it labels ones carried with the cell by the antibodies. The approach can be used to detect surface proteins in, for example, living or dead cells, or internal proteins with, for example, a fixation and permeabilization protocol. Similar techniques can be applied to individual viruses, macromolecular complexes, and proteins.

Synthesizing Polymers:

The ability to deliver droplets of defined composition to specific locations on a substrate is valuable for polymer synthesis. For example, in one embodiment, a first droplet can be dispensed to the substrate surface which includes a first monomer or polymer. A second droplet can then be dispensed to the same or an adjacent location, which includes a second monomer or polymer. The first and second droplets can then be incubated under and/or exposed to conditions sufficient for the contents of the first and second droplets to come into contact and for the first polymer or first monomer to form a covalent bond with the second polymer or second monomer, thereby generating a synthesized polymer. These steps can be repeated to increase the length of the polymer and thereby create polymers of defined sequence. In alternative embodiments, techniques like Gibson Assembly can be used for nucleic acid synthesis, which allows for the assembly of multiple components added at the same time, where overlap sequences are used to control the order in which the pieces are linked to synthesize a polymer of defined sequence. This can be used, for example to build DNA constructs for synthetic biology applications.

Screening Libraries:

Droplet based microfluidic techniques are valuable for screening libraries of compounds, enzymes, cells, etc., in which (or in connection with which) a reaction occurs that, normally, cannot be confined. For example, in directed evolution of enzymes, the product of a successful enzymatic reaction is a molecule that, generally, diffuses away from the enzyme catalyst. If many enzymes of varying catalytic power exist within the same solution, the product molecules mix, preventing the molecules produced by the action of one enzyme from being identified as having been produced by that enzyme. To evolve an enzyme, it is important to be able to select the best variant in a population (or a variant having a desired enzymatic activity relative to the other members of the population), which requires a method for measuring enzyme activity through product concentration. By enclosing each enzyme in a different droplet, it is possible to measure the activity of each variant independently by measuring the product concentration in each droplet. This can also be performed in the printed droplet format. For example, each enzyme variant can be localized in a droplet on the array and assayed for activity, and efficient enzymes (or those having a desired enzymatic activity) can be obtained by recovering the encapsulating droplets. Similar screens can be performed to test for therapeutic efficacy of a drug, e.g., a small molecule drug, or drug combination by evaluating its effects on cells in the droplets. Alternatively, by observing the droplets over time, it is also possible to screen based on time-dependent measurements, such as a peak production in product concentration at a specific time and/or for a specific duration.

Printing Microarrays:

In some embodiments, the methods, devices, and/or systems described herein can be used to synthesis oligos on an array for microarray production. For example, the substrate can be functionalized with a moiety to which nucleic acids can be attached. Then, by sequentially dispensing droplets of specific nucleic acids to individual spots on the substrate surface, the sequences can be attached to the substrate. The resolution of the spots will depend on the resolution with which the droplets can be printed, which is the on the order of micro to nanoscale features.

In Situ Sequencing:

In some embodiments, the methods, devices, and/or systems described herein can be used for in situ sequencing. In this approach, the goal is to correlate sequence information with the spatial location of the nucleic acids in the system, such as a nucleic acids originating within a cell in a tissue or tumor. This can be accomplished by printing onto such tissues droplets containing tags that relate the location of the tag. For example, the top left corner of a tissue can be printed with a tag that relates that the coordinate of the tag is at the top left corner, where different tag sequences, for example comprising nucleic acids, can be used for different coordinates on the tissue. The tags can be allowed to diffuse into the tissue, and a slice of the tissue can then be removed and disaggregated into small portions, such as single cells. This can then be repeated for the next slice, using tag sequences that relate the 3D position of each portion in the tissue. The portions, once disaggregated, can then be subjected to the single cell barcoding approach described above, where, in addition to sequences such as the genomic DNA and transcriptome RNA, the tags relating the location of that portion of material in the original sample are also barcoded. These materials can then be sequenced providing the sequences of the nucleic acids in the biological system and the location, by way of the tag sequence, that the portion originated from. This embodiment would allow, for example, the full genomic, transcriptional and proteomic information for every cell in the system to be obtained with a resolution equal to the droplet printing resolution and the slicing thickness.

Types of Discrete Entities

The composition and nature of the discrete entities, e.g., microdroplets, prepared and or utilized in connection with the disclosed methods may vary. For example, in some embodiments, a discrete entity may include one cell and not more than once cell. In other embodiments, a discrete entity may include a plurality of cells, i.e., two or more cells. In some aspects, discrete entities according to the present disclosure may include a nucleic acid or a plurality of nucleic acids. In some embodiments, as discussed above, discrete entities may include one or more solid and/or gel materials, such as one or more polymers.

In some embodiments, a surfactant may be used to stabilize the discrete entities, e.g., microdroplets. Accordingly, a microdroplet may involve a surfactant stabilized emulsion. Any convenient surfactant that allows for the desired reactions to be performed in the discrete entities, e.g., microdroplets, may be used. In other aspects, a discrete entity, e.g., a microdroplet, is not stabilized by surfactants or particles.

The surfactant used depends on a number of factors such as the oil and aqueous phases (or other suitable immiscible phases, e.g., any suitable hydrophobic and hydrophilic phases) used for the emulsions. For example, when using aqueous droplets in a fluorocarbon oil, the surfactant may have a hydrophilic block (PEG-PPO) and a hydrophobic fluorinated block (Krytox® FSH). If, however, the oil was switched to be a hydrocarbon oil, for example, the surfactant would instead be chosen so that it had a hydrophobic hydrocarbon block, like the surfactant ABIL EM90. In selecting a surfactant, desirable properties that may be considered in choosing the surfactant may include one or more of the following: (1) the surfactant has low viscosity; (2) the surfactant is immiscible with the polymer used to construct the device, and thus it doesn't swell the device; (3) biocompatibility; (4) the assay reagents are not soluble in the surfactant; (5) the surfactant exhibits favorable gas solubility, in that it allows gases to come in and out; (6) the surfactant has a boiling point higher than the temperature used for PCR (e.g., 95° C.); (7) the emulsion stability; (8) that the surfactant stabilizes drops of the desired size; (9)

that the surfactant is soluble in the carrier phase and not in the droplet phase; (10) that the surfactant has limited fluorescence properties; and (11) that the surfactant remains soluble in the carrier phase over a range of temperatures.

Other surfactants can also be envisioned, including ionic surfactants. Other additives can also be included in the oil to stabilize the discrete entities, e.g., microdroplets, including polymers that increase discrete entity, e.g., droplet, stability at temperatures above 35° C.

The discrete entities, e.g., microdroplets, described herein may be prepared as emulsions, e.g., as an aqueous phase fluid dispersed in an immiscible phase carrier fluid (e.g., a fluorocarbon oil or a hydrocarbon oil) or vice versa. The nature of the microfluidic channel (or a coating thereon), e.g., hydrophilic or hydrophobic, may be selected so as to be compatible with the type of emulsion being utilized at a particular point in a microfluidic work flow.

Emulsions may be generated using microfluidic devices as described in greater detail below. Microfluidic devices can form emulsions consisting of droplets that are extremely uniform in size. The microdroplet generation process may be accomplished by pumping two immiscible fluids, such as oil and water, into a junction. The junction shape, fluid properties (viscosity, interfacial tension, etc.), and flow rates influence the properties of the microdroplets generated but, for a relatively wide range of properties, microdroplets of controlled, uniform size can be generated using methods like T-junctions and flow focusing. To vary microdroplet size, the flow rates of the immiscible liquids may be varied since, for T-junction and flow focus methodologies over a certain range of properties, microdroplet size depends on total flow rate and the ratio of the two fluid flow rates. To generate an emulsion with microfluidic methods, the two fluids are normally loaded into two inlet reservoirs (syringes, pressure tubes) and then pressurized as needed to generate the desired flow rates (using syringe pumps, pressure regulators, gravity, etc.). This pumps the fluids through the device at the desired flow rates, thus generating microdroplet of the desired size and rate.

Adding Reagents to Discrete Entities

In practicing the subject methods, a number of reagents may be added to, i.e., incorporated into and/or encapsulated by, the discrete entities, e.g., microdroplets, in one or more steps (e.g., about 2, about 3, about 4, or about 5 or more steps). Such reagents may include, for example, amplification reagents, such as Polymerase Chain Reaction (PCR) reagents. The methods of adding reagents to the discrete entities, e.g., microdroplets, may vary in a number of ways. Approaches of interest include, but are not limited to, those described by Ahn, et al., Appl. Phys. Lett. 88, 264105 (2006); Priest, et al., Appl. Phys. Lett. 89, 134101 (2006); Abate, et al., PNAS, Nov. 9, 2010 vol. 107 no. 45 19163-19166; and Song, et al., Anal. Chem., 2006, 78 (14), pp 4839-4849; the disclosures of which are incorporated herein by reference.

For instance, a reagent may be added to a discrete entity, e.g., microdroplet, by a method involving merging a discrete entity, e.g., a microdroplet, with a second discrete entity, e.g., microdroplet, which contains the reagent(s). The reagent(s) that are contained in the second discrete entity may be added by any convenient methods, specifically including those described herein. This second discrete entity may be merged with the first discrete entity to create a discrete entity, e.g., a microdroplet, which includes the contents of both the first discrete entity and the second discrete entity.

One or more reagents may also, or instead, be added using techniques such as droplet coalescence, or picoinjection. In droplet coalescence, a target drop (i.e., the microdroplet) may be flowed alongside a microdroplet containing the reagent(s) to be added to the microdroplet. The two microdroplets may be flowed such that they are in contact with each other, but not touching other microdroplets. These drops may then be passed through electrodes or other aspects for applying an electrical field, wherein the electric field may destabilize the microdroplets such that they are merged together.

Reagents may also, or instead, be added using picoinjection. In this approach, a target drop (i.e., the microdroplet) may be flowed past a channel containing the reagent(s) to be added, wherein the reagent(s) are at an elevated pressure. Due to the presence of the surfactants, however, in the absence of an electric field, the microdroplet will flow past without being injected, because surfactants coating the microdroplet may prevent the fluid(s) from entering. However, if an electric field is applied to the microdroplet as it passes the injector, fluid containing the reagent(s) will be injected into the microdroplet. The amount of reagent added to the microdroplet may be controlled by several different parameters, such as by adjusting the injection pressure and the velocity of the flowing drops, by switching the electric field on and off, and the like.

In various aspects, one or more reagents may also, or instead, be added to a microdroplet by a method that does not rely on merging two droplets together or on injecting liquid into a drop. Rather, one or more reagents may be added to a microdroplet by a method involving the steps of emulsifying a reagent into a stream of very small drops, and merging these small drops with a target microdroplet. Such methods shall be referred to herein as "reagent addition through multiple-drop coalescence." These methods take advantage of the fact that due to the small size of the drops to be added compared to that of the target drops, the small drops will flow faster than the target drops and collect behind them. The collection can then be merged by, for example, applying an electric field. This approach can also, or instead, be used to add multiple reagents to a microdroplet by using several co-flowing streams of small drops of different fluids. To enable effective merger of the tiny and target drops, it is important to make the tiny drops smaller than the channel containing the target drops, and also to make the distance between the channel injecting the target drops from the electrodes applying the electric field sufficiently long so as to give the tiny drops time to "catch up" to the target drops. If this channel is too short, not all tiny drops will merge with the target drop, adding less reagent than desired. To a certain degree, this can be compensated for by increasing the magnitude of the electric field, which tends to allow drops that are farther apart to merge. In addition to making the tiny drops on the same microfluidic device, they can also, or instead, be made offline using another microfluidic drop maker or through homogenization and then injecting them into the device containing the target drops.

Accordingly, in some embodiments a reagent is added to a microdroplet by a method involving emulsifying the reagent into a stream of droplets, wherein the droplets are smaller than the size of the microdroplet; flowing the droplets together with the microdroplet; and merging a droplet with the microdroplet. The diameter of the droplets contained in the stream of droplets may vary ranging from about 75% or less than that of the diameter of the microdroplet, e.g., the diameter of the flowing droplets is about 75% or less than that of the diameter of the microdroplet, about 50% or less than that of the diameter of the microdroplet, about 25% or less than that of the diameter of the microdroplet, about 15% or less than that of the diameter of the microdroplet, about 10% or less than that of the diameter of the microdroplet, about 5% or less than that of the diameter of the microdroplet, or about 2% or less than that of the diameter of the microdroplet. In certain aspects, a plurality of flowing droplets may be merged with the microdroplet, such as 2 or more droplets, 3 or more, 4 or more, or 5 or more. Such merging may be achieved in a variety of ways, including but not limited to by applying an electric field, wherein the electric field is effective to merge the flowing droplet with the microdroplet.

A reagent, in another aspect, is added to a drop (e.g., a microdroplet) formed at an earlier time by enveloping the drop to which the reagent is be added (i.e., the "target drop") inside a drop containing the reagent to be added (the "target reagent"). In certain embodiments such a method is carried out by first encapsulating the target drop in a shell of a suitable hydrophobic phase, e.g., oil, to form a double emulsion. The double emulsion is then encapsulated by a drop containing the target reagent to form a triple emulsion. To combine the target drop with the drop containing the target reagent, the double emulsion is then burst open using any suitable method, including, but not limited to, applying an electric field, adding chemicals that destabilizes the droplet interface, flowing the triple emulsion through constrictions and other microfluidic geometries, applying mechanical agitation or ultrasound, increasing or reducing temperature, or by encapsulating magnetic particles in the drops that can rupture the double emulsion interface when pulled by a magnetic field.

Sorting

In practicing the methods of the present disclosure, one or more sorting steps may be employed. Sorting approaches of interest include, by are not necessarily limited to, approaches that involve the use of one or more sorters, e.g., sorters of a microfluidic device, which employ microfluidic valves, membrane valves, bifurcating channels, surface acoustic waves, and/or dielectrophoresis. Sorting approaches which may be utilized in connection with the disclosed methods, systems and devices also include those depicted in FIG. 2, and those described by Agresti, et al., PNAS vol. 107, no 9, 4004-4009; the disclosure of which is incorporated herein by reference. A population, e.g., a population of discrete entities, may be enriched by sorting, in that a population containing a mix of members having or not having a desired property may be enriched by removing those members that do not have the desired property, thereby producing an enriched population having the desired property.

In various embodiments, the subject methods include scanning, e.g., optically scanning one or more discrete entities, e.g., microdroplets, to facilitate sorting of the discrete entities. As such, in some embodiments, microfluidic devices or portions thereof, e.g., sorters, include one or more detectors, e.g., optical scanners. A variety of suitable optical scanners are known in the art. Such optical scanners may include, e.g., one or more optical fibers for applying excitation energy to one or more discrete entities. In some embodiments, a suitable optical scanner utilizes a laser light source directed into the back of an objective, and focused onto a microfluidic channel through which droplets flow, e.g., to excite fluorescent dyes within one or more discrete entities. Scanning one more discrete entities may allow one or more properties, e.g., size, shape, composition, of the scanned entities to be determined. Sorting may, in turn, be carried out based on the one or more properties. For example, sorting may be based on results obtained from an optical scan of one or more discrete entities.

Properties of discrete entities which may be detected include, but are not limited to, the size, viscosity, mass, buoyancy, surface tension, electrical conductivity, charge, magnetism, and/or presence or absence of one or more components, e.g., one or more detectable labels (e.g., one or more fluorescent labels). In certain aspects, sorting may be based at least in part upon the presence or absence of one or more cells in the microdroplet, e.g., one or more detectably labeled cells. In certain aspects, sorting may be based at least in part based upon the detection of the presence or absence of PCR amplification products.

Sorting may be applied at any suitable point in the disclosed methods. Moreover, two or more sorting steps may be applied to a population of discrete entities or types thereof, e.g., microdroplets, e.g., about 2 or more sorting steps, about 3 or more, about 4 or more, or about 5 or more, etc. When a plurality of sorting steps is applied, the steps may be substantially identical or different in one or more ways (e.g., sorting based upon a different property, sorting using a different technique, and the like).

Moreover, discrete entities, e.g., droplets, may be purified prior to, or after, any sorting step. In one embodiment a droplet may be purified as follows: a majority of the fluid in the drop is replaced it with a purified solution, without removing any discrete reagents that may be encapsulated in the drop, such a cells or beads. The microdroplet is first injected with a solution to dilute any impurities within it. The diluted microdroplet is then flowed through a microfluidic channel on which an electric field is being applied using electrodes. Due to the dielectrophoretic forces generated by the field, as the cells or other discrete reagents pass through the field they will be displaced in the flow. The drops are then split, so that all the objects end up in one microdroplet. Accordingly, the initial microdroplet has been purified, in that the contaminants may be removed while the presence and/or concentration of discrete reagents, such as beads or cells, which may be encapsulated within the droplet, are maintained in the resulting microdroplet.

Microdroplets may be sorted based on one or more properties. Properties of interest include, but are not limited to, the size, viscosity, mass, buoyancy, surface tension, electrical conductivity, charge, magnetism, and/or presence or absence of one or more components, e.g., one or more detectable labels. In certain aspects, sorting may be based at least in part upon the presence or absence of one or more cells in the microdroplet, e.g., one or more detectably labeled cells. In certain aspects, sorting may be based at least in part based upon the detection of the presence or absence of PCR amplification products.

Sorting may be employed, for example, to remove discrete entities, e.g., microdroplets, in which no cells are present. Encapsulation may result in one or more discrete entities, e.g., microdroplets, including a majority of the discrete entities, e.g., microdroplets, in which no cell is present. If such empty drops were left in the system, they would be processed as any other drop, during which reagents and time would be wasted. To achieve the highest speed and efficiency, these empty drops may be removed with droplet sorting. For example, a drop maker may operate close to the dripping-to-jetting transition such that, in the absence of a cell, drops of a first size, e.g., 8 µm, are formed; by contrast, when a cell is present the disturbance created in the flow will trigger the breakup of the jet, forming drops of a second size, e.g., 25 µm in diameter. The device may thus produce a bi-disperse population of empty drops of a first size, e.g., 8 µm, and single-cell containing drops of a second size, e.g., 25 µm, which may then be sorted by size using, e.g., a hydrodynamic sorter to recover only the, single-cell containing drops of the second, e.g., larger, size.

Sorters of the subject embodiments may be active or passive sorters. Passive sorters of interest include hydrodynamic sorters, which sort discrete entities, e.g., microdroplets, into different channels according to size, based on the different ways in which small and large drops travel through the microfluidic channels. Also of interest are bulk sorters, a simple example of which is a tube containing drops of different mass in a gravitational field. By centrifuging, agitating, and/or shaking the tube, lighter drops that are more buoyant will naturally migrate to the top of the container. Drops that have magnetic properties could be sorted in a similar process, except by applying a magnetic field to the container, towards which drops with magnetic properties will naturally migrate according to the magnitude of those properties. A passive sorter as used in the subject methods may also involve relatively large channels that will sort large numbers of drops simultaneously based on their flow properties. Additionally, in some embodiments, sorting is carried out via activation of one or more valves, e.g., microfluidic valves.

Picoinjection can also be used to change the electrical properties of the drops. This could be used, for example, to change the conductivity of the drops by adding ions, which could then be used to sort them, for example, using dielectrophoresis. Alternatively, picoinjection can also be used to charge the drops. This could be achieved by injecting a fluid into the drops that is charged, so that after injection, the drops would be charged. This would produce a collection of drops in which some were charged and others not, and the charged drops could then be extracted by flowing them through a region of electric field, which will deflect them based on their charge amount. By injecting different amounts of liquid by modulating the piocoinjection, or by modulating the voltage to inject different charges for affixed injection volume, the final charge on the drops could be adjusted, to produce drops with different charge. These would then be deflected by different amounts in the electric field region, allowing them to be sorted into different containers.

Improved Sorting Architecture for High-Speed Sorting of Microdroplets

In some embodiments, the present disclosure provides microfluidic devices with an improved sorting architecture, which facilitates the high-speed sorting of discrete entities, e.g., microdroplets. This sorting architecture may be used in connection with the microdroplet printer embodiments described herein or in any other suitable application where high-speed sorting of microdroplets is desired. Related methods and systems are also described. For example, in some embodiments, microfluidic devices are provided which include at least an inlet channel; a first outlet channel in fluid communication with the inlet channel; a second outlet channel in fluid communication with the inlet channel; a dividing wall separating the first outlet channel from the second outlet channel, wherein the dividing wall comprises a first proximal portion having a height which is less than the height of the inlet channel and a second distal portion having a height which is equal to or greater than the height of the inlet channel.

In some embodiments, the height of the first proximal portion of the dividing wall is from about 10% to about 90% of the height of the inlet channel, e.g., from about 20% to about 80%, from about 30% to about 70%, from about 40% to about 60%, or about 50% of the height of the inlet channel.

In some embodiments the height of the first proximal portion of the dividing wall is from about 10% to about 20%, from about 20% to about 30%, from about 30% to about 40%, from about 40% to about 50%, from about 50% to about 60%, from about 60% to about 70%, or from about 80% to about 90% of the height of the inlet channel.

In some embodiments, the length of the proximal portion of the dividing wall is equal to or greater than the diameter of a microdroplet as described herein, e.g., a microdroplet to be sorted using a microfluidic device as described herein. For example, in some embodiments, the length of the proximal portion of the dividing wall is from about 1× to about 100× the diameter of a microdroplet as described herein, e.g., from about 1× to about 10×, from about 10× to about 20×, from about 20× to about 30×, from about 30× to about 40×, from about 40× to about 50×, from about 50× to about 60×, from about 60× to about 70×, from about 70× to about 80×, from about 80× to about 90×, or from about 90× to about 100× the diameter of a microdroplet as described herein.

In some embodiments a microfluidic device according to the present disclosure includes an electrode, e.g., a liquid electrode, configured to selectively apply an electrical field in an inlet channel of the microfluidic device upstream of the dividing wall to effect sorting of one or more microdroplets.

In some embodiments, liquid electrodes include liquid electrode channels filled with a conducting liquid (e.g. salt water or buffer) and situated at positions in the microfluidic device where an electric field is desired. In particular embodiments, the liquid electrodes are energized using a power supply or high voltage amplifier. In some embodiments, the liquid electrode channel includes an inlet port so that a conducting liquid can be added to the liquid electrode channel. Such conducting liquid may be added to the liquid electrode channel, for example, by connecting a tube filled with the liquid to the inlet port and applying pressure. In particular embodiments, the liquid electrode channel also includes an outlet port for releasing conducting liquid from the channel.

In alternative embodiments, a solid electrode prepared from any suitable conductive material may be utilized.

As described herein, microfluidic devices according to the present disclosure may include a moat salt solution (to generate the field gradient used for dielectrophoretic deflection and to limit stray fields that can cause unintended droplet merger) provided in suitable channels.

Accordingly, a microfluidic device having a gapped dividing wall is provided which facilitates high speed sorting as described in greater detail in the Experimental section. The gapped dividing wall of the present disclosure in combination with one or more detectors as described herein, and one or more electrodes as described herein facilitate the high-speed sorting of microdroplets.

Printing Cell Layers

Figure 3:
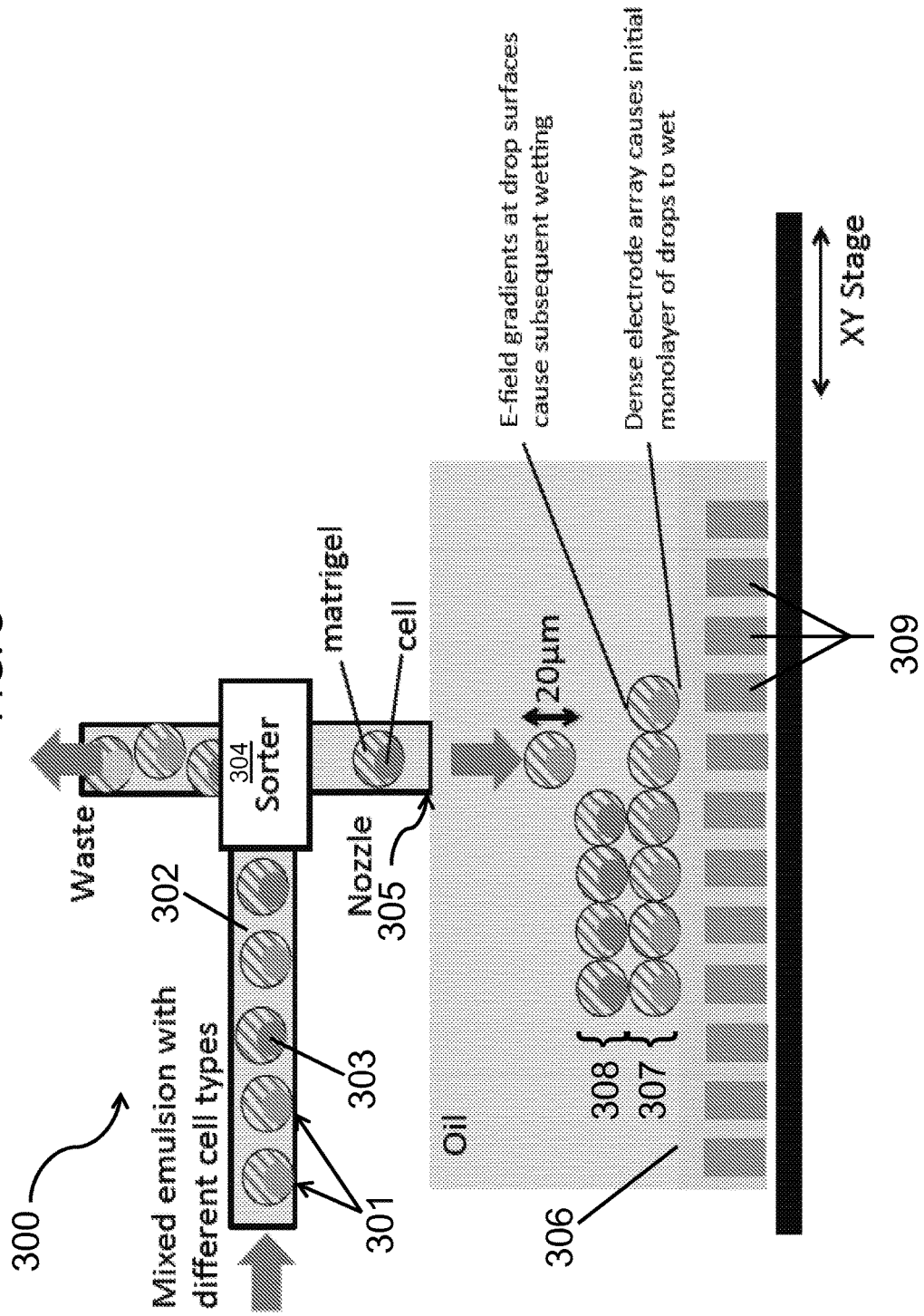
FIG. 3 provides a simplified representation of one type of microfluidic system and an associated method of the present disclosure. The application depicted is the delivery of discrete entities including cells to a substrate.

In some embodiments, the present disclosure provides methods and related devices and systems for printing one or more tissues and/or cell layers. FIG. 3 depicts a non-limiting, simplified representation of one type of microfluidic system and method of the present disclosure which may be utilized in the printing of one or more tissues or cell layers. FIG. 3 illustrates the delivery of discrete entities including cells to a substrate. In one such method, discrete entities, e.g., droplets 301, are prepared using a device, e.g., a microfluidic device 300, and a carrier fluid 302 to produce a mixed emulsion including the discrete entities. Discrete entities, e.g., droplets 301, as shown in FIG. 3 may include one or more reagent, e.g., a reagent which facilitates cell growth and/or a cell culture media component and/or a cell culture substrate, e.g., a matrigel, and different types of cells 303. The subject method may include encapsulating, e.g., encapsulating by fully containing therein, one or more cells in a discrete entity.

In some aspects of printing tissues, a mixed emulsion is flowed through a sorter 304 which sorts discrete entities 301 of the mixed emulsion based on one or more of their characteristics. As is shown in FIG. 3, the sorter 304 may be configured to detect and/or separate discrete entities 301 containing cells 303 based on cell type. For example, a sorter may be configured to separate a first type of discrete entity, e.g., a droplet type containing one or more cell of interest, and a second type, e.g., a type not containing one or more cell of interest. As such, a sorter 304 may produce a first fraction, e.g., a fluid containing carrier fluid and discrete entities having a first type, e.g., one or more type of interest, and a second fraction, e.g., a fluid containing carrier fluid and discrete entities having a second type, e.g., one or more type not of interest. The sorter 304 may also be configured to direct the first fraction toward a portion of a microfluidic device having a delivery orifice 305, e.g., a nozzle having a delivery orifice 305, for delivery to a substrate and the second fraction toward a waste container or outlet. Alternatively, the second fraction may be recycled by reintroducing it upstream of the sorter 504. In some embodiments, a nozzle or a portion thereof, e.g., a delivery orifice 305, may be positioned from about 1 µm to about 200 µm, such as from about 5 µm to about 100 µm, or from about 10 µm to about 50 µm, inclusive, such as about 20 µm away from a target such as surface 306 of a substrate or a previously deposited layer of discrete entities.

In some variations, the methods may include affixing a first layer 307 of discrete entities, e.g., discrete entities including a first cell type, to a substrate surface 306 of a substrate and one or more other layers, e.g., a second layer 308 of discrete entities, e.g., discrete entities including a second cell type, to the first layer of discrete entities. In various embodiments, a first layer 307 of discrete entities can be applied to a substrate surface 306 before, or contemporaneously with, a second layer 308. Aspects of the methods may also include affixing one or more additional layers of discrete entities, e.g., discrete entities encapsulating cells, to one or more previously affixed layer. For example, the subject methods may include affixing between 1 and 10 million, inclusive, such as between 10 and 1 million or between 100 and 10,000, inclusive, additional layers of discrete entities. Accordingly, the methods may include providing a layered structure, e.g., a tissue, by repeated layering of discrete entity layers. It should be noted that each layer may include discrete entities of a specific type or a plurality of discrete entities of different types, e.g., discrete entities having varying compositions or components. For example, first layer 307 and/or a second layer 308 may include a plurality of discrete entities including different cell types, e.g., a first discrete entity including a first cell type and a second discrete entity including a second different cell type than the first discrete entity. In other words, each layer may include either a homogenous or heterogeneous population of discrete entities, e.g., microdroplets.

In some embodiments, substrates or portions thereof, e.g., substrate surfaces, include one or more electrodes 309. Such electrodes 309 may be used to apply a force, to thereby cause a first layer 307, e.g., initial layer, of discrete entities to affix to, e.g., wet, a substrate or a substrate surface 306 thereof. Once a first layer 307, e.g., initial layer, of discrete entities is applied, electric field gradients at drop surfaces of discrete entities of the first layer 307 may cause subsequent discrete entities, e.g., discrete entities of a second layer 308, to affix to, e.g., wet, the first layer 307.

Detecting Cells

In some embodiments, the subject methods involve detecting the presence and/or absence of one or more cells or one or more other characteristics, such as type and/or size, of one or more subset of cells (e.g., tumor cells) in one or more discrete entities, e.g., droplets, while in a mixed emulsion and/or before, during or after the discrete entity is affixed to a layer of discrete entities, a substrate, or a portion thereof, e.g., a substrate surface, as described herein. In some embodiments, a sorter of a microfluidic device is utilized for detecting one or more characteristics of cells encapsulated within discrete entities.

Aspects of the disclosed methods may include detecting one or more characteristics of cells, e.g., one or more cells within discrete entities affixed to a substrate, at a plurality of time points, e.g., a plurality of equally-spaced time points. The methods may also include detecting one or more characteristics of one or more cells continuously over a period of time, such as detecting a component of the one or more cells, and/or a product of the one or more cells. Embodiments of the methods may further include recovering, e.g., recovering by extracting, from a discrete entity one or more cells, a component of one or more cells, e.g., deoxyribonucleic acid (DNA), and/or a product of one or more cells. In various embodiments, the methods may include sequencing DNA recovered from one or more cells.

Aspects of the disclosed methods may include incorporating into a mixed emulsion discrete entities having one or more cells obtained from a biological sample.

As used herein, the term "biological sample" encompasses a variety of sample types obtained from a variety of sources, which sample types contain biological material. For example, the term includes biological samples obtained from a mammalian subject, e.g., a human subject, and biological samples obtained from a food, water, or other environmental source, etc. The definition encompasses blood and other liquid samples of biological origin, as well as solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, cells, serum, plasma, biological fluid, and tissue samples. "Biological sample" includes cells; biological fluids such as blood, cerebrospinal fluid, semen, saliva, and the like; bile; bone marrow; skin (e.g., skin biopsy); and antibodies obtained from an individual.

As is described more fully herein, in various aspects the subject methods may be used to detect a variety of components from cells, such as cells from biological samples. Components of interest include, but are not necessarily limited to, cells (e.g., circulating cells and/or circulating tumor cells), polynucleotides (e.g., DNA and/or RNA), polypeptides (e.g., peptides and/or proteins), and many other components that may be present in a biological sample.

"Polynucleotides" or "oligonucleotides" as used herein refer to linear polymers of nucleotide monomers, and may be used interchangeably. Polynucleotides and oligonucleotides can have any of a variety of structural configurations, e.g., be single stranded, double stranded, or a combination of both, as well as having higher order intra- or intermolecular secondary/tertiary structures, e.g., hairpins, loops, triple stranded regions, etc. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, *Human Molecular Genetics* 2 (Wiley-Liss, New York, 1999).

The terms "polypeptide," "peptide," and "protein," used interchangeably herein, refer to a polymeric form of amino acids of any length. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-3559 is used.

In certain aspects, methods are provided for counting and/or genotyping cells, including normal cells or tumor cells. A feature of such methods is the use of microfluidics.

According to some embodiments of the subject methods, cells, e.g., cells in discrete entities in an emulsion and/or affixed to a substrate, a biological sample (e.g., whole blood) may be recovered from a subject using any convenient method, e.g., by applying a needle and/or a syringe. The biological sample may then be processed to remove components other than cells using, for example, processing steps such as centrifugation, filtration, and the like.

Each cell in the biological sample, or a subset thereof, may then be encapsulated into a discrete entity, e.g., a droplet, using a microfluidic device. Methods and devices which may be utilized in the encapsulating of a component from a biological sample are described in PCT Publication No. WO 2014/028378, the disclosure of which is incorporated by reference herein in its entirety and for all purposes. Encapsulation approaches of interest also include, but are not limited to, hydrodynamically-triggered drop formation and those described by Link, et al., *Phys. Rev. Lett.* 92, 054503 (2004), the disclosure of which is incorporated herein by reference. Other methods of encapsulating cells into droplets may also be applied. Where desired, the cells may be stained with one or more antibodies and/or probes prior to encapsulating them into drops.

One or more lysing agents may also be added to the discrete entities, e.g., droplets, containing a cell, under conditions in which the cell(s) may be caused to burst, thereby releasing their genomes. The lysing agents may be added after the cells are encapsulated into discrete entities, e.g., microdroplets. Any convenient lysing agent may be employed, such as proteinase K or cytotoxins. In particular embodiments, cells may be co-encapsulated in drops with lysis buffer containing detergents such as Triton X100 and/or proteinase K. The specific conditions in which the cell(s) may be caused to burst will vary depending on the specific lysing agent used. For example, if proteinase K is incorporated as a lysing agent, the discrete entities, e.g., droplets, may be heated to about 37-60° C. for about 20 min to lyse the cells and to allow the proteinase K to digest cellular proteins, after which they may be heated to about 95° C. for about 5-10 min to deactivate the proteinase K.

In certain aspects, cell lysis may also, or instead, rely on techniques that do not involve addition of lysing agent. For example, lysis may be achieved by mechanical techniques that may employ various geometric features to effect piercing, shearing, abrading, etc. of cells. Other types of mechanical breakage such as acoustic techniques may also be used. Further, thermal energy can also be used to lyse cells. Any convenient methods of effecting cell lysis may be employed in the methods described herein.

One or more primers may be introduced into the discrete entities, e.g., droplets, for each of the genes, e.g., oncogenes, to be detected. Hence, in certain aspects, primers for all target genes, e.g., oncogenes, may be present in the discrete entity, e.g., droplet, at the same time, thereby providing a multiplexed assay. The discrete entities, e.g., droplets, may be temperature-cycled so that discrete entities, e.g., droplets, containing cancerous cells, for example, will undergo PCR. During this time, only the primers corresponding to genes, e.g., oncogenes, present in the genome will induce amplification, creating many copies of these genes, e.g., oncogenes, in the discrete entity, e.g., droplet. Detecting the presence of these PCR products may be achieved by a variety of ways, such as by using FRET, staining with an intercalating dye, or attaching them to a bead. More information on the different options for such detection is also provided herein. The discrete entity, e.g., droplet, may be optically probed, e.g., probed using a laser, to detect the PCR products. Optically probing the discrete entity, e.g., droplet, may involve counting the number of target cells, e.g., tumor cells, present in the initial population, and/or to allow for the identification the target, e.g., oncogenes, present in each cell, e.g., tumor cell.

Aspects of the subject methods may be used to determine whether a biological sample contains particular cells of interest, e.g., tumor cells, or not. In certain aspects, the subject methods may include quantifying the number of cells of interest, e.g., tumor cells, present in a biological sample. Quantifying the number of cells of interest, e.g., tumor cells, present in a biological sample may be based at least in part on the number of discrete entities, e.g., droplets, in which PCR amplification products were detected. For example, discrete entities, e.g., droplets, may be produced under conditions in which the majority of discrete entities, e.g., droplets, are expected to contain zero or one cells. Those discrete entities, e.g., droplets, that do not contain any cells may be removed, using techniques described more fully herein. After performing the PCR steps outlined above, the total number of discrete entities, e.g., droplets, that are detected to contain PCR products may be counted, so as to quantify the number of cells of interest, e.g., tumor cells, in the biological sample. In certain aspects, the methods may also include counting the total number of discrete entities, e.g., droplets, so as to determine the fraction or percentage of cells from the biological sample that are cells of interest, e.g., tumor cells.

PCR

As described above, in practicing the subject methods, a PCR-based assay, e.g., quantitative PCR (qPCR), may be used to detect the presence of certain genes of interest, e.g., oncogene(s), present in discrete entities or one or more components thereof, e.g., cells encapsulated therein. Such assays can be applied to discrete entities within a microfluidic device or a portion thereof and/or while the discrete entities are affixed to a substrate or a portion thereof, e.g., a substrate surface. The conditions of such PCR-based assays may include detecting nucleic acid amplification over time and may vary in one or more ways.

For instance, the number of PCR primers that may be added to a microdroplet may vary. The term "primer" may refer to more than one primer and may refer to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include, e.g., the presence of four different deoxyribonucleoside triphosphates and a polymerization-inducing agent such as DNA polymerase or reverse transcriptase, in a suitable buffer ("buffer" which includes substituents which are cofactors, or which affect pH, ionic strength, etc.), and at a suitable temperature. The primer may be single-stranded for maximum efficiency in amplification.

The complement of a nucleic acid sequence as used herein may refer to an oligonucleotide which, when aligned with the nucleic acid sequence such that the 5' end of one sequence is paired with the 3' end of the other, is in "antiparallel association." Complementarity need not be perfect; stable duplexes may contain mismatched base pairs or unmatched bases. Duplex stability can be determined by empirically considering a number of variables including, for example, the length of the oligonucleotide, percent concentration of cytosine and guanine bases in the oligonucleotide, ionic strength, and incidence of mismatched base pairs.

The number of PCR primers that may be added to a microdroplet may range from about 1 to about 500 or more, e.g., about 2 to 100 primers, about 2 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more.

Such primers may contain primers for one or more gene of interest, e.g. oncogenes. The number of primers for genes of interest that are added may be from about one to 500, e.g., about 1 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more.

Such primers and/or reagents may be added to a discrete entity, e.g., a microdroplet, in one step, or in more than one step. For instance, the primers may be added in two or more steps, three or more steps, four or more steps, or five or more steps. Regardless of whether the primers are added in one step or in more than one step, they may be added after the addition of a lysing agent, prior to the addition of a lysing agent, or concomitantly with the addition of a lysing agent. When added before or after the addition of a lysing agent, the PCR primers may be added in a separate step from the addition of a lysing agent. In some embodiments, the discrete entity, e.g., a microdroplet, may be subjected to a dilution step and/or enzyme inactivation step prior to the addition of the PCR reagents. Exemplary embodiments of such methods are described in PCT Publication No. WO 2014/028378, the disclosure of which is incorporated by reference herein in its entirety and for all purposes.

Once primers have been added to a discrete entity, e.g., a microdroplet, the discrete entity, e.g., a microdroplet, may be incubated under conditions allowing for PCR. The discrete entity, e.g., a microdroplet, may be incubated on the same microfluidic device as was used to add the primer(s), or may be incubated on a separate device. In certain embodiments, incubating the discrete entity, e.g., a microdroplet, under conditions allowing for PCR amplification is performed on the same microfluidic device used to encapsulate the cells and/or lyse the cells. Incubating the microdroplets may take a variety of forms. In certain aspects, the drops containing the PCR mix may be flowed through a channel that incubates the droplets under conditions effective for PCR. Flowing the microdroplets through a channel may involve a channel that snakes over various temperature zones maintained at temperatures effective for PCR. Such channels may, for example, cycle over two or more temperature zones, wherein at least one zone is maintained at about 65° C. and at least one zone is maintained at about 95° C. As the drops move through such zones, their temperature cycles, as needed for PCR. The precise number of zones, and the respective temperature of each zone, may be determined to achieve the desired PCR amplification.

In other embodiments, incubating the microdroplets may involve the use of a "Megadroplet Array", for example as described in PCT Publication No. WO 2014/028378, the disclosure of which is incorporated by reference herein in its entirety and for all purposes. In such a device, an array of hundreds, thousands, or millions of traps indented into a channel (e.g., a PDMS channel) sit above a thermal system. The channel may be pressurized, thereby preventing gas from escaping. The height of the microfluidic channel is smaller than the diameter of the discrete entities, e.g., drops, causing discrete entities to adopt a flattened pancake shape. When a discrete entity flows over an unoccupied indentation, it adopts a lower, more energetically favorable, radius of curvature, leading to a force that pulls the discrete entity entirely into the trap. By flowing discrete entities as a close pack, it is ensured that all traps on the array are occupied. The entire device may be thermal cycled using a heater.

In certain aspects, the heater includes a Peltier plate, heat sink, and control computer. The Peltier plate allows for the heating or cooling of the chip above or below room temperature by controlling the applied current. To ensure controlled and reproducible temperature, a computer may monitor the temperature of the array using integrated temperature probes, and may adjust the applied current to heat and cool as needed. A metallic (e.g. copper) plate allows for uniform application of heat and dissipation of excess heat during cooling cycles, enabling cooling from about 95° C. to about 60° C. in under about one minute.

Methods of the disclosure may also include introducing one or more probes to the microdroplet. As used herein with respect to nucleic acids, the term "probe" refers to a labeled oligonucleotide which forms a duplex structure with a sequence in the target nucleic acid, due to complementarity of at least one sequence in the probe with a sequence in the target region. Probes of interest include, but are not limited to, TaqMan® probes (e.g., as described in Holland, P. M.; Abramson, R. D.; Watson, R.; Gelfand, D. H. (1991). "Detection of specific polymerase chain reaction product by utilizing the 5'-3' exonuclease activity of *Thermus aquaticus* DNA polymerase". PNAS, 88 (16): 7276-7280).

In some embodiments of the subject methods, an RT-PCR based assay is used to detect the presence of certain transcripts of interest, e.g., oncogene(s), present in cells. In such embodiments, reverse transcriptase and any other reagents necessary for cDNA synthesis are added to the discrete entity, e.g., microdroplet, in addition to the reagents used to carry out PCR described herein (collectively referred to as the "RT-PCR reagents"). The RT-PCR reagents are added to the discrete entity, e.g., microdroplet, using any of the methods described herein. Once reagents for RT-PCR have been added to a discrete entity, e.g., microdroplet, the microdroplet may be incubated under conditions allowing for reverse transcription followed by conditions allowing for PCR as described herein. The microdroplet may be incubated on the same microfluidic device as was used to add the RT-PCR reagents, or may be incubated on a separate device. In certain embodiments, incubating the microdroplet under conditions allowing for RT-PCR is performed on the same microfluidic device used to encapsulate the cells and lyse the cells.

In certain embodiments, the reagents added to the microdroplet for RT-PCR or PCR further includes a fluorescent DNA probe capable of detecting real-time RT-PCR or PCR products. Any suitable fluorescent DNA probe can be used including, but not limited to SYBR Green, TaqMan®, Molecular Beacons and Scorpion probes. In certain embodiments, the reagents added to the microdroplet include more than one DNA probe, e.g., two fluorescent DNA probes, three fluorescent DNA probes, or four fluorescent DNA probes. The use of multiple fluorescent DNA probes allows for the concurrent measurement of RT-PCR or PCR products in a single reaction.

Furthermore, examples of PCR-based assays of interest which may be employed according to the subject embodiments, include, but are not limited to, quantitative PCR (qPCR), quantitative fluorescent PCR (QF-PCR), multiplex fluorescent PCR (MF-PCR), real time PCR (RT-PCR), single cell PCR, PCR-RFLP/RT-PCR-RFLP, hot start PCR, nested PCR, in situ polony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA).

Multiplexing

In various aspects of the subject methods, multiple biomarkers may be detected and analyzed for a particular discrete entity or one or more components thereof, e.g., cell(s) encapsulated therein. Biomarkers detected may include, but are not limited to, one or more proteins, transcripts and/or genetic signatures in a cell's genome or combinations thereof. With standard fluorescence based detection, the number of biomarkers that can be simultaneously interrogated may be limited to the number of fluorescent dyes that can be independently visualized within each discrete entity, e.g., microdroplet. In certain embodiments, the number of biomarkers that can be individually detected within a particular discrete entity, e.g., microdroplet can be increased. For example, this may be accomplished by segregation of dyes to different parts of the discrete entity, e.g., microdroplet. In particular embodiments, beads (e.g. LUMINEX® beads) conjugated with dyes and probes (e.g., nucleic acid or antibody probes) may be encapsulated in the discrete entity, e.g., microdroplet to increase the number of biomarkers analyzed. In another embodiment, fluorescence polarization may be used to achieve a greater number of detectable signals for different biomarkers for a single cell. For example, fluorescent dyes may be attached to various probes and the discrete entity, e.g., microdroplet, may be visualized under different polarization conditions. In this way, the same colored dye can be utilized to provide a signal for different probe targets for a single cell. The use of fixed and/or permeabilized cells also may allow for increased levels of multiplexing. For example, labeled antibodies may be used to target protein targets localized to cellular components while labeled PCR and/or RT-PCR products are free within a discrete entity, e.g., microdroplet. This allows for dyes of the same color to be used for antibodies and for amplicons produced by RT-PCR.

Detecting PCR Products

The manner in which PCR products can be detected according to the subject methods may vary. For example, if the goal is to count the number of a particular cell type, e.g., tumor cells, present in a population, this may be achieved by using a simple binary assay in which SybrGreen, or any other stain and/or intercalating stain, is added to each discrete entity, e.g., microdroplet, so that in the event a characterizing gene, e.g., an oncogene, is present and PCR products are produced, the discrete entity, e.g., microdroplet, will become fluorescent. The change in fluorescence may be due to fluorescence polarization. The detection component may include the use of an intercalating stain (e.g., SybrGreen).

A variety of different detection components may be used in practicing the subject methods, including using one or more fluorescent dyes. Such fluorescent dyes may be divided into families, such as fluorescein and its derivatives; rhodamine and its derivatives; cyanine and its derivatives; coumarin and its derivatives; Cascade Blue and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like. Descriptions of fluorophores and their use, can be found in, among other places, R. Haugland, Handbook of Fluorescent Probes and Research Products, 9th ed. (2002), Molecular Probes, Eugene, Oreg.; M. Schena, Microarray Analysis (2003), John Wiley & Sons, Hoboken, N.J.; Synthetic Medicinal Chemistry 2003/2004 Catalog, Berry and Associates, Ann Arbor, Mich.; G. Hermanson, Bioconjugate Techniques, Academic Press (1996); and Glen Research 2002 Catalog, Sterling, Va.

In practicing the subject methods, therefore, a component may be detected based upon, for example, a change in fluorescence. In certain aspects, the change in fluorescence is due to fluorescence resonance energy transfer (FRET). In this approach, a special set of primers may be used in which the 5' primer has a quencher dye and the 3' primer has a fluorescent dye. These dyes can be arranged anywhere on the primers, either on the ends or in the middles. Because the primers are complementary, they will exist as duplexes in solution, so that the emission of the fluorescent dye will be quenched by the quencher dye, since they will be in close proximity to one another, causing the solution to appear dark. After PCR, these primers will be incorporated into the long PCR products, and will therefore be far apart from one another. This will allow the fluorescent dye to emit light, causing the solution to become fluorescent. Hence, to detect if a particular target gene, e.g., oncogene, is present, one may measure the intensity of the discrete entity, e.g., droplet, at the wavelength of the fluorescent dye. To detect if different target genes, e.g., oncogenes, are present, this would be done with different colored dyes for the different primers. This would cause the discrete entity, e.g., droplet, to become fluorescent at all wavelengths corresponding to the primers of the target genes, e.g., oncogenes, present in the cell.

In some embodiments, the disclosed methods may include a step of encapsulating or incorporating unique identifier molecules, e.g., nucleic acid barcodes, into a plurality of discrete entities, e.g., droplets, such that each discrete entity of the plurality of discrete entities comprises a different set of unique identifier molecules. Alternatively, or in addition, the disclosed methods may include a step of incorporating a unique identifier molecule into each molecule within a particular discrete entity, e.g., droplet.

Printing Combined with Separation Techniques

In some embodiments, the printing methods described herein can be combined with separation techniques to achieve finer sensitivity for detecting and analyzing the contents of a discrete entity. For example, discrete entities, e.g., droplets, containing cells can be printed to a substrate and, for example, solidified by gelling them. The carrier oil can then be removed and replaced with another material, such as a gel matrix appropriate for separation. The substrate can then be incubated under conditions appropriate to lyse and separate the contents of the cells, such as by applying an electric current to induce electrophoretic migration of molecules through the matrix in a specific direction, such as perpendicular to the plane of the substrate or in the plane of the substrate. Such separation can also be performed in two or three dimensions, to achieve planar or cubic separations.

The spacing of the discrete entities, e.g., droplets, on the printed substrate can be selected so as to provide adequate distance for the separation of the materials. The separated materials can then be detected using a variety of techniques, such as blotting techniques such as western, southern, and northern blotting, or optical or spectrographic techniques, such as Raman spectroscopy or mass spectrometry, to name a few examples. This enables the contents of the cells to be analyzed with higher resolution by preforming a separation based on biochemical properties prior to the analysis step, which is an important aspect of sensitive measurement techniques like liquid chromatography mass spectrometry. The same concepts can apply to other printed entities, such as droplets encapsulating cell-free transcript and translation reagents or other biological reagents, as well as to particles and other liquid droplets in which such two-step separation and analysis techniques would be valuable. For example, such methods can be used in synthetic biology screens by printing droplets encapsulating cells or cell-free extracts expressing a target pathway and then using the separation procedure to separated important molecules in the medium prior to performing the spectrographic or mass spectrometric analysis.

Accordingly, in some embodiments the present disclosure provides a method, wherein the method includes printing discrete entities to a substrate surface using any suitable method described herein; replacing the carrier fluid with a material suitable for molecular separation, such as polyacrylamide, agarose, etc.; incubating the printed substrate under conditions sufficient to induce molecular separation of the contents of the discrete entities into the surrounding separation material (e.g., by applying an electric current); and analyzing the separated contents of the discrete entities in the material. In some such embodiments, the discrete entities include droplets including biological materials such as, for example, proteins, nucleic acids, cells, viruses, etc. In some embodiments, the separation is achieved using gel electrophoresis. In some embodiments, the method may be used to perform blotting experiments on the discrete entities and their contents such as southern, northern, and western blotting. In some embodiments, the separated materials are analyzed using mass spectrometry such as, for example, MALDI, NIMS, etc. In some embodiments, the materials are separated in more than one dimension by changing the direction of the separating force. In some embodiments, the analysis of the separated materials uses 3D imaging or other technique, such as confocal microscopy or layer-by-layer MALDI-MS to analyze the separated materials in the 3D network of the separation material.

Devices

As indicated above, embodiments of the disclosed subject matter employ systems and/or devices including microfluidic devices. Devices of the subject disclosure include all those described above in association with the subject methods. Microfluidic devices of this disclosure may be characterized in various ways.

In some aspects, for example, systems and/or devices are provided which include one or more discrete entity, e.g., droplet, printers. Discrete entity printers may include one or more microfluidic device, such as a microfluidic device including one or more discrete entity makers, e.g., droplet makers, configured to generate discrete entities, e.g., droplets, as described herein, and/or one or more flow channels. In some aspects, the one or more flow channels are operably connected, e.g., fluidically connected, to the one or more droplet makers and/or are configured to receive one or more droplets therefrom. By "operably connected" and "operably coupled", as used herein, is meant connected in a specific way (e.g., in a manner allowing fluid, e.g., water, to move and/or electric power to be transmitted) that allows a disclosed system or device and its various components to operate effectively in the manner described herein.

Aspects of the disclosed devices also include one or more delivery orifice, such as a delivery orifice fluidically connected to one or more flow channels. In some embodiments, delivery orifices include an opening, e.g., a circular or oblong opening, through which one or more discrete entities may pass. In some embodiments, openings of delivery orifices are defined by a rim of a device or a portion thereof, e.g., a nozzle, such as a positionable nozzle. Delivery orifices, as included in the subject embodiments, may have any of the same dimensions, e.g., a cross-sectional dimension, as the flow channels described herein, or may have different dimensions.

A delivery orifice as described herein, e.g., a delivery orifice of a microfluidic nozzle as described herein, will generally have dimensions that are similar to the size of the droplets to be delivered therethrough. Accordingly, in some embodiments, a delivery orifice as described herein has a diameter of from about 1 µm to about 1000 µm, inclusive, e.g., from about 10 µm to about 300 µm, inclusive. In some embodiments, a delivery orifice as described herein has a diameter of from about 1 µm to about 10 µm, from about 10

µm to about 100 µm, from about 100 µm to about 500 µm, or from about 500 µm to about 1000 µm, inclusive.

The nozzle can be molded as part of a microfluidic sorter as described herein, or can be a separate part that is mated with a microfluidic sorter as described herein. Suitable materials for the nozzle may include, e.g., polymeric tubing, small bore hypodermic tubing, and modified glass capillaries.

Embodiments of the subjects disclosure also include devices including one or more automated system integrated with the delivery orifice, wherein the automated system (a) selectively positions, e.g., positions by moving one or more distance on the order of magnitude of a discrete entity, the delivery orifice in proximity to a substrate or a portion thereof during operation and/or (b) selectively positions, e.g., positions by moving one or more distance on the order of magnitude of a discrete entity, the substrate or portion thereof in proximity to the delivery orifice during operation, such that a discrete entity, e.g., a droplet, can be ejected from the delivery orifice and/or deposited on the substrate. In some embodiments, automated systems are electronic and/or include one or more control unit for controlling automation, such as a control unit including a central processing unit.

As noted above, droplet printers may include one or more flow channels, e.g., flow channels which discrete entities may pass into, out of, and/or through. In certain embodiments, flow channels are one or more "micro" channel. Such channels may have at least one cross-sectional dimension on the order of a millimeter or smaller (e.g., less than or equal to about 1 millimeter). For certain applications, this dimension may be adjusted; in some embodiments the at least one cross-sectional dimension is about 500 micrometers or less. In some embodiments, the cross-sectional dimension is about 100 micrometers or less, or about 10 micrometers or less, and sometimes about 1 micrometer or less. A cross-sectional dimension is one that is generally perpendicular to the direction of centerline flow, although it should be understood that when encountering flow through elbows or other features that tend to change flow direction, the cross-sectional dimension in play need not be strictly perpendicular to flow. It should also be understood that in some embodiments, a micro-channel may have two or more cross-sectional dimensions such as the height and width of a rectangular cross-section or the major and minor axes of an elliptical cross-section. Either of these dimensions may be compared against sizes presented here. Note that microchannels employed in this disclosure may have two dimensions that are grossly disproportionate—e.g., a rectangular cross-section having a height of about 100-200 micrometers and a width on the order or a centimeter or more. Of course, certain devices may employ channels in which the two or more axes are very similar or even identical in size (e.g., channels having a square or circular cross-section).

Microfluidic devices, in some embodiments of this disclosure, are fabricated using microfabrication technology. Such technology may be employed to fabricate integrated circuits (ICs), microelectromechanical devices (MEMS), display devices, and the like. Among the types of microfabrication processes that can be employed to produce small dimension patterns in microfluidic device fabrication are photolithography (including X-ray lithography, e-beam lithography, etc.), self-aligned deposition and etching technologies, anisotropic deposition and etching processes, self-assembling mask formation (e.g., forming layers of hydrophobic-hydrophilic copolymers), etc.

In view of the above, it should be understood that some of the principles and design features described herein can be scaled to larger devices and systems including devices and systems employing channels reaching the millimeter or even centimeter scale channel cross-sections. Thus, when describing some devices and systems as "microfluidic," it is intended that the description apply equally, in certain embodiments, to some larger scale devices.

When referring to a microfluidic "device" it is generally intended to represent a single entity in which one or more channels, reservoirs, stations, etc. share a continuous substrate, which may or may not be monolithic. Aspects of microfluidic devices include the presence of one or more fluid flow paths, e.g., channels, having dimensions as discussed herein. A microfluidics "system" may include one or more microfluidic devices and associated fluidic connections, electrical connections, control/logic features, etc.

For example, systems of the subject disclosure may include one or more discrete entity printer, e.g., one or more droplet printer, and/or a substrate or portion thereof, e.g., a substrate surface, for receiving one or more discrete entities, e.g., droplets deposited thereon by, for example, a delivery orifice of a discrete entity printer, e.g., a droplet printer. Systems may also include one or more of: (a) a temperature control module for controlling the temperature of one or more portions of the subject devices and/or discrete entities therein and which is operably connected to the discrete entity printer, e.g., a droplet printer, (b) a detection means, i.e., a detector, e.g., an optical imager, operably connected to the discrete entity printer, e.g., a droplet printer, (c) an incubator, e.g., a cell incubator, operably connected to the discrete entity printer, e.g., a droplet printer, and (d) a sequencer operably connected to the discrete entity printer, e.g., a droplet printer. The subject systems may also include one or more conveyor configured to move, e.g., convey, a substrate from a first discrete entity, e.g., droplet, receiving position to one or more of (a)-(d).

The subject devices and systems, include one or more sorter for sorting discrete entities, e.g., droplets, into one or more flow channels. Such a sorter may sort and distribute discrete entities, e.g., droplets, based on one or more characteristics of the discrete entities including composition, size, shape, buoyancy, or other characteristics.

Aspects of the devices also include one or more detection means i.e., a detector, e.g., an optical imager, configured for detecting the presence of one or more discrete entities, e.g., droplets, or one or more characteristics thereof, including their composition. In some embodiments, detection means are configured to recognize one or more components of one or more discrete entities, e.g., discrete entities, in one or more flow channel.

In various embodiments, microfluidic devices of this disclosure provide a continuous flow of a fluid medium. Fluid flowing through a channel in a microfluidic device exhibits many unique properties. Typically, the dimensionless Reynolds number is extremely low, resulting in flow that always remains laminar. Further, in this regime, two fluids joining will not easily mix, and diffusion alone may drive the mixing of two compounds.

In addition, the subject devices, in some embodiments, include one or more temperature and/or pressure control module. Such a module may be capable of modulating temperature and/or pressure of a carrier fluid in one or more flow channels of a device. More specifically, a temperature control module may be one or more thermal cycler.

Various features and examples of microfluidic device components suitable for use with this disclosure will now be described.

Substrate

According to the subject disclosure, substrates used in microfluidic devices and/or systems are the supports in which the necessary elements for fluid transport are provided. The basic structure of a substrate may be monolithic, laminated, or otherwise sectioned. Substrates may include one or more flow channels, such as microchannels serving as conduits for molecular libraries and/or reagents. They may also include input ports, output ports, and/or features to assist in flow control.

In certain embodiments, the substrate choice may be dependent on the application and design of the device. Substrate materials may be chosen for their compatibility with a variety of operating conditions. Limitations in microfabrication processes for a given material are also relevant considerations in choosing a suitable substrate. Useful substrate materials which may be employed with the subject disclosure include, e.g., glass, polymers, silicon, metal, ceramics, and/or combinations thereof.

The subject devices, in some embodiments, include one or more polymers. Polymers are useful materials for microfluidic devices because they are amenable to both cost effective and high volume production. Polymers, including polymers for use in accordance with the subject disclosure, can be classified into three categories according to their molding behavior: thermoplastic polymers, elastomeric polymers and duroplastic polymers. Thermoplastic polymers can be molded into shapes above the glass transition temperature, and will retain these shapes after cooling below the glass transition temperature. Elastomeric polymers can be stretched upon application of an external force, but will go back to original state once the external force is removed. Elastomers do not melt before reaching their decomposition temperatures. Duroplastic polymers have to be cast into their final shape because they soften a little before the temperature reaches their decomposition temperature.

Among the polymers that may be used in microfabricated device of this disclosure are polyamide (PA), polybutylenterephthalate (PBT), polycarbonate (PC), polyethylene (PE), polymethylmethacrylate (PMMA), polyoxymethylene (POM), polypropylene (PP), polyphenylenether (PPE), polystyrene (PS) and polysulphone (PSU). The chemical and physical properties of polymers can limit their uses in microfluidic devices. Specifically in comparison to glass, the lower resistance against chemicals, the aging, the mechanical stability, and the UV stability can limit the use of polymers for certain applications.

Glass, which may also be used as the substrate material, has specific advantages under certain operating conditions. Since glass is chemically inert to most liquids and gases, it is particularly appropriate for applications employing certain solvents that have a tendency to dissolve plastics. Additionally, its transparent properties make glass particularly useful for optical or UV detection.

Surface Treatments and Coatings

Surface modification may be useful for controlling the functional mechanics (e.g., flow control) of a microfluidic device and may be applied according to the subject disclosure. For example, it may be useful to keep fluidic species from adsorbing to channel walls or for attaching antibodies to the surface for detection of biological components.

Polymer devices in particular tend to be hydrophobic, and thus loading of the channels may be difficult. The hydrophobic nature of polymer surfaces may also make it difficult to control electroosmotic flow (EOF). One technique for coating polymer surface according to the subject disclosure is the application of polyelectrolyte multilayers (PEM) to channel surfaces. PEM involves filling the channel successively with alternating solutions of positive and negative polyelectrolytes allowing for multilayers to form electrostatic bonds. Although the layers typically do not bond to the channel surfaces, they may completely cover the channels even after long-term storage. Another technique for applying a hydrophilic layer on polymer surfaces according to the subject disclosure involves the UV grafting of polymers to the surface of the channels. First grafting sites, radicals, are created at the surface by exposing the surface to UV irradiation while simultaneously exposing the device to a monomer solution. The monomers react to form a polymer covalently bonded at the reaction site.

In some embodiments, glass channels according to the subject disclosure, generally have high levels of surface charge, thereby causing proteins to adsorb and possibly hindering separation processes. In some situations, the disclosure includes applying a polydimethylsiloxane (PDMS) and/or surfactant coating to the glass channels. Other polymers that may be employed to retard surface adsorption include polyacrylamide, glycol groups, polysiloxanes, glyceroglycidoxypropyl, poly(ethyleneglycol) and hydroxyethylated poly(ethyleneimine). Furthermore, subject electroosmotic devices may include a coating bearing a charge that is adjustable in magnitude by manipulating conditions inside of the device (e.g. pH). The direction of the flow can also be selected based on the coating since the coating can either be positively or negatively charged.

Specialized coatings can also be applied according to this disclosure to immobilize certain species on the channel surface—this process is called "functionalizing the surface." For example, a polymethylmethacrylate (PMMA) surface may be coated with amines to facilitate attachment of a variety of functional groups or targets. Alternatively, PMMA surfaces can be rendered hydrophilic through an oxygen plasma treatment process.

Microfluidic Elements

Microfluidic systems and devices according to the subject disclosure can contain one or more flow channels, such as microchannels, valves, pumps, reactors, mixers and other/or components. Some of these components and their general structures and dimensions are discussed below.

Various types of valves can be applied for flow control in microfluidic devices of this disclosure. These include, but are not limited to passive valves and check valves (membrane, flap, bivalvular, leakage, etc.). Flow rate through these valves are dependent on various physical features of the valve such as surface area, size of flow channel, valve material, etc. Valves also have associated operational and manufacturing advantages/disadvantages that may be taken into consideration during design of a microfluidic device.

Embodiments of the subject devices include one or more micropumps. Micropumps, as with other microfluidic components, are subjected to manufacturing constraints. Typical considerations in pump design include treatment of bubbles, clogs, and durability. Micropumps which may be included in the subject devices include, but are not limited to electric equivalent pumps, fixed-stroke microdisplacement, peristaltic micromembrane and/or pumps with integrated check valves.

Macrodevices rely on turbulent forces such as shaking and stirring to mix reagents. In comparison, such turbulent forces are not practically attainable in microdevices, such as those of the present disclosure, and instead mixing in microfluidic devices is generally accomplished through diffusion. Since mixing through diffusion can be slow and inefficient, microstructures, such as those employed with the disclosed subject matter, are often designed to enhance the mixing process. These structures manipulate fluids in a way that increases interfacial surface area between the fluid regions, thereby speeding up diffusion. In certain embodiments, microfluidic mixers are employed. Such mixers may be provided upstream from, and in some cases integrated with, a microfluidic separation device and/or a sorter, of this disclosure.

In some embodiments, the devices and systems of the present disclosure include micromixers. Micromixers may be classified into two general categories: active mixers and passive mixers. Active mixers work by exerting active control over flow regions (e.g. varying pressure gradients, electric charges, etc.). Passive mixers do not require inputted energy and use only "fluid dynamics" (e.g. pressure) to drive fluid flow at a constant rate. One example of a passive mixer involves stacking two flow streams on top of one another separated by a plate. The flow streams are contacted with each other once the separation plate is removed. The stacking of the two liquids increases contact area and decreases diffusion length, thereby enhancing the diffusion process. Mixing and reaction devices can be connected to heat transfer systems if heat management is needed. As with macro-heat exchangers, micro-heat exchanges can either have co-current, counter-current, or cross-flow flow schemes. Microfluidic devices may have channel widths and depths between about 10 µm and about 10 cm. One channel structure includes a long main separation channel, and three shorter "offshoot" side channels terminating in either a buffer, sample, or waste reservoir. The separation channel can be several centimeters long, and the three side channels usually are only a few millimeters in length. Of course, the actual length, cross-sectional area, shape, and branch design of a microfluidic device depends on the application as well other design considerations such as throughput (which depends on flow resistance), velocity profile, residence time, etc.

Microfluidic devices described herein may include one or more electric field generators to perform certain steps of the methods described herein, including, but not limited to, picoinjection, droplet coalescence, selective droplet fusion, and droplet sorting. In certain embodiments, the electric fields are generated using metal electrodes. In particular embodiments, electric fields are generated using liquid electrodes. In certain embodiments, liquid electrodes include liquid electrode channels filled with a conducting liquid (e.g. salt water or buffer) and situated at positions in the microfluidic device where an electric field is desired. In particular embodiments, the liquid electrodes are energized using a power supply or high voltage amplifier. In some embodiments, the liquid electrode channel includes an inlet port so that a conducting liquid can be added to the liquid electrode channel. Such conducting liquid may be added to the liquid electrode channel, for example, by connecting a tube filled with the liquid to the inlet port and applying pressure. In particular embodiments, the liquid electrode channel also includes an outlet port for releasing conducting liquid from the channel. In particular embodiments, the liquid electrodes are used in picoinjection, droplet coalescence, selective droplet fusion, and/or droplet sorting aspects of a microfluidic device described herein. Liquid electrodes may find use, for example, where a material to be injected via application of an electric field is not charged.

In certain embodiments, the width of one or more of the microchannels of the microfluidic device (e.g., input microchannel, pairing microchannel, pioinjection microchannel, and/or a flow channel upstream or downstream of one or more of these channels) is 100 microns or less, e.g, 90 microns or less, 80 microns or less, 70 microns or less, 60 microns or less, 50 microns or less, e.g., 45 microns or less, 40 microns or less, 39 microns or less. 38 microns or less, 37 microns or less, 36 microns or less, 35 microns or less, 34 microns or less, 33 microns or less, 32 microns or less, 31 microns or less. 30 microns or less, 29 microns or less, 28 microns or less, 27 microns or less, 26 microns or less, 25 microns or less, 20 microns or less, 15 microns or less, or 10 microns or less. In some embodiments, the width of one or more of the above microchannels is from about 10 microns to about 15 microns, from about 15 microns to about 20 microns, from about 20 microns to about 25 microns, from about 25 microns to about 30 microns, from about 30 microns to about 35 microns, from about 35 microns to about 40 microns, from about 40 microns to about 45 microns, or from about 45 microns to about 50 microns, from about 50 microns to about 60 microns, from about 60 microns to about 70 microns, from about 70 microns to about 80 microns, from about 80 microns to about 90 microns, or from about 90 microns to about 100 microns.

Additional descriptions of various microchannel structures and features which may be utilized in connection with the disclosed methods and devices are provided in PCT Publication No. WO 2014/028378, the disclosure of which is incorporated by reference herein in its entirety and for all purposes.

Methods of Fabrication

According to the disclosed embodiments, microfabrication processes differ depending on the type of materials used in the substrate and/or the desired production volume. For small volume production or prototypes, fabrication techniques include LIGA, powder blasting, laser ablation, mechanical machining, electrical discharge machining, photoforming, etc. Technologies for mass production of microfluidic devices may use either lithographic or master-based replication processes. Lithographic processes for fabricating substrates from silicon/glass include both wet and dry etching techniques commonly used in fabrication of semiconductor devices. Injection molding and hot embossing typically are used for mass production of plastic substrates.

Glass, Silicon and Other "Hard" Materials (Lithography, Etching, Deposition)

According to embodiments of the disclosed subject matter, a combination of lithography, etching and/or deposition techniques may be used to make microcanals and microcavities out of glass, silicon and other "hard" materials. Technologies based on the above techniques may be applied in fabrication of devices in the scale of 0.1-500 micrometers.

Microfabrication techniques based on semiconductor fabrication processes are generally carried out in a clean room. The quality of the clean room is classified by the number of particles <4 µm in size in a cubic inch. Typical clean room classes for MEMS microfabrication may be 1000 to 10000.

In certain embodiments, photolithography may be used in microfabrication. In photolithography, a photoresist that has been deposited on a substrate is exposed to a light source through an optical mask. Conventional photoresist methods allow structural heights of up to 10-40 µm. If higher structures are needed, thicker photoresists such as SU-8, or polyimide, which results in heights of up to 1 mm, can be used.

After transferring the pattern on the mask to the photoresist-covered substrate, the substrate is then etched using either a wet or dry process. In wet etching, the substrate— area not protected by the mask—is subjected to chemical attack in the liquid phase. The liquid reagent used in the etching process depends on whether the etching is isotropic or anisotropic. Isotropic etching generally uses an acid to form three-dimensional structures such as spherical cavities in glass or silicon. Anisotropic etching forms flat surfaces such as wells and canals using a highly basic solvent. Wet anisotropic etching on silicon creates an oblique channel profile.

Dry etching involves attacking the substrate by ions in either a gaseous or plasma phase. Dry etching techniques can be used to create rectangular channel cross-sections and arbitrary channel pathways. Various types of dry etching that may be employed including physical, chemical, physico-chemical (e.g., RIE), and physico-chemical with inhibitor. Physical etching uses ions accelerated through an electric field to bombard the substrate's surface to "etch" the structures. Chemical etching may employ an electric field to migrate chemical species to the substrate's surface. The chemical species then reacts with the substrate's surface to produce voids and a volatile species.

In certain embodiments, deposition is used in microfabrication. Deposition techniques can be used to create layers of metals, insulators, semiconductors, polymers, proteins and other organic substances. Most deposition techniques fall into one of two main categories: physical vapor deposition (PVD) and chemical vapor deposition (CVD). In one approach to PVD, a substrate target is contacted with a holding gas (which may be produced by evaporation for example). Certain species in the gas adsorb to the target's surface, forming a layer constituting the deposit. In another approach commonly used in the microelectronics fabrication industry, a target containing the material to be deposited is sputtered with using an argon ion beam or other appropriately energetic source. The sputtered material then deposits on the surface of the microfluidic device. In CVD, species in contact with the target react with the surface, forming components that are chemically bonded to the object. Other deposition techniques include: spin coating, plasma spraying, plasma polymerization, dip coating, casting and Langmuir-Blodgett film deposition. In plasma spraying, a fine powder containing particles of up to 100 μm in diameter is suspended in a carrier gas. The mixture containing the particles is accelerated through a plasma jet and heated. Molten particles splatter onto a substrate and freeze to form a dense coating. Plasma polymerization produces polymer films (e.g. PMMA) from plasma containing organic vapors.

Once the microchannels, microcavities and other features have been etched into the glass or silicon substrate, the etched features are usually sealed to ensure that the microfluidic device is "watertight." When sealing, adhesion can be applied on all surfaces brought into contact with one another. The sealing process may involve fusion techniques such as those developed for bonding between glass-silicon, glass-glass, or silicon-silicon.

Anodic bonding can be used for bonding glass to silicon. A voltage is applied between the glass and silicon and the temperature of the system is elevated to induce the sealing of the surfaces. The electric field and elevated temperature induces the migration of sodium ions in the glass to the glass-silicon interface. The sodium ions in the glass-silicon interface are highly reactive with the silicon surface forming a solid chemical bond between the surfaces. The type of glass used may have a thermal expansion coefficient near that of silicon (e.g. Pyrex Corning 7740).

Fusion bonding can be used for glass-glass or silicon-silicon sealing. The substrates are first forced and aligned together by applying a high contact force. Once in contact, atomic attraction forces (primarily van der Waals forces) hold the substrates together so they can be placed into a furnace and annealed at high temperatures. Depending on the material, temperatures used ranges between about 600 and 1100° C.

Polymers/Plastics

A variety of techniques may be employed for micromachining plastic substrates in accordance with the subject embodiments. Among these are laser ablation, stereolithography, oxygen plasma etching, particle jet ablation, and microelectro-erosion. Some of these techniques can be used to shape other materials (glass, silicon, ceramics, etc.) as well.

To produce multiple copies of a microfluidic device, replication techniques are employed. Such techniques involve first fabricating a master or mold insert containing the pattern to be replicated. The master is then used to mass-produce polymer substrates through polymer replication processes.

In the replication process, the master pattern contained in a mold is replicated onto the polymer structure. In certain embodiments, a polymer and curing agent mix is poured onto a mold under high temperatures. After cooling the mix, the polymer contains the pattern of the mold, and is then removed from the mold. Alternatively, the plastic can be injected into a structure containing a mold insert. In micro-injection, plastic heated to a liquid state is injected into a mold. After separation and cooling, the plastic retains the mold's shape.

PDMS (polydimethylsiloxane), a silicon-based organic polymer, may be employed in the molding process to form microfluidic structures. Because of its elastic character, PDMS is suited for microchannels between about 5 μm and 500 μm. Specific properties of PDMS make it suitable for microfluidic purposes. Such properties include:

1) It is optically clear which allows for visualization of the flows.
2) PDMS, when mixed with a proper amount of reticulating agent, has elastomeric qualities that facilitates keeping microfluidic connections "watertight."
3) Valves and pumps using membranes can be made with PDMS because of its elasticity.
4) Untreated PDMS is hydrophobic, and becomes temporarily hydrophilic after oxidation of surface by oxygen plasma or after immersion in strong base; oxidized PDMS adheres by itself to glass, silicon, or polyethylene, as long as those surfaces were themselves exposed to an oxygen plasma.
5) PDMS is permeable to gas. Filling of the channel with liquids is facilitated even when there are air bubbles in the canal because the air bubbles are forced out of the material. Additionally, PDMS is also permeable to non polar-organic solvents.

Microinjection can be used to form plastic substrates employed in a wide range of microfluidic designs. In this process, a liquid plastic material is first injected into a mold under vacuum and pressure, at a temperature greater than the glass transition temperature of the plastic. The plastic is then cooled below the glass transition temperature. After removing the mold, the resulting plastic structure is the negative of the mold's pattern.

Yet another replicating technique is hot embossing, in which a polymer substrate and a master are heated above the polymer's glass transition temperature, Tg (which for PMMA or PC is around 100-180° C.). The embossing master is then pressed against the substrate with a preset compression force. The system is then cooled below Tg and the mold and substrate are then separated.

Typically, the polymer is subjected to the highest physical forces upon separation from the mold tool, particularly when the microstructure contains high aspect ratios and vertical walls. To avoid damage to the polymer microstructure, material properties of the substrate and the mold tool may be taken into consideration. These properties include: sidewall roughness, sidewall angles, chemical interface between embossing master and substrate and temperature coefficients. High sidewall roughness of the embossing tool can damage the polymer microstructure since roughness contributes to frictional forces between the tool and the structure during the separation process. The microstructure may be destroyed if frictional forces are larger than the local tensile strength of the polymer. Friction between the tool and the substrate may be important in microstructures with vertical walls. The chemical interface between the master and substrate could also be of concern. Because the embossing process subjects the system to elevated temperatures, chemical bonds could form in the master-substrate interface. These interfacial bonds could interfere with the separation process. Differences in the thermal expansion coefficients of the tool and the substrate could create addition frictional forces.

Various techniques can be employed to form molds, embossing masters, and other masters containing patterns used to replicate plastic structures through the replication processes mentioned above. Examples of such techniques include LIGA (described below), ablation techniques, and various other mechanical machining techniques. Similar techniques can also be used for creating masks, prototypes and microfluidic structures in small volumes. Materials used for the mold tool include metals, metal alloys, silicon and other hard materials.

Laser ablation may be employed to form microstructures either directly on the substrate or through the use of a mask. This technique uses a precision-guided laser, typically with wavelength between infrared and ultraviolet. Laser ablation may be performed on glass and metal substrates, as well as on polymer substrates. Laser ablation can be performed either through moving the substrate surface relative to a fixed laser beam, or moving the beam relative to a fixed substrate. Various micro-wells, canals, and high aspect structures can be made with laser ablation.

Certain materials, such as stainless steel, make durable mold inserts and can be micromachined to form structures down to the 10-µm range. Various other micromachining techniques for microfabrication exist including µ-Electro Discharge Machining (µ-EDM), µ-milling, focused ion beam milling. µ-EDM allows the fabrication of 3-dimensional structures in conducting materials. In µ-EDM, material is removed by high-frequency electric discharge generated between an electrode (cathode tool) and a workpiece (anode). Both the workpiece and the tool are submerged in a dielectric fluid. This technique produces a comparatively rougher surface but offers flexibility in terms of materials and geometries.

Electroplating may be employed for making a replication mold tool/master out of, e.g., a nickel alloy. The process starts with a photolithography step where a photoresist is used to defined structures for electroplating. Areas to be electroplated are free of resist. For structures with high aspect ratios and low roughness requirements, LIGA can be used to produce electroplating forms. LIGA is a German acronym for Lithographic (Lithography), Galvanoformung (electroplating), Abformung (molding). In one approach to LIGA, thick PMMA layers are exposed to x-rays from a synchrotron source. Surfaces created by LIGA have low roughness (around 10 nm RMS) and the resulting nickel tool has good surface chemistry for most polymers.

As with glass and silicon devices, polymeric microfluidic devices must be closed up before they can become functional. Common problems in the bonding process for microfluidic devices include the blocking of channels and changes in the physical parameters of the channels. Lamination is one method used to seal plastic microfluidic devices. In one lamination process, a PET foil (about 30 µm) coated with a melting adhesive layer (typically 5 µm-10 µm) is rolled with a heated roller, onto the microstructure. Through this process, the lid foil is sealed onto the channel plate. Several research groups have reported a bonding by polymerization at interfaces, whereby the structures are heated and force is applied on opposite sides to close the channel. But excessive force applied may damage the microstructures. Both reversible and irreversible bonding techniques exist for plastic-plastic and plastic-glass interfaces. One method of reversible sealing involves first thoroughly rinsing a PDMS substrate and a glass plate (or a second piece of PDMS) with methanol and bringing the surfaces into contact with one another prior to drying. The microstructure is then dried in an oven at 65° C. for 10 min. No clean room is required for this process. Irreversible sealing is accomplished by first thoroughly rinsing the pieces with methanol and then drying them separately with a nitrogen stream. The two pieces are then placed in an air plasma cleaner and oxidized at high power for about 45 seconds. The substrates are then brought into contact with each other and an irreversible seal forms spontaneously.

Other available techniques include laser and ultrasonic welding. In laser welding, polymers are joined together through laser-generated heat. This method has been used in the fabrication of micropumps. Ultrasonic welding is another bonding technique that may be employed in some applications.

One nucleic acid amplification technique described herein is a polymerase chain reaction (PCR). However, in certain embodiments, non-PCR amplification techniques may be employed such as various isothermal nucleic acid amplification techniques; e.g., real-time strand displacement amplification (SDA), rolling-circle amplification (RCA) and multiple-displacement amplification (MDA).

Regarding PCR amplification modules, it will be necessary to provide to such modules at least the building blocks for amplifying nucleic acids (e.g., ample concentrations of four nucleotides), primers, polymerase (e.g., Taq), and appropriate temperature control programs). The polymerase and nucleotide building blocks may be provided in a buffer solution provided via an external port to the amplification module or from an upstream source. In certain embodiments, the buffer stream provided to the sorting module contains some of all the raw materials for nucleic acid amplification. For PCR in particular, precise temperature control of the reacting mixture is extremely important in order to achieve high reaction efficiency. One method of on-chip thermal control is Joule heating in which electrodes are used to heat the fluid inside the module at defined locations. The fluid conductivity may be used as a temperature feedback for power control.

In certain aspects, the discrete entities, e.g., microdroplets, containing the PCR mix may be flowed through a channel that incubates the discrete entities under conditions effective for PCR. Flowing the discrete entities through a channel may involve a channel that snakes over various temperature zones maintained at temperatures effective for PCR. Such channels may, for example, cycle over two or more temperature zones, wherein at least one zone is maintained at about 65° C. and at least one zone is maintained at about 95° C. As the discrete entities move through such zones, their temperature cycles, as needed for PCR. The precise number of zones, and the respective temperature of each zone, may be readily determined by those of skill in the art to achieve the desired PCR amplification.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-252 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A method of delivering discrete entities to a substrate, the method including:
   flowing a plurality of discrete entities through a microfluidic device in a carrier fluid, wherein the discrete entities are insoluble and/or immiscible in the carrier fluid;
   directing the carrier fluid and one or more of the plurality of discrete entities through a delivery orifice to the substrate; and
   affixing the one or more of the plurality of discrete entities to the substrate.
2. The method of 1, wherein the one or more of the plurality of discrete entities are affixed to the substrate via a force, wherein the force is selected from a gravitational force, an electrical force, a magnetic force, and combinations thereof.
3. The method of 2, including storing the affixed entity under controlled environmental conditions for a storage period, wherein the force is maintained during the storage period.
4. The method of 3, wherein the controlled environmental conditions include a constant temperature and/or pressure.
5. The method of any one of 2-4, wherein the force is an electrical force.
6. The method of 5, wherein the electrical force is a dielectrophoretic force.
7. The method of any one of 1-6, wherein the discrete entities are droplets.
8. The method of 7, wherein the droplets are affixed to the substrate via wetting.
9. The method of 7, wherein the droplets include an aqueous fluid, which is immiscible with the carrier fluid.
10. The method of 9, wherein the substrate includes on a first surface a layer of fluid which is miscible with the carrier fluid and immiscible with the aqueous fluid, and wherein the droplets are affixed to the first surface of the substrate following introduction into the layer of fluid on the first surface of the substrate.
11. The method of 7, wherein the carrier fluid is an aqueous fluid and the droplets include a fluid which is immiscible with the carrier fluid.
12. The method of 11, wherein the substrate includes on a first surface a layer of aqueous fluid which is miscible with the carrier fluid and immiscible with the fluid included by the droplets, and wherein the droplets are affixed to the first surface of the substrate following introduction into the layer of aqueous fluid on the first surface of the substrate.
13. The method of 1, wherein the discrete entities are affixed to the substrate via interfacial tension.
14. The method of any one of 1-13, wherein the discrete entities have a dimension of from about 1 to 1000 μm.
15. The method of 14, wherein the discrete entities have a diameter of from about 1 to 1000 μm.
16. The method of any one of 1-13, wherein the discrete entities have a volume of from about 1 femtoliter to about 1000 nanoliters.
17. The method of any one of 1-16, wherein the microfluidic device includes a sorter, and wherein the method includes sorting, via the sorter, the one or more of the plurality of discrete entities to be delivered through the delivery orifice to the substrate from the plurality of discrete entities.
18. The method of 17, wherein the sorter includes a flow channel including a gapped divider including a separating wall which extends less than the complete height of the flow channel.
19. The method of 17, wherein the plurality of discrete entities is optically scanned prior to the sorting.
20. The method of 19, wherein the sorter includes an optical fiber configured to apply excitation energy to one or more of the plurality of discrete entities.
21. The method of 20, wherein the sorter includes a second optical fiber configured to collect a signal produced by the application of excitation energy to one or more of the plurality of discrete entities.
22. The method of 20, wherein the optical fiber is configured to apply excitation energy to one or more of the plurality of discrete entities and collect a signal produced by the application of the excitation energy to one or more of the plurality of discrete entities.
23. The method of 19, wherein the sorting is based on results obtained from the optical scan.
24. The method of 17, wherein the sorter is an active sorter.
25. The method of 17, wherein the sorter is a passive sorter.
26. The method of 24, wherein the sorting includes sorting via dielectrophoresis.
27. The method of 24, wherein the sorter includes one or more microfluidic valves, and wherein the sorting includes sorting via activation of the one or more microfluidic valves.
28. The method of any one of 1-27, wherein the discrete entities are droplets, the microfluidic device includes a selectively activatable droplet maker which forms droplets from a fluid stream, and wherein the method includes forming one or more of the plurality of discrete entities via selective activation of the droplet maker.
29. The method of any one of 1-28, wherein the plurality of discrete entities includes discrete entities which differ in composition.
30. The method of any one of 1-29, wherein the microfluidic device is integrated with an automated system which selectively positions the delivery orifice relative to the substrate, and wherein the method includes selectively positioning via the automated system the delivery orifice relative to the substrate to selectively deliver the one or more of the plurality of discrete entities to one or more locations on or in proximity to the substrate.

31. The method of any one of 1-29, wherein the microfluidic device is integrated with an automated system which selectively positions the substrate relative to the delivery orifice, and wherein the method includes selectively positioning via the automated system the substrate relative to the delivery orifice to selectively deliver the one or more of the plurality of discrete entities to one or more locations on or in proximity to the substrate.

32. The method of 30 or 31, wherein the method includes delivering a first member of the plurality of discrete entities to a first location on or in proximity to the substrate and a second member of the plurality of discrete entities to a second location on or in proximity to the substrate.

33. The method of 32, wherein the first and second locations are the same.

34. The method of any one of 1-33, wherein one or more biological assays are performed in one or more of the discrete entities before and/or after delivery to the substrate.

35. The method of any one of 1-34, wherein the temperature of one or more of the discrete entities is controlled before and/or after delivery to the substrate.

36. The method of 35, wherein one or more of the discrete entities are thermalcycled before and/or after delivery to the substrate.

37. The method of any one of 17-36, wherein the members of the plurality of discrete entities which are not sorted for delivery through the delivery orifice to the substrate are recovered.

38. The method of 37, wherein the recovered members of the plurality of discrete entities are recycled such that the method of 1 is repeated with the recovered members of the plurality of discreet entities.

39. The method of 38, wherein recovered members of the plurality of discrete entities are continuously recycled during performance of the method.

40. The method of any one of 1-39, wherein one or more of the plurality of discrete entities includes a cell.

41. The method 40, wherein each member of the plurality of discrete entities includes not more than one cell.

42. The method of any one of 1-39, wherein one or more of the plurality of discrete entities includes a nucleic acid.

43. The method of any one of 1-42, wherein the method includes encapsulating or incorporating one or more reagents into the plurality of discrete entities.

44. The method of 43, wherein the one or more reagents include amplification reagents.

45. The method of 44, wherein the amplification reagents include Polymerase Chain Reaction (PCR) reagents.

46. A method of printing one or more cell layers, the method including:
    encapsulating cells in droplets including an aqueous fluid to provide cell-including droplets;
    flowing a plurality of droplets including the cell-including droplets through a microfluidic device in a carrier fluid, wherein the carrier fluid is immiscible with the aqueous fluid;
    directing the carrier fluid and a plurality of the cell-including droplets through a delivery orifice to a substrate; and
    affixing the plurality of the cell-including droplets to the substrate to provide a first layer of cell-including droplets, wherein the substrate includes on a first surface a layer of fluid which is miscible with the carrier fluid and immiscible with the aqueous fluid, and wherein the plurality of the cell-including droplets are affixed to the first surface of the substrate following introduction into the layer of fluid on the first surface of the substrate.

47. The method of 46, wherein the microfluidic device includes a sorter, and wherein the method includes sorting, via the sorter, the plurality of cell-including droplets to be delivered through the delivery orifice to the substrate from the cell-including droplets.

48. The method of 47, wherein the sorter includes a flow channel including a gapped divider including a separating wall which extends less than the complete height of the flow channel.

49. The method of any one of 46-48, wherein the method includes
    encapsulating or incorporating one or more reagents into droplets to provide reagent-including droplets;
    flowing a plurality of droplets including the reagent-including droplets through the microfluidic device in the carrier fluid;
    and directing the carrier fluid and a plurality of the reagent-including droplets through the delivery orifice to the substrate.

50. The method of 49, wherein the reagent-including droplets and the cell-including droplets are the same.

51. The method of 49, wherein cell-including droplets and reagent-including droplets are deposited in the same layer on the substrate.

52. The method of any one of 49-51, wherein the one or more reagents include a material which facilitates cell growth.

53. The method of 52, wherein the material which facilitates cell growth includes a cell culture media component.

54. The method of 52, wherein the material which facilitates cell growth includes a cell culture substrate.

55. The method of any one of 46-54, wherein the method includes
    directing the carrier fluid and a second plurality of the cell-including droplets through the delivery orifice to the substrate; and
    depositing a second layer of cell-including droplets on the first layer of cell-including droplets thereby providing a layered structure.

56. The method of any one of 46-54, wherein the method includes
    depositing a layer of reagent-including droplets on the first layer of cell-including droplets thereby providing a layered structure.

57. A method of printing and detecting one or more cells, the method including:
    encapsulating cells in droplets including an aqueous fluid to provide cell-including droplets;
    flowing a plurality of droplets including the cell-including droplets through a microfluidic device in a carrier fluid, wherein the carrier fluid is immiscible with the aqueous fluid;
    directing the carrier fluid and a plurality of the cell-including droplets through a delivery orifice to a substrate;
    affixing the plurality of the cell-including droplets to the substrate, wherein the substrate includes on a first surface a layer of fluid which is miscible with the carrier fluid and immiscible with the aqueous fluid, and wherein the plurality of the cell-including droplets are affixed to the first surface of the substrate following introduction into the layer of fluid on the first surface of the substrate; and detecting one or more of the cells in the affixed cell-including droplets, a component of one or more of the cells in the affixed cell-including droplets, or a product of one or more of the cells in the affixed cell-including droplets.

58. The method of 57, wherein the detecting is performed at a plurality of time points.
59. The method of 57, wherein the method includes continuously detecting over a period of time one or more of the cells in the affixed cell-including droplets, a component of one or more of the cells in the affixed cell-including droplets, or a product of one or more of the cells in the affixed cell-including droplets.
60. The method of any one of 57-59, including recovering from the affixed cell-including droplets one or more of the cells in the affixed cell-including droplets, a component of one or more of the cells in the affixed cell-including droplets, or a product of one or more of the cells in the affixed cell-including droplets.
61. The method of 60, including recovering DNA from one or more of the cells in the affixed cell-including droplets.
62. The method of 61, including sequencing the DNA.
63. A method of printing a three-dimensional structure, the method including:
    flowing discrete entities through a microfluidic device in a carrier fluid, wherein the discrete entities are insoluble and/or immiscible in the carrier fluid; and
    directing the carrier fluid and a first plurality of the discrete entities through a delivery orifice to a substrate to provide a first layer thereon;
    directing the carrier fluid and a second plurality of the discrete entities through the delivery orifice to the first layer to provide a second layer thereon; and
    one or more additional directing steps in which a plurality of the discrete entities are directed through the delivery orifice to an immediately preceding layer to provide a subsequent layer thereon, wherein a multilayer, three-dimensional structure is provided.
64. The method of 63, wherein the discrete entities are hydrophilic and the carrier fluid is hydrophobic.
65. The method of 64, wherein the discrete entities are droplets.
66. The method of 65, wherein the droplets include an aqueous fluid.
67. The method of 66, wherein the substrate includes on a first surface a layer of fluid which is miscible with the carrier fluid and immiscible with the aqueous fluid, and wherein the droplets are affixed to the first surface of the substrate following introduction into the layer of fluid on the first surface of the substrate.
68. The method of 63, wherein the discrete entities are hydrophobic and the carrier fluid is hydrophilic.
69. The method of 68, wherein the discrete entities are droplets.
70. The method of 69, wherein the carrier fluid is an aqueous fluid and the droplets include a fluid which is immiscible with the carrier fluid.
71. The method of 70, wherein the substrate includes on a first surface a layer of aqueous fluid which is miscible with the carrier fluid and immiscible with the fluid included by the droplets, and wherein the droplets are affixed to the first surface of the substrate following introduction into the layer of aqueous fluid on the first surface of the substrate.
72. The method of 64 or 68, wherein the discrete entities consist of a solid material.
73. The method of 64 or 68, wherein the discrete entities consist of a gel material.
74. The method of 64 or 68, including initiating a reaction which causes the discrete entities or the carrier fluid to solidify.
75. The method of 74, wherein the reaction is a photopolymerization reaction.
76. A method of delivering droplets from a delivery orifice, the method including:
    flowing a plurality of droplets through a microfluidic device in a carrier fluid, wherein the microfluidic device includes a sorter;
    detecting one or more of the plurality of droplets to provide one or more detected droplets;
    sorting via the sorter the one or more detected droplets from the plurality of droplets;
    directing the carrier fluid and the one or more detected droplets through the delivery orifice.
77. The method of 76, including depositing the one or more detected droplets on a substrate.
78. The method of 76 or 77, wherein the droplets include an aqueous fluid, which is immiscible with the carrier fluid.
79. The method of 78, wherein the substrate includes on a first surface a layer of fluid which is miscible with the carrier fluid and immiscible with the aqueous fluid, and wherein the one or more detected droplets are introduced into the layer of fluid on the first surface of the substrate.
80. The method of 76 or 77, wherein the carrier fluid is an aqueous fluid and the droplets include a fluid which is immiscible with the carrier fluid.
81. The method of 80, wherein the substrate includes on a first surface a layer of aqueous fluid which is miscible with the carrier fluid and immiscible with the fluid included by the droplets, and wherein the one or more detected droplets are introduced into the layer of aqueous fluid on the first surface of the substrate.
82. The method of any one of 76-81, wherein the sorter includes a flow channel including a gapped divider including a separating wall which extends less than the complete height of the flow channel.
83. A method of affixing a droplet to a substrate, the method including:
    delivering a droplet in a first carrier fluid from a microfluidic device, through an orifice, to a substrate surface;
    positioning the droplet in a second carrier fluid on the substrate surface; and
    affixing the droplet to the substrate surface via a force.
84. The method of 83, wherein the first and second carrier fluid are the same.
85. The method of 83, wherein the force is selected from a gravitational force, an electrical force, a magnetic force, and combinations thereof.
86. The method of 85, wherein the force is a magnetic force.
87. The method of 85, wherein the force is an electrical force.
88. The method of 87, wherein the electrical force is a dielectrophoretic force.
89. The method of 89, wherein the substrate includes a plurality of channels filled with a conductive liquid or solid material and an insulating sheet positioned between the plurality of channels and the carrier fluid, wherein the plurality of channels are patterned to generate an electric field gradient above the insulating sheet upon application of a voltage, and wherein the method includes applying a voltage to one or more of the plurality of channels sufficient to generate the electrical field gradient, wherein the electrical field gradient produces a dielectrophoretic force sufficient to affix the droplet to the substrate surface.

90. The method of 89, wherein the substrate includes a plurality of channels filled with a conductive liquid or solid material and an insulating sheet positioned between the plurality of channels and the carrier fluid, wherein the plurality of channels are patterned to generate a dielectrophoretic force sufficient to affix the droplet to the substrate surface.

91. The method of 89, wherein the substrate and the droplet have net charges which are opposite in polarity.

92. The method of 83, wherein the wettability of the substrate is sufficient to affix the droplet to the substrate via wetting forces.

93. The method of 83, including modifying the wettability of the substrate so as to be sufficient to affix the droplet to the substrate via wetting forces.

94. The method of 89, wherein the substrate includes a plurality of channels filled with a conductive liquid or solid material and an insulating sheet positioned between the plurality of channels and the carrier fluid, wherein the plurality of channels are patterned to provide a plurality of electrode features, and wherein the plurality of electrode features are positioned relative to each other so as to provide positions on the substrate surface capable of reducing droplet interfacial energy when a voltage is applied to one or more of the plurality of channels, and wherein the positions are sufficient to affix the droplet to the substrate surface.

95. The method of 94, wherein at least one electrode feature is positioned relative to at least one other electrode feature such that there is a gap between the features, wherein the distance of the gap is within an order of magnitude of the diameter of the droplet.

96. The method of 95, including affixing the droplet in proximity to the gap.

97. The method of 83, wherein the method includes applying exogenous electromagnetic radiation sufficient to affix the droplet to a specific location on the substrate surface.

98. A method of moving an affixed droplet on a substrate, the method including:
    delivering a droplet in a first carrier fluid from a microfluidic device, through an orifice, to a substrate surface;
    positioning the droplet in a second carrier fluid on the substrate surface;
    affixing the droplet to the substrate surface via a force; and
    modulating the force so as to move the droplet from its affixed location to another location and/or applying a second force, which is sufficient, either alone or in combination with the modulated force, to move the droplet from its affixed location to another location.

99. The method of 98, wherein the first and second carrier fluid are the same.

100. The method of 98 or 99, wherein the substrate includes a plurality of channels filled with a conductive liquid or solid material and an insulating sheet positioned between the plurality of channels and the carrier fluid, wherein the plurality of channels are patterned to generate an electric field gradient above the insulating sheet upon application of a voltage, and wherein the method includes applying a voltage to one or more of the plurality of channels sufficient to generate the electrical field gradient, wherein the electrical field gradient produced a dielectrophoretic force sufficient to affix the droplet to the substrate surface.

101. The method of 100, including modulating the electrical field so as to move the droplet from its affixed location to another location.

102. The method of 98, wherein the method includes applying exogenous electromagnetic radiation sufficient to move the droplet from its affixed location to another location.

103. The method of 98, wherein the method includes introducing a cross flow of fluid which is sufficient to move the droplet from its affixed location to another location.

104. The method of 98, wherein the buoyancy of the droplet in the second carrier fluid is modulated to move the droplet from its affixed location to another location.

105. A method of adding reagents to a droplet, the method including:
    delivering a first droplet in a first carrier fluid from a microfluidic device, through an orifice, to a substrate surface;
    positioning the droplet in a second carrier fluid on the substrate surface;
    affixing the droplet to the substrate surface via a force;
    delivering a second droplet to the same location as the first droplet affixed to the substrate surface or a location adjacent the first droplet on the substrate surface; and
    coalescing the first droplet and the second droplet such that the contents of the first droplet and the second droplet are combined.

106. The method of 105, wherein the first and second carrier fluid are the same.

107. The method of 105 or 106, wherein multiple droplets are delivered to the same location as the first droplet affixed to the substrate surface or a location adjacent the first droplet on the substrate surface, and wherein the multiple droplets are coalesced with the first droplet such that the contents of the first droplet and the multiple droplets are combined.

108. The method of any one of 105-107, wherein coalescence is triggered via application of a force to one or more of the droplets.

109. The method of any one of 105-107, wherein coalescence occurs spontaneously.

110. The method of 108, wherein the force is an electrical force.

111. A method of adding reagents to a droplet, the method including:
    delivering a droplet in a first carrier fluid from a microfluidic device, through a first orifice, to a substrate surface;
    positioning the droplet in a second carrier fluid on the substrate surface;
    affixing the droplet to the substrate surface via a force;
    inserting a second orifice fluidically connected to a reagent source into the droplet; and
    injecting via the second orifice one or more reagents into the droplet.

112. The method of 111, wherein the first and second carrier fluid are the same.

113. A method of affixing a droplet to a substrate, the method including:
- delivering a droplet in a first carrier fluid from a microfluidic device, through an orifice, to a substrate surface;
- positioning the droplet in a second carrier fluid on the substrate surface;
- affixing the droplet to the substrate surface via a force; and
- recovering all or a portion of the affixed droplet.

114. The method of 113, wherein the first and second carrier fluid are the same.

115. The method of 113 or 114, wherein the recovering includes modulating one or more forces acting on the affixed droplet.

116. The method of 113 or 114, wherein the recovering includes contacting the affixed droplet with a microfluidic orifice fluidically connected to a suction device to recover all or a portion of the affixed droplet from the substrate surface.

117. The method of 113 or 114, wherein the recovering includes bringing in proximity to the affixed droplet a microfluidic orifice fluidically connected to a suction device to recover the affixed droplet from the substrate surface.

118. The method of 113 or 114, wherein the recovering includes inserting into the affixed droplet a microfluidic orifice fluidically connected to a suction device to recover all or a portion of the contents of the affixed droplet.

119. The method of 113 or 114, wherein the recovering includes shearing the affixed droplet from the substrate surface.

120. The method of 113 or 114, wherein the recovering includes increasing the buoyancy of the affixed droplet such that buoyancy forces acting on the affixed droplet are sufficient to overcome the force affixing the droplet to the substrate surface, thereby releasing the affixed droplet from the substrate surface.

121. The method of 120, wherein increasing the buoyancy of the affixed droplet includes increasing the volume of the affixed droplet.

122. The method of 121, wherein the volume of the affixed droplet is increased by injecting an aqueous fluid into the affixed droplet.

123. The method of 113 or 114, wherein the recovering includes modulating the force affixing the droplet to the substrate surface such that the droplet is released from the substrate surface.

124. The method of 123, wherein the modulating includes removing the force.

125. The method of 113 or 114, wherein the droplet includes one or more beads.

126. The method of 125, wherein the one or more beads include a binding agent which selectively binds one or more materials present in the droplet.

127. The method of 125 or 126, wherein the one or more beads are buoyant within the droplet.

128. The method of 125 or 126 wherein the one or more beads are selected from magnetic beads and conductive beads.

129. The method of any one of 125-128, including positioning and/or concentrating the one or more beads in a first region of the droplet leaving a second region which is relatively devoid of beads.

130. The method of 129, including selectively recovering from the droplet the one or more beads from the first region.

131. The method of 129, including selectively recovering material from the second region of the droplet.

132. The method of any one of 113-131, including delivering the recovered droplet or the recovered portion of the droplet to one or more isolated containers via a delivery orifice.

133. A method of manipulating an affixed droplet, the method including:
- delivering a droplet in a first carrier fluid from a microfluidic device, through an orifice, to a substrate surface;
- positioning the droplet in a second carrier fluid on the substrate surface;
- affixing the droplet to the substrate surface via a force; and
- modulating the immediate environment of the droplet, thereby modulating the contents of the droplet.

134. The method of 133, wherein the first and second carrier fluid are the same.

135. The method of 133 or 134, wherein the modulating includes modulating a parameter selected from a chemical composition of the immediate environment, a temperature of the immediate environment, a pH of the immediate environment, a pressure of the immediate environment, and a radiation level of the immediate environment.

136. The method of any one of 133-135, wherein the substrate surface is selectively permeable, the substrate includes a fluid volume positioned beneath and in contact with the selectively permeable substrate surface, and the immediate environment of the droplet is modulated by modulating one or more of a chemical composition of the fluid volume, a temperature of the fluid volume, a pH of the fluid volume, a pressure of the fluid volume, and a radiation level of the fluid volume.

137. The method of 136, wherein the fluid volume is a fluid flow.

138. The method of any one of 133-137, wherein the substrate includes patterned electrodes positioned beneath the fluid volume.

139. The method of any one of 133-138, including storing the affixed droplet under controlled environmental conditions for a storage period, wherein the force is maintained during the storage period.

140. The method of 139, wherein the controlled environmental conditions include a constant temperature and/or pressure.

141. The method of any one of 133-140, including at least partially solidifying the affixed droplet.

142. The method of 141, including removing the second carrier fluid from the substrate surface.

143. The method of 142, wherein the second carrier fluid is immiscible with the contents of the affixed droplet prior to the at least partial solidification of the affixed droplet, and wherein the method includes replacing the removed second carrier fluid with a miscible fluid.

144. The method of 143, including modulating a chemical composition of the miscible fluid, thereby modulating the affixed droplet.

145. A method of manipulating an affixed droplet, the method including:
- delivering a droplet in a first carrier fluid from a microfluidic device, through an orifice, to a substrate surface;

positioning the droplet in a second carrier fluid on the substrate surface;
affixing the droplet to the substrate surface via a force;
at least partially solidifying the affixed droplet;
removing the second carrier fluid from the substrate surface, wherein the second carrier fluid is immiscible with the contents of the affixed droplet prior to the at least partial solidification of the affixed droplet;
replacing the removed second carrier fluid with a miscible fluid; and modulating a chemical composition of the miscible fluid, thereby modulating the affixed droplet.

146. The method of 145, wherein the first and second carrier fluid are the same.

147. A method of porating a cell within an affixed droplet, the method including:
delivering a droplet in a first carrier fluid from a microfluidic device, through an orifice, to a substrate surface, wherein the droplet includes a cell;
positioning the droplet in a second carrier fluid on the substrate surface;
affixing the droplet to the substrate surface via a force; and
porating the cell within the droplet.

148. The method of 147, wherein the first and second carrier fluid are the same.

149. The method of 147 or 148, wherein the cell is porated using electrical, chemical, or sonic means.

150. The method of any one of 147-148, including introducing one or more nucleic acids into the porated cell.

151. The method of any one of 147-150, wherein the poration occurs within the microfluidic device.

152. The method of any one of 147-150, wherein the poration occurs after delivery through the orifice and prior to affixing the droplet to the substrate surface.

153. The method of any one of 147-150, wherein the poration occurs after the droplet is affixed to the substrate surface.

154. The method of any one of 147-149, wherein the poration occurs in the microfluidic device prior to delivery through the orifice.

155. The method of 154, wherein the droplet is delivered to the substrate surface in proximity to a second droplet positioned on the substrate surface, wherein the second droplet includes a nucleic acid, and wherein the method includes merging the droplet with the second droplet to contact the nucleic acid with the porated cell.

156. A method of analyzing a droplet on a substrate, the method including:
delivering a droplet in a first carrier fluid from a microfluidic device, through an orifice, to a substrate surface;
positioning the droplet in a second carrier fluid on the substrate surface;
affixing the droplet to the substrate surface via a force; and
detecting one or more components of the affixed droplet.

157. The method of 156, wherein the first and second carrier fluid are the same.

158. The method of 156 or 157, wherein the detecting is performed at a plurality of time points.

159. The method of 156 or 157, wherein the method includes continuously detecting the one or more components of the affixed droplet over a period of time.

160. The method of 158 or 159, wherein the method includes detecting a change in the one or more components of the affixed droplet.

161. The method of any one of 156-160, wherein the detecting includes optically detecting the one or more components of the affixed droplet.

162. The method of 161, wherein the optically detecting includes detecting an absorbance of the one or more components of the affixed droplet.

163. The method of 161, wherein the optically detecting includes detecting a fluorescence of the one or more components of the affixed droplet.

164. The method of any one of 156-160, wherein the detecting includes detecting the one or more components of the affixed droplet via one or more spectroscopic techniques.

165. The method of 164, wherein the one or more spectroscopic techniques are selected from nuclear magnetic resonance (NMR) spectroscopy, UV spectroscopy, and mass spectrometry.

166. The method of any one of 156-160, wherein the method includes adding a suitable matrix-assisted laser desorption/ionization (MALDI) matrix material to the droplet either before or after fixation, and detecting one or more components of the affixed droplet via MALDI.

167. The method of any one of 156-165, including recovering and analyzing all or a portion of the affixed droplet.

168. A method of delivering discrete entities to a substrate, the method including:
flowing a plurality of first discrete entities through a first microfluidic device in a first carrier fluid, wherein the first discrete entities are insoluble and/or immiscible in the first carrier fluid, and wherein the first microfluidic device includes a first delivery orifice;
directing the first carrier fluid and one or more of the plurality of first discrete entities through the first delivery orifice to the substrate;
flowing a plurality of second discrete entities through a second microfluidic device in a second carrier fluid, wherein the second discrete entities are insoluble and/or immiscible in the second carrier fluid, and wherein the second microfluidic device includes a second delivery orifice;
directing the second carrier fluid and one or more of the plurality of second discrete entities through the second delivery orifice to the substrate; and
affixing the one or more of the plurality of first discrete entities and the one or more of the plurality of second discrete entities to the substrate.

169. The method of 168, wherein the first discrete entities and/or the second discrete entities are droplets.

170. The method of 169, wherein the droplets include an aqueous fluid, which is immiscible with the first carrier fluid and the second carrier fluid.

171. The method of 170, wherein the substrate includes on a first surface a layer of fluid which is miscible with the carrier fluid and immiscible with the aqueous fluid, and wherein the droplets are affixed to the first surface of the substrate following introduction into the layer of fluid on the first surface of the substrate.

172. The method of 169, wherein the first carrier fluid and the second carrier fluid are aqueous fluids and the droplets include a fluid which is immiscible with the first carrier fluid and the second carrier fluid.

173. The method of 172, wherein the substrate includes on a first surface a layer of aqueous fluid which is miscible with the first carrier fluid and the second carrier fluid and immiscible with the fluid included by the droplets, and wherein the droplets are affixed to the first surface of the substrate following introduction into the layer of aqueous fluid on the first surface of the substrate.

174. The method of any one of 168-173, wherein the first carrier fluid and the second carrier fluid are the same.

175. The method of any one of 168-174, wherein the first microfluidic device and the second microfluidic device are integrated with an automated system which selectively positions the delivery orifices relative to the substrate, and wherein the method includes selectively positioning via the automated system the delivery orifices relative to the substrate to selectively deliver the plurality of first discrete entities and the plurality of second discrete entities to one or more locations on or in proximity to the substrate.

176. The method of any one of 168-174, wherein the first microfluidic device and the second microfluidic device are integrated with an automated system which selectively positions the substrate relative to the delivery orifices, and wherein the method includes selectively positioning via the automated system the substrate relative to the delivery orifices to selectively deliver the plurality of first discrete entities and the plurality of second discrete entities to one or more locations on or in proximity to the substrate.

177. A method of delivering discrete entities to a substrate, the method including:
 flowing a plurality of discrete entities through a microfluidic device in a carrier fluid, wherein the discrete entities are insoluble and/or immiscible in the carrier fluid, and wherein the microfluidic device includes a plurality of delivery orifices;
 directing the carrier fluid and a first one or more of the plurality of discrete entities through a first delivery orifice of the plurality of delivery orifices to the substrate;
 directing the carrier fluid and a second one or more of the plurality of discrete entities through a second delivery orifice of the plurality of delivery orifices to the substrate; and
 affixing the first one or more of the plurality of first discrete entities and the second one or more of the plurality of discrete entities to the substrate.

178. The method of 177, wherein the discrete entities are droplets.

179. The method of 178, wherein the droplets include an aqueous fluid, which is immiscible with the carrier fluid.

180. The method of 179, wherein the substrate includes on a first surface a layer of fluid which is miscible with the carrier fluid and immiscible with the aqueous fluid, and wherein the droplets are affixed to the first surface of the substrate following introduction into the layer of fluid on the first surface of the substrate.

181. The method of 178, wherein the carrier fluid is an aqueous fluid and the droplets include a fluid which is immiscible with the carrier fluid.

182. The method of 181, wherein the substrate includes on a first surface a layer of aqueous fluid which is miscible with the carrier fluid and immiscible with the fluid included by the droplets, and wherein the droplets are affixed to the first surface of the substrate following introduction into the layer of aqueous fluid on the first surface of the substrate.

183. The method of any one of 177-182, wherein the microfluidic device is integrated with an automated system which selectively positions the delivery orifices relative to the substrate, and wherein the method includes selectively positioning via the automated system the delivery orifices relative to the substrate to selectively deliver the first one or more of the plurality of discrete entities and the second one or more of the plurality of discrete entities to one or more locations on or in proximity to the substrate.

184. The method of any one of 177-182, wherein the microfluidic device is integrated with an automated system which selectively positions the substrate relative to the delivery orifices, and wherein the method includes selectively positioning via the automated system the substrate relative to the delivery orifices to selectively deliver the first one or more of the plurality of discrete entities and the second one or more of the plurality of discrete entities to one or more locations on or in proximity to the substrate.

185. A method of analyzing a droplet, the method including:
 flowing a plurality of droplets through a microfluidic device in a carrier fluid,
 encapsulating or incorporating unique identifier molecules into the plurality of droplets, such that each droplet of the plurality of droplets includes a different unique identifier molecule;
 delivering the plurality of droplets in a first carrier fluid from a microfluidic device, through an orifice, to a substrate surface;
 positioning the plurality of droplets in a second carrier fluid on the substrate surface;
 affixing the plurality of droplets to the substrate surface via a force;
 for each of the affixed plurality of droplets, recovering all or a portion of the affixed droplet and the unique identifier for each droplet;
 analyzing the recovered droplets or recovered portions thereof in conjunction with the unique identifier, wherein results of the analysis are identified as specific to material originating from particular droplets based on the presence of the unique identifier.

186. The method of 185, wherein the first carrier fluid and the second carrier fluid are the same.

187. The method of 185, wherein the unique identifier molecules specifically bind to one or more materials present in the plurality of droplets.

188. The method of 185, wherein no two droplets include the same unique identifier molecule.

189. The method of 185, wherein the unique identifier molecules include nucleic acids.

190. The method of 189, wherein the plurality of droplets include nucleic acid molecules, one or more of the unique identifier molecules are covalently bound to the nucleic acid molecules, and wherein the method includes sequencing the nucleic acid molecules together with the unique identifier molecules, wherein the presence of the sequence of a unique identifier molecule in the sequence read of a nucleic acid molecule identifies the nucleic acid molecule as originating from a particular droplet.

191. A method of performing quantitative PCR, the method including:

partitioning a heterogeneous population of nucleic acids into a plurality of droplets including an aqueous fluid;

encapsulating or incorporating quantitative PCR reagents into the plurality of droplets;

flowing the plurality of droplets through a microfluidic device in a carrier fluid, wherein the carrier fluid is immiscible with the aqueous fluid;

directing the carrier fluid and a plurality of droplets through a delivery orifice to a substrate;

affixing the plurality of droplets to the substrate, wherein the substrate includes on a first surface a layer of fluid which is miscible with the carrier fluid and immiscible with the aqueous fluid, and wherein the plurality of droplets are affixed to the first surface of the substrate following introduction into the layer of fluid on the first surface of the substrate;

incubating the affixed plurality of droplets under conditions sufficient for amplification of nucleic acids; and detecting nucleic acid amplification over time.

192. The method of 191, wherein the encapsulating or incorporating step occurs subsequent to the affixing step.

193. The method of 191 or 192, wherein the heterogeneous population of nucleic acids is included by a plurality of cells, and wherein the partitioning includes partitioning the plurality of cells into the plurality of droplets including an aqueous fluid.

194. The method of 193, wherein the method includes separate cell lysis and nucleic acid amplification steps.

195. A method of sequencing single cell nucleic acids, the method including:

partitioning a heterogeneous plurality of cells into a plurality of droplets including an aqueous fluid, such that each droplet includes not more than one cell;

subjecting the plurality of droplets to conditions sufficient for lysis of the cells contained therein and release of cellular nucleic acids;

encapsulating or incorporating unique nucleic acid identifier molecules into the plurality of droplets, such that each droplet of the plurality of droplets includes a different unique nucleic acid identifier molecule;

linking the unique nucleic acid identifier molecules to one or more cellular nucleic acids in the plurality of droplets or to amplification products thereof;

flowing the plurality of droplets through a microfluidic device in a first carrier fluid;

delivering the plurality of droplets in the first carrier fluid from the microfluidic device, through an orifice, to a substrate surface;

positioning the plurality of droplets in a second carrier fluid on the substrate surface;

affixing the plurality of droplets to the substrate surface via a force;

for each of the affixed plurality of droplets, recovering all or a portion of the affixed droplet, including cellular nucleic acids and the unique nucleic acid identifier for each droplet;

sequencing nucleic acids from the recovered droplets or recovered portions thereof together with the unique identifier molecules, wherein the presence of the sequence of a unique identifier molecule in the sequence read of a nucleic acid molecule identifies the nucleic acid molecule as originating from a particular cell.

196. The method of 195, wherein the subjecting step occurs subsequent to the affixing step.

197. The method of 195, wherein the encapsulating or incorporating step and the linking step occur subsequent to the affixing step.

198. The method of any one of 195-197, wherein the method includes separate cell lysis, nucleic acid amplification, and linking steps.

199. A method of synthesizing a polymer on a substrate, the method including:

flowing a first droplet including a first droplet fluid through a microfluidic device in a carrier fluid, wherein the first droplet includes a first polymer or a first monomer;

directing the carrier fluid and the first droplet through a delivery orifice to the substrate;

affixing the first droplet to the substrate wherein the substrate includes on a first surface a layer of fluid which is miscible with the carrier fluid and immiscible with the first droplet fluid, and wherein the first droplet is affixed to the first surface of the substrate at a predetermined location following introduction into the layer of fluid on the first surface of the substrate;

flowing a second droplet through the microfluidic device in the carrier fluid, wherein the second droplet includes a second polymer or a second monomer;

directing the carrier fluid and the second droplet through the delivery orifice to the first droplet affixed at the predetermined location;

incubating the first and second droplets under conditions sufficient for the contents of the first and second droplets to come into contact and for the first polymer or first monomer to form a covalent bond with the second polymer or monomer, thereby generating a synthesized polymer.

200. The method of 199, wherein the incubating includes incubating the first and second droplets under conditions sufficient for droplet coalescence.

201. The method of 199 or 200, wherein the synthesized polymer is a polypeptide.

202. The method of 199 or 200, wherein the synthesized polymer is a nucleic acid.

203. A method of analyzing a droplet on a substrate, the method including:

partitioning a molecular library including a plurality of library members into a plurality of droplets including an aqueous fluid;

delivering the plurality of droplets in a first carrier fluid from a microfluidic device, through an orifice, to a substrate surface;

positioning the droplets in a second carrier fluid on the substrate surface;

affixing the droplets to the substrate surface via a force; and performing one or more reactions in the affixed droplets with the library members;

detecting the results of the one or more reactions in the affixed droplets and/or recovering all or a portion of the affixed droplets for further analysis.

204. The method of 203, wherein the first and second carrier fluid are the same.

205. A method of printing microarrays, the method including:

delivering a plurality of droplets in a first carrier fluid from a microfluidic device, through an orifice, to a substrate surface, wherein each of the plurality of droplets includes a molecule;
positioning the droplets in a second carrier fluid on the substrate surface;
affixing the droplets at predetermined locations to the substrate surface via a force;
incubating the substrate under conditions suitable for chemical bonding of the molecules included by the affixed droplets to the substrate surface, thereby providing an array of substrate-bound molecules.

206. The method of 205, wherein the first and second carrier fluid are the same.

207. A method of in situ sequencing, the method including:
flowing a plurality of droplets through a microfluidic device in a carrier fluid,
encapsulating or incorporating unique nucleic acid identifier molecules into the plurality of droplets, such that each droplet of the plurality of droplets includes one or more copies of a different unique nucleic acid identifier molecule;
delivering the plurality of droplets in a first carrier fluid from a microfluidic device, through an orifice, to a surface of a tissue substrate;
positioning the plurality of droplets in a second carrier fluid on the surface of the tissue substrate;
affixing the plurality of droplets to the surface of the tissue substrate via a force;
incubating the tissue substrate under conditions sufficient for the unique nucleic acid identifier molecules from each affixed droplet to bind to nucleic acids contained within the tissue substrate in proximity to the affixed droplet;
sequencing the unique nucleic acid identifier molecules and the nucleic acids to which they are bound; and
identifying and/or quantitating, using the unique nucleic acid identifier molecules, nucleic acids contained within the tissue substrate at locations corresponding to locations where particular droplets were affixed.

208. The method of 207, wherein the first and second carrier fluid are the same.

209. A method of manipulating cells or embryos, the method including:
flowing a plurality of droplets through a microfluidic device in a carrier fluid, wherein each droplet of the plurality of droplets includes an aqueous fluid and a fertilized egg cell or embryo, and wherein the carrier fluid is immiscible with the aqueous fluid;
directing the carrier fluid and the plurality of droplets through a delivery orifice to a substrate;
affixing the plurality of droplets to the substrate, wherein the substrate includes on a surface thereof a layer of fluid which is miscible with the carrier fluid and immiscible with the aqueous fluid, and wherein the plurality of droplets is affixed to the surface of the substrate following introduction into the layer of fluid on the surface of the substrate;
detecting within the affixed plurality of droplets the development of one or more embryos; and
selecting and recovering an embryo from the affixed droplets.

210. A method of manipulating cells or embryos, the method including:
flowing a plurality of droplets through a microfluidic device in a carrier fluid, wherein each droplet of the plurality of droplets includes an aqueous fluid and an unfertilized egg cell, and wherein the carrier fluid is immiscible with the aqueous fluid;
directing the carrier fluid and the plurality of droplets through a delivery orifice to a substrate;
fertilizing one or more of the egg cells in the plurality of droplets;
affixing the plurality of droplets to the substrate, wherein the substrate includes on a surface thereof a layer of fluid which is miscible with the carrier fluid and immiscible with the aqueous fluid, and wherein the plurality of droplets are affixed to the surface of the substrate following introduction into the layer of fluid on the surface of the substrate;
detecting within the affixed droplets the development of an embryo; and
selecting and recovering specific embryos from the affixed droplets.

211. The method of 210, wherein the fertilizing occurs after the affixing.

212. A droplet printer including:
a microfluidic device including one or more droplet makers and one or more flow channels, wherein the one or more flow channels are fluidically connected to the one or more droplet makers and configured to receive one or more droplets therefrom;
a delivery orifice fluidically connected to one or more of the one or more flow channels; and
an automated system integrated with the delivery orifice, wherein the automated system (a) selectively positions the delivery orifice in proximity to a substrate during operation or (b) selectively positions the substrate in proximity to the delivery orifice during operation, such that a droplet can be ejected from the delivery orifice and deposited on the substrate.

213. The droplet printer of 212, wherein the microfluidic device includes a droplet sorter which selectively sorts droplets in one or more of the one or more flow channels for delivery through the delivery orifice.

214. The droplet printer of 212 or 213, wherein the microfluidic device includes or is integrated with a temperature control module which is capable of modulating the temperature of a carrier fluid in the one or more flow channels.

215. The droplet printer of 214, wherein the temperature control module is a thermal cycler.

216. The droplet printer of any one of 212-215, including a detection means capable of detecting one or more droplets or one or more droplet components in one or more of the one or more flow channels.

217. The droplet printer of 216, wherein the detection means is an optical imager.

218. The droplet printer of any one of 212-217, wherein the sorter includes a flow channel including a gapped divider including a separating wall which extends less than the complete height of the flow channel.

219. A system including:
a droplet printer as set forth in any one of 212-217;
a substrate surface for receiving one or more droplets deposited by the delivery orifice of the droplet printer; and
one or more of:
(a) a temperature control module operably connected to the droplet printer,
(b) a detection means operably connected to the droplet printer, (c) an incubator operably connected to the droplet printer, and (d) a sequencer operably connected to the droplet printer; and a conveyor configured to convey the substrate from a first droplet receiving position to one or more of (a)-(d).

220. A substrate including:

a substrate surface including an immiscible phase fluid; and an ordered array of droplets positioned in the immiscible phase fluid, wherein the droplets are affixed to the substrate surface, and wherein the ordered array of droplets includes at least 10,000 individual droplets.

221. The substrate of 220, wherein the ordered array of droplets includes at least 50,000 individual droplets.

222. The substrate of 221 wherein the ordered array of droplets includes at least 100,000 individual droplets.

223. The substrate of 221 wherein the ordered array of droplets includes at least 1,000,000 individual droplets.

224. The substrate of any one of 220-223, wherein the substrate has a length of 128 mm or less and a width of 85 mm or less.

225. An electrode array system including:

an array of individually controllable electrodes embedded in a substrate material;

a power source; and a controller, wherein the controller is configured to selectively enable or disable an electrical connection between the power source and each individually controllable electrode in the array thereby providing an active or inactive electrode respectively, and wherein, each active electrode is capable of affixing a discrete entity to a surface of the substrate material in proximity to the active electrode when said discrete entity is deposited in proximity to the active electrode.

226. The method of any one of 1-39, wherein one or more of the plurality of discrete entities includes a plurality of materials, and wherein the method includes subjecting one or more of the affixed discrete entities including the plurality of materials to conditions sufficient for assembly of the plurality of the materials.

227. The method of 226, wherein the plurality of materials includes a plurality of microparticles and/or nanoparticles.

228. The method of 226, wherein the plurality of materials includes one or more metals.

229. The method of 226, wherein the plurality of materials includes one or more semiconductor materials.

230. The method of 226, wherein the plurality of materials includes one or more organic materials.

231. The method of 226, wherein the plurality of materials includes one or more nucleic acids.

232. The method of 226, wherein the plurality of materials includes one or more hydrogel materials.

233. The method of 226, wherein the plurality of materials includes one or more liquid materials.

234. The method of 226, wherein the plurality of materials includes one or more materials having a shape selected from a sphere, a rod, a polyhedron, or a star.

235. The method of 226, wherein the plurality of materials includes one or more materials having a surface coating.

236. The method of 235, wherein the surface coating is selected from a charged coating, a hydrophilic coating, a hydrophobic coating, and a coating including one or more molecular recognition elements.

237. The method of 226, wherein the plurality of materials includes one or more monomers and/or polymers.

238. The method of any one of 226-237, wherein the assembly includes one or more covalent bonding interactions between the plurality of materials.

239. The method of any one of 226-237, wherein the assembly includes one or more non-covalent bonding interactions between the plurality of materials.

240. The method of any one of 226-239, wherein subjecting the one or more of the affixed discrete entities including the plurality of materials to conditions sufficient for assembly of a plurality of the materials includes exposing the one or more of the affixed discrete entities including the plurality of materials to light, an increase or decrease in temperature, a magnetic force, an electric field (e.g., a frequency modulated electric field), a catalyst, an enzyme (e.g., an enzyme catalyst), a depletion force, and/or conditions sufficient for self-assembly of the plurality of materials.

241. The method of any one of 226-240, including screening the assembled materials for one or more properties.

242. The method of 241, wherein the one or more properties are selected from conductivity; interactions with electromagnetic radiation, e.g., visible light, UV or IR, such as index of refraction or light scattering; fluorescence; magnetic properties; interactions, e.g., binding interactions, with biological components or entities (e.g., cells (e.g., bacteria or mammalian), fungi, or viruses); catalytic properties; buoyancy; and density.

243. A microfluidic device including:

an inlet channel;

a first outlet channel in fluid communication with the inlet channel;

a second outlet channel in fluid communication with the inlet channel;

a dividing wall separating the first outlet channel from the second outlet channel, wherein the dividing wall includes a first proximal portion having a height which is less than the height of the inlet channel and a second distal portion having a height which is equal to or greater than the height of the inlet channel.

244. The microfluidic device of 243, including an electrode configured to selectively apply an electric field in the inlet channel upstream of the dividing wall.

245. The microfluidic device of 243 or 244, wherein the height of the first proximal portion is from about 10% to about 90% of the height of the inlet channel.

246. The microfluidic device of any one of 243-245, wherein the length of the first proximal portion is equal to or greater than the diameter of a microdroplet to be sorted by the microfluidic device.

247. The microfluidic device of 246, wherein the length of the first proximal portion is from about 1× to about 100× of the diameter of a microdroplet to be sorted by the microfluidic device.

248. The microfluidic device of 247, wherein the length of the first proximal portion is from about 20× to about 30× of the diameter of a microdroplet to be sorted by the microfluidic device.

249. The microfluidic device of any one of 243-248, including a collection reservoir in fluid communication with the first outlet channel and a waste reservoir in fluid communication with the second outlet channel.

250. A system including a microfluidic device as set forth in any one of 244-249, and an optical detector configured to detect an optical property of one or microdroplets in the inlet channel upstream of the location of the application of the electric field by the electrode.

251. A method of sorting microdroplets, the method including:
flowing a plurality of microdroplets through an inlet channel of a microfluidic device in a carrier fluid;
detecting via a detector a property of one or more of the plurality of microdroplets in the inlet channel;
applying an electric field to the inlet channel to selectively deflect one or more of the plurality of microdroplets into a first outlet channel in fluid communication with the inlet channel or a second outlet channel in fluid communication with the inlet channel based on the detection of the property, wherein the microfluidic device includes a dividing wall separating the first outlet channel from the second outlet channel, wherein the dividing wall includes a first proximal portion having a height which is less than the height of the inlet channel and a second distal portion having a height which is equal to or greater than the height of the inlet channel.

252. The method of 251, wherein the property is an optical property.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); and the like.

Figure 8:
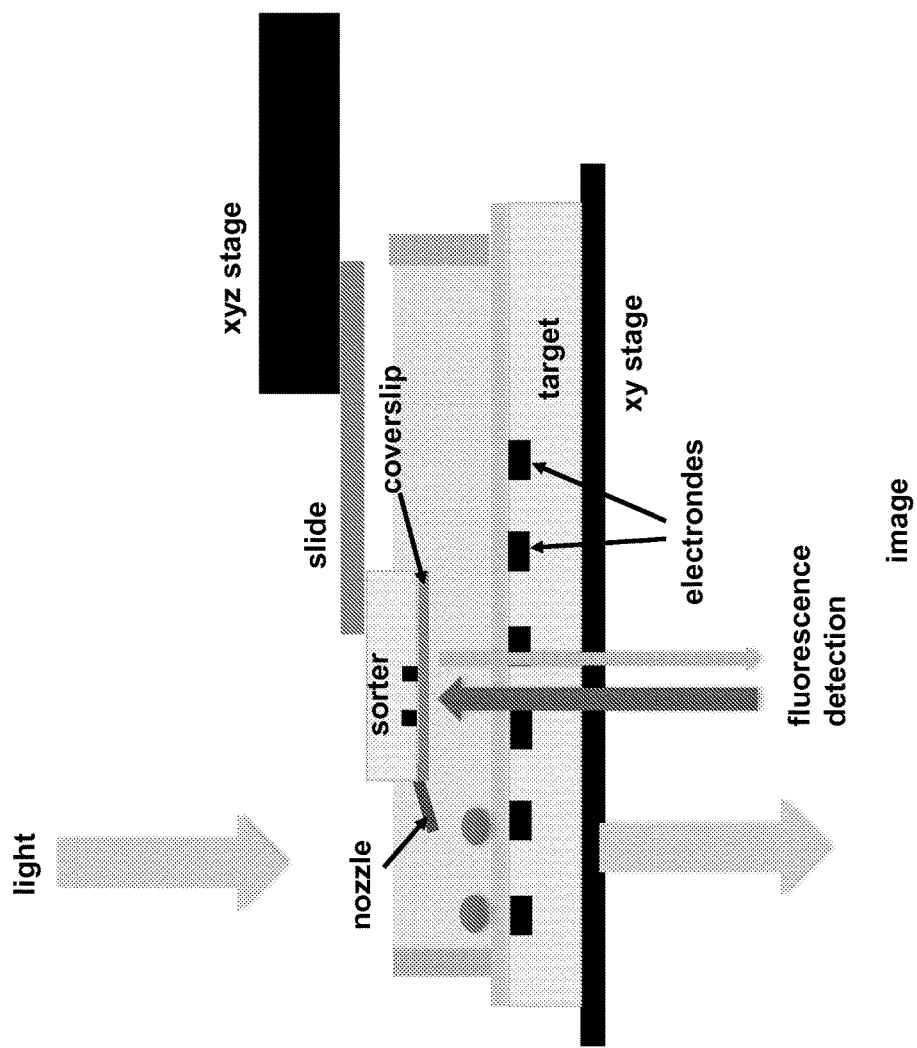
FIG. 8 provides a schematic of a system according to the present disclosure. A droplet microfluidic print head, including a compact microfluidics droplet sorter modified with an exit nozzle, is suspended above the stage of an inverted microscope. Droplets flowing through the sorter are fluorescently labeled and detected within the device by a laser coupled to external detection optics. When a desired droplet is detected, it is actively sorted to the nozzle and directed to a target surface. A constant background flow of carrier fluid (e.g., oil) brings the droplet in close contact with the dielectrophoretic trap. A customized substrate with biopolar electrodes patterned into its surface is placed on the xy stage of the microscope and serves as a target for the deposition of droplets. Specific regions on the substrate with high electric field gradients serve as dieletrophoretic traps for droplets by causing movement of droplets towards, and wetting onto these regions. In this implementation, the nozzle of the print head is held stationary, while the substrate is translated horizontally.

Example 1: Fabrication and Testing of Microfluidic Nozzle and Patterned Electrode Substrate A microdroplet printing system was built and tested using the scheme displayed in FIG. 8. A droplet microfluidic print head, including a compact microfluidics droplet sorter modified with an exit nozzle, is suspended above the stage of an inverted microscope. Droplets flowing through the sorter are fluorescently labeled and detected within the device by a laser coupled to external detection optics. When a desired droplet is detected, it is actively sorted to the nozzle and directed to a target surface. A constant background flow of carrier fluid (oil) brings the droplet in close contact with the dielectrophoretic trap. A customized substrate with biopolar electrodes patterned into its surface is placed on the xy stage of the microscope and serves as a target for the deposition of droplets. Specific regions on the substrate with high electric field gradients serve as dieletrophoretic traps for droplets by causing movement of droplets towards, and wetting onto these regions. In this implementation, the nozzle of the print head is held stationary, while the substrate is translated horizontally.

Figure 9:
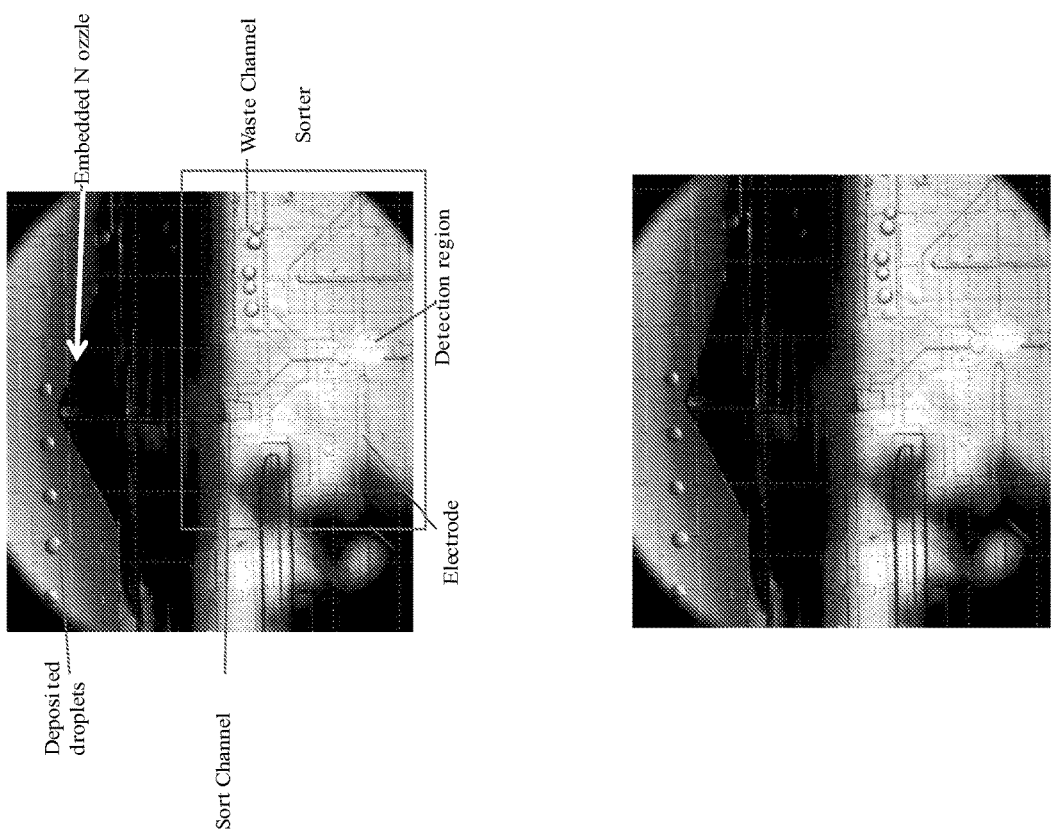
FIG. 9 provides an image from a droplet printing example. The print head and the network of dielectrophoretic traps are visible and in the plane of the image. A series of droplets printed to the surface are visible along the top of the image.

FIG. 9 shows preliminary results from a droplet printing example. The print head and the network of dielectrophoretic traps are visible and in the plane of the image. A series of droplets printed to the surface are visible along the top of the image.

Construction of the Microfluidic Print Head:

The microfluidic print head contains a modified version of a dielectrophoresis-actuated sorter. The sorter used is this example is designed to sort droplets with approximately 80 μm diameters. The sorter geometry is molded in PDMS using soft lithography techniques known in the art. The device geometry is trimmed down to a 2 cm×2 cm square, punched for fluidic access, and plasma bonded to a glass coverslip. The "sort" exit of the sorter is coupled to a lateral exit from the device. A 250 μm OD/125 μm ID polyethylene tube is inserted into this exit channel and glued in place using two part epoxy, creating a nozzle to direct droplets towards the printing substrate. The top surface of the sorter is plasma bonded to a 1"×3" glass slide to enable anchoring of the sorter to a xyz micromanipulator. This micromanipulator enables the placement of the tip of the print nozzle within 100 μm of the printing substrate surface.

Figure 4:
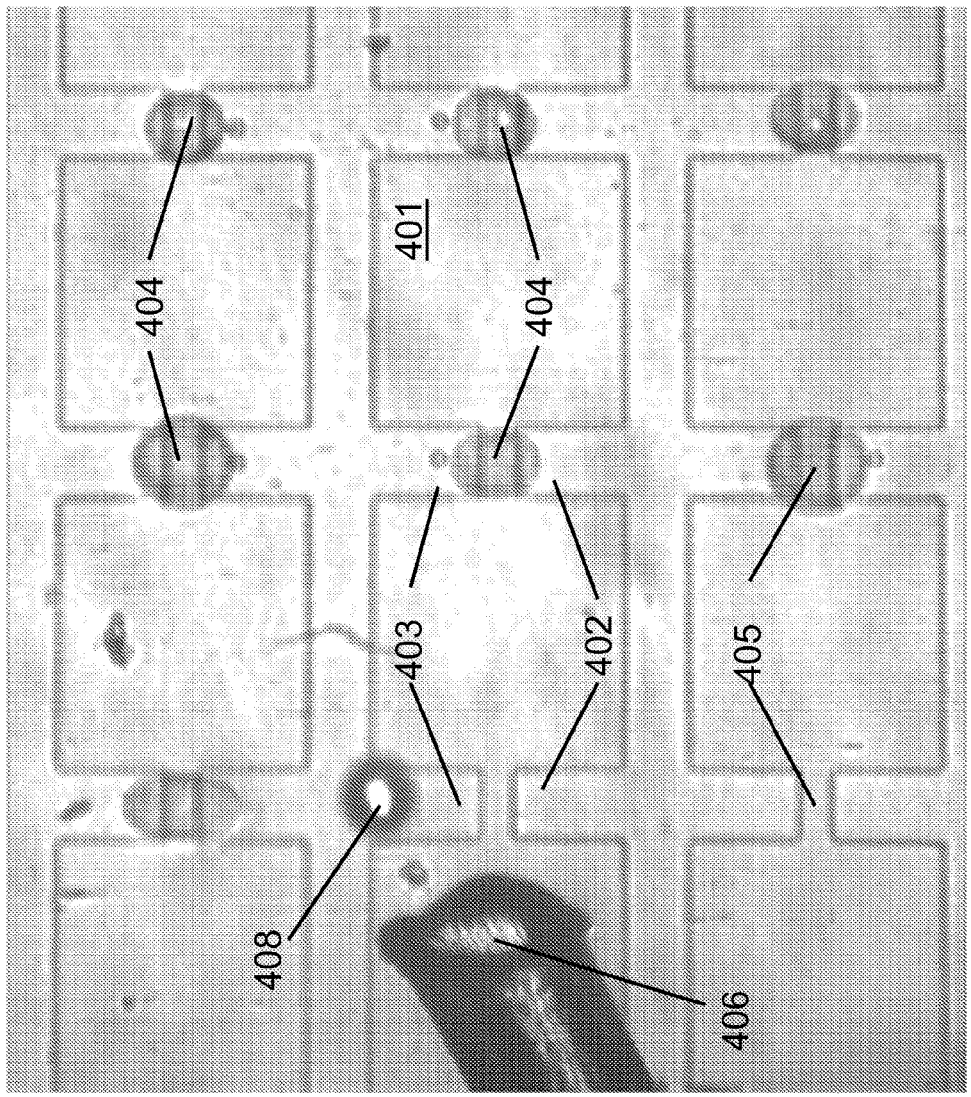
FIG. 4 illustrates aspects of the subject devices and methods including a substrate designed with electrode geometry configured to impart high electric field gradients on the surface of the substrate, creating dielectrophoretic forces that pull droplets towards the substrate surface. An exemplary device depositing aqueous droplets on the substrate surface is shown. After contact with the surface, the application of electric fields destabilizes the thin film of immiscible carrier fluid, e.g., oil, separating the aqueous droplets from the substrate surface, causing the droplets to wet the surface. Once wetted, droplets further flatten in a manner that correlates to the applied dielectrophoretic force. High electric field gradients are created by geometries where charged features are separated by small distances. This can be created by exciting one feature with an AC signal and grounding the counter-feature. If the counter-feature is not grounded, high electric field gradients may still be generated because electromagnetic screening (charge reorganization) in the counter-feature causes it to act similarly to a grounded channel.

Fabrication of the Printing Substrate:

The printing substrate includes two paired networks of electrodes that produce a grid of dielectrophoretic traps on a planar surface as shown in FIG. 4. The electrodes are saltwater filled channels, electrified by an external power source, a scheme that has been shown to be effective in dielectrophoretic-based microfluidics devices. The network of electrodes shown in FIG. 4 is molded in PDMS, using standard soft lithography techniques. The device is punched for fluidic access and plasma bonded onto a glass slide with the molded geometric features facing up. The channels are then sealed from the top with a 25 μm thick piece of kapton tape. This sealing film should generally be relatively thin, since the magnitude of the electric field, and therefore the size of the dielectrophoretic force diminish with distance from the electrified features. A rim of silicone caulking is deposited on the surface of the sealed device to maintain a thin layer of oil on top of the dielectrophoretic trap array. When the substrate is in use, the sealed channels are filled with saltwater via pressurized syringes. An AC generator taken from a fluorescent lamp ballast is attached to the syringe needles, and is used to apply about 1500 V at 30,000 Hz AC to the saltwater channels.

Preliminary Experiments:

Proof of concept experiments for the microdroplet printer were performed to demonstrate the function of a microfluidic sorter based print head in combination with a dielectrophoretic trap substrate. An external dropmaker was used to create an emulsion composed of 80 μm aqueous droplets in oil. The aqueous phase included PBS dyed with 40 μM fluorescein dye. The emulsion was reinjected into the print head using a syringe pump. Specialized software was developed to use the sorter as a drop on demand device, where a droplet with a desired set of fluorescent properties can be sorted to the print nozzle when a button within the software interface is manually pressed. After a sorted drop was affixed to the print substrate, the xy stage of the inverted microscope was moved manually to the next grid location. The droplets in FIG. 9 were printed using this technique, demonstrating the feasibility of this printing technology.

Example 2: Improved Sorting Architecture for High-Speed Sorting of Microdroplets Described herein is a microfluidic design that permits 30 kHz droplet sorting with >99% accuracy. This tenfold rate increase compared to the fastest available droplet sorters enables ~108 droplets to be sorted per hour and over a billion per day. Indeed, with the described architecture, sorting speed is not limited by the physical mechanism of sorting (even at Ca ~1) but rather by the electronics that detect the droplets; with faster electronics, even faster sorting is anticipated.

The devices were fabricated using soft lithography of poly(dimethylsiloxane) (PDMS) moulded from device masters. The masters were created from two sequential layers (11 μm and 19 μm thick) of photoresist (MicroChem, SU-8 3010) spun onto a silicon wafer. Uncured PDMS consisting of a 10:1 polymer to cross-linker mixture (Dow Corning, Sylgard 184) was poured onto the master, degassed, and baked at 85° C. for 2 hours. The PDMS mould was then cut and peeled from the master, punched with a 0.75 mm Harris Uni-core for inlet ports, and plasma bonded to a 1 mm thick, 10:1 PDMS slab to ensure a strong bond. The bonded PDMS device was then baked at 85° C. for 10 min. The bottom of the all-PDMS device was then plasma bonded to a glass slide to provide structural support and rigidity. To enable immediate usage of the device with water-in-oil emulsions, a hydrophobic surface treatment was performed by flushing with Aquapel, clearing with pressurized air and baking at 85° C. for an additional 30 min.

Figure 10:
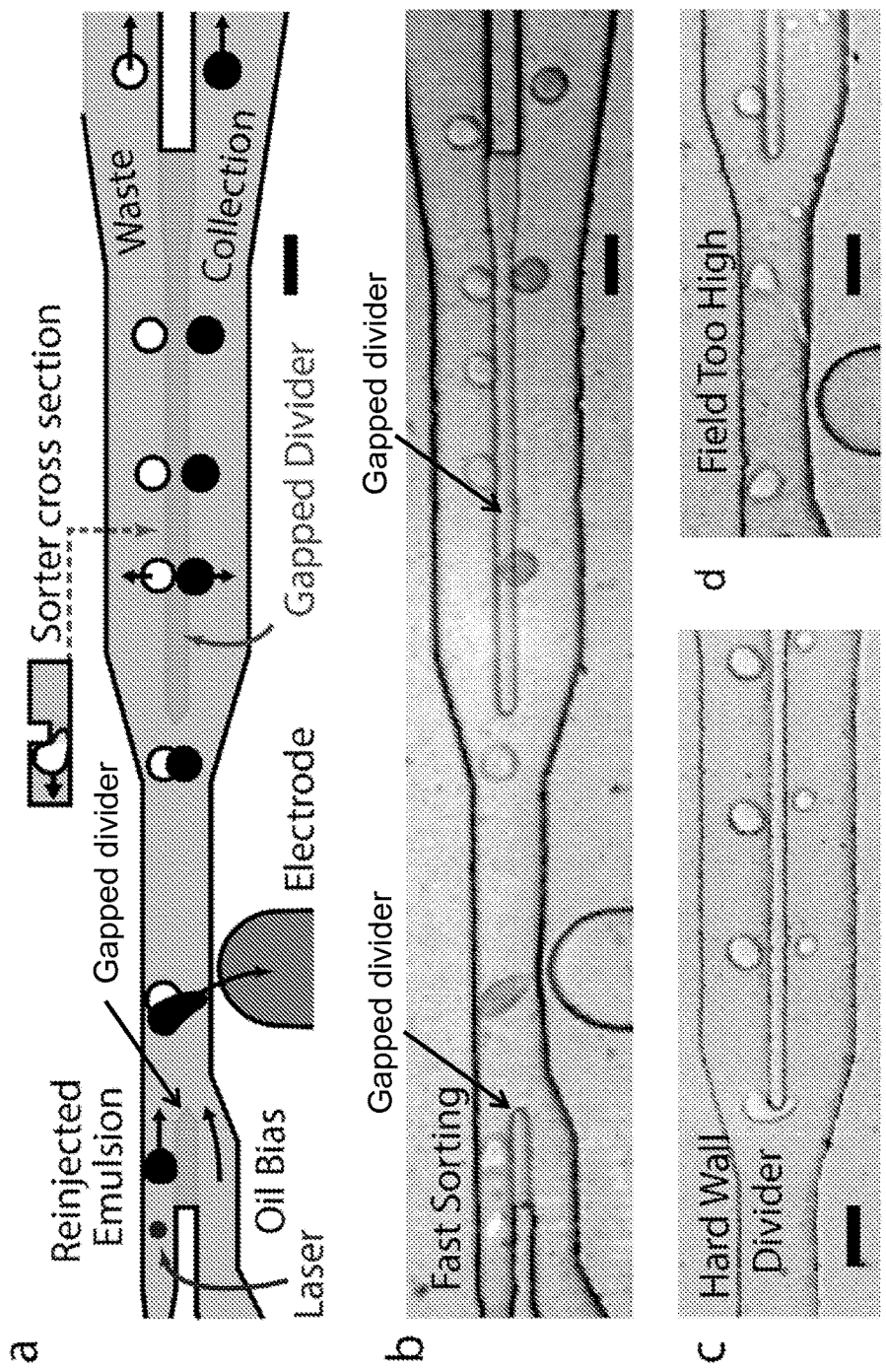
FIG. 10, Panels A-C, provide (a) a schematic of a droplet sorter according to an embodiment of the present disclosure with detected and selectively displaced black droplets being separated by a gapped divider of reduced channel height. (b) Still from high speed video of 22 kHz sorting. With a conventional hard wall divider, droplets not fully displaced are split (c), while larger applied dielectrophoretic forces pull droplets apart (d). Scale bars are 50 µm.

The primary innovation that allows for the increase in sorting speed by over an order of magnitude is the replacement of the impermeable wall that usually divides the collection and waste channels with a gapped divider. The gapped divider, which reaches only part way from the channel ceiling to floor, allows droplets to squeeze into an energetically unfavourable region (11 μm tall) between the sort channels (30 μm tall). Due to the droplet Laplace pressure, small lateral displacements above or below the sorter centre line grow as the droplets travel downstream, pushing them fully into the nearest channel. The process is shown in the schematic of FIG. 10, Panel (a), with a cross section of the squeezed drop in the gapped divider inset. It is also depicted in the still in FIG. 10, Panel (b) taken from a high speed movie of 25 μm droplets sorted at 22 kHz. This is ten-fold faster than conventional sorters, which use hard wall dividers that split droplets at similar flow rates due to shear at the divider edge (FIG. 10, Panel (c)). Splitting does not occur if droplets are displaced sufficiently beyond the divider before they reach its starting edge; however, at high flow rates, the large electric fields utilized break the droplets apart (FIG. 10, Panel (d)). By contrast, when the gapped divider is used, the droplets experience less shear and are able to gradually enter one channel intact.

Another factor that may be important for achieving maximum sorting speed is the minimization of the oil spacer flow rate. Proper droplet spacing is important in allowing the droplets to be interrogated and sorted individually, but too much oil increases capillary number and limits sorting speed. To minimize oil flow rate, a narrow, 50 μm-wide sorting junction with a wide electrode was used, which exerted a constant force on the droplets over a long distance. A second gapped divider was also implemented at the entrance of the sorting junction (section at the left of FIG. 10, Panels (a) and (b)), which pinned incoming droplets against the upper wall so that the full channel was used during sorting and no oil was wasted. This divider operated by diverting high flow-rate carrier oil, utilized to properly space droplets, from the reinjection channel into a lower channel carrying the bias oil used to tune lateral drop position downstream. The combined oil flow from below pinned incoming drops to the upper channel wall; without such a design, the droplets move to the center of the channel.

The gapped dividers allow for the maximization of sorting speed, but other features may be important to ensure sorting accuracy. For example, as flow rates increase to sort faster, inlet pressures grow causing the droplet filter to bow (FIG. 11, Panel (a)). Bowing widens the filter gaps permitting dust to pass that may clog the device. It also causes droplets to pack in vertical layers, leading to irregular spacing (FIG. 11, Panel (b)) and possible sorting errors. To address these issues, an alternate design was used with the filter in the same shallow layer as the gapped divider (drop inlet in FIG. 11, Panel (a)) rather than the taller layer of the rest of the sorting junction (coloured grey). The filter still bowed under the pressure, but the gaps remained small enough to remove debris. Moreover, as the droplets approached the injection channel, they were forced into a monolayered, single-file line for even spacing (FIG. 11, Panel (c)). Evidence of bowing can be seen in the open areas of the filter, where deformation around the posts appeared as non-uniform shading and where droplets stacked vertically in multiple layers (FIG. 11, Panel (d)).

Figure 11:
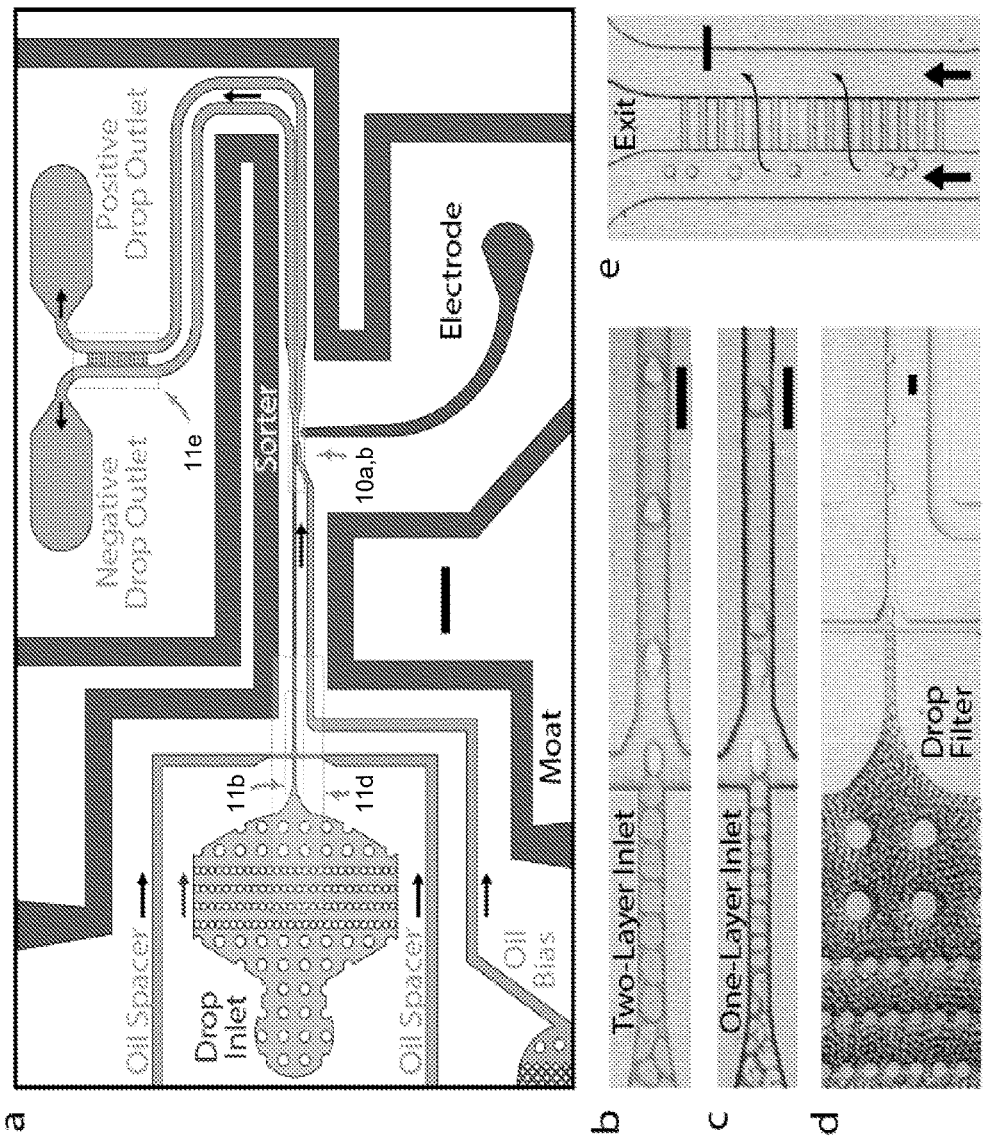
FIG. 11, Panels A-E, provide (a) a schematic of a microfluidic device according to an embodiment of the present disclosure, with shallow channels in boxed regions indicating areas magnified in other figures. Microscope images of (b) irregularly spaced, reinjected droplets from a single-layer reinjector and (c) regularly spaced droplets from the actual two-layer reinjector used to sort. (d) The droplet filter before the reinjector. (e) Equilibration channels connecting the exit outlets. Scale bars are 500 µm in (a) and 50 µm in (b-e).

After spacing, the droplets traveled to the sorter, as shown in FIG. 11, Panel (a) and expanded in FIG. 10, Panels (a) and (b). There, the droplets were scanned by a laser and their fluorescence measured. A salt water electrode (2M NaCl) connected to a high voltage amplifier applied the electric field that sorted the droplets. The moat, a grounded salt water electrode bordering the device, generated the field gradient necessary for dielectrophoretic deflection and limited stray fields that could cause unintended droplet merger in the filter. Once sorted, the divided populations traveled down two parallel channels with similar hydrodynamic resistance. Because the negatively sorted population was often much larger than the positively sorted, the negative channel experienced greater flow resistance from droplet drag. To equilibrate pressures and enable controlled dispensing into the collection reservoirs, a shallow series of parallel channels was included near the outlet (magnified in FIG. 11, Panel (e)) to allow oil, but not droplets, to move between outlets and equilibrate small pressure differentials. This also made the sorter less sensitive to small differences in the outlet tube heights, which could generate a gravitational back-pressure that could interfere with the droplet sorting.

To demonstrate the effectiveness of the fast sorter, it was used to sort a test emulsion including two droplet populations: a dim "negative" population and a bright "positive" population. The positive droplets included phosphate-buffered saline with 1.4% by volume 0.5 μm latex beads (Sigma Aldrich, L3280) to make them appear dark in the optical microscopy images (FIG. 10, Panel (b)) and 0.75% fluorescent yellow 0.03 μm latex beads (Sigma Aldrich, L5150) to make them brightly fluorescent. The negative droplets were phosphate-buffered saline with 0.13% fluorescent yellow beads, making them dimly fluorescent so that they too could be detected by the drop detector. To create sufficient emulsion for several hours of sorting at 30 kHz, the emulsions were generated using serial droplet splitting, formed initially as 50 μm droplets that were each halved three times to produce 8 droplets 25 μm in diameter. This enabled the generation of droplets at 2 mL/hr for the aqueous phase, approximately five times faster than could be achieved with a flow focusing generator.

To sort the emulsion, the droplets were injected into the device at 0.7 mL/hr, with the drop spacing oil and drop position-tuning bias oil each at 7 mL/hr. That corresponded to an average flow velocity of 3 m/s through the 30 μm×50 μm sorter cross section. The fluorinated oil (3M, HFE-7500) and 1% PEG-PFPE amphiphilic block copolymer surfactant combined for a drop interfacial tension of 4 mN/m and a nearly matched water-oil dynamic viscosity of 0.1 mPa-s, giving a very large Ca of 0.8 at that flow. The fluorescence was generated by a 473 nm laser (CNI Lasers), filtered at 517±10 nm by a bandpass filer (Semrock), and measured by a photomultiplier tube (PMT, Thorlabs, PMM02). The signal was analysed by an FPGA (NI, PCI-7833R) with custom LabVIEW software. Droplets falling within the user-defined thresholds were sorted via an amplified pulse (Trek 609E-6) from the FPGA, transmitted into the device via a salt water electrode. To visualize the sorting and capture high speed videos, the device was illuminated with infrared light that did not overlap with the droplet fluorescence and imaged with a fast camera (Phantom, Miro M310) at a 50 kHz frame rate.

Figure 12:
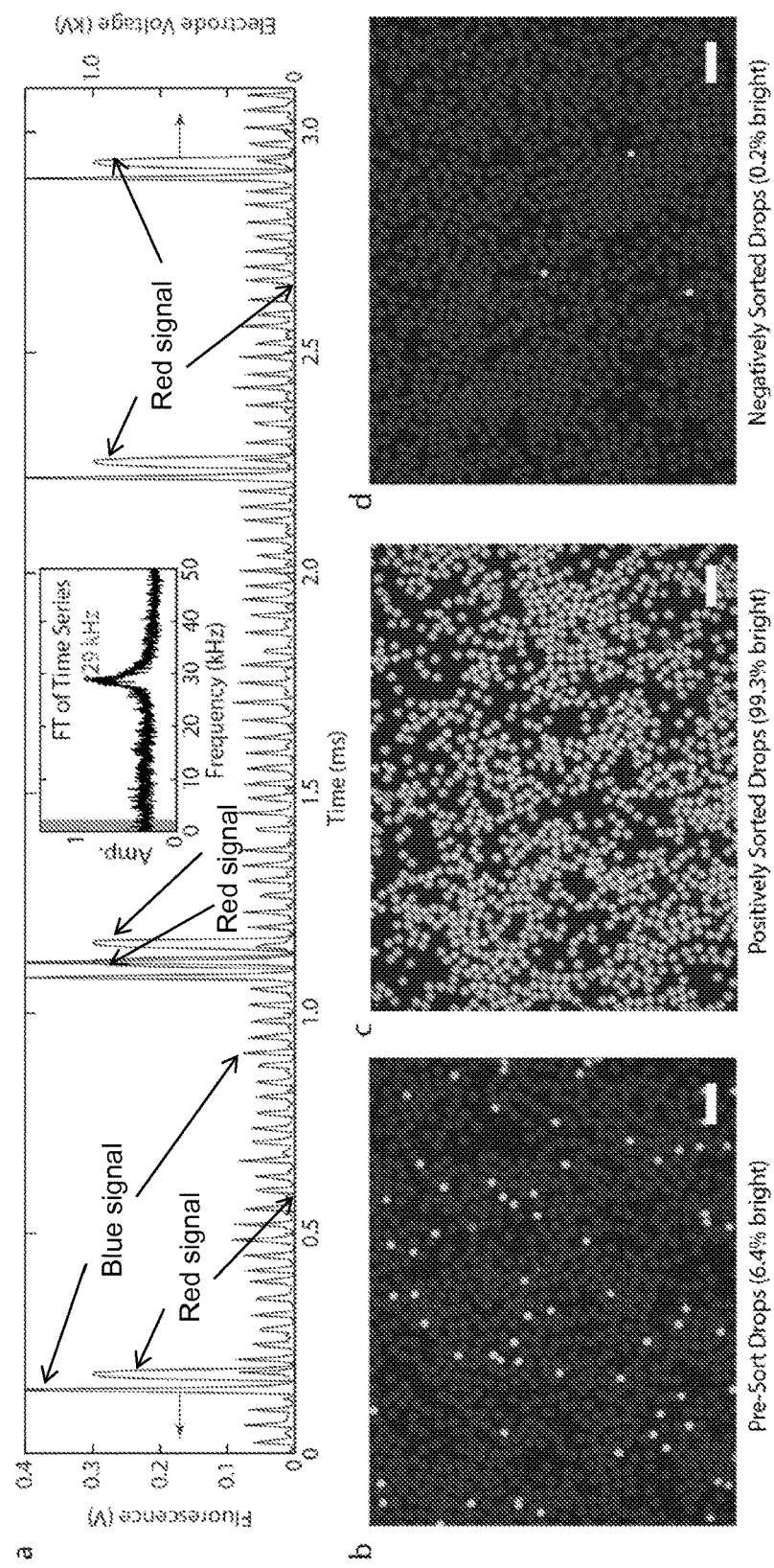
FIG. 12, Panels A-D, provide (a) Time series during a sort showing the PMT-detected fluorescence signal (blue) as well as the voltage applied to the electrode (red). Inset shows the frequency components from a Fourier transform of a longer time series during the same sort, as well as the range of previously reported sort rates. Fluorescence microscope images, also from the same sort, of the pre-sorted droplets (6.4% bright), the positive droplets (99.3% bright), and negative droplets (0.2% bright). Scale bars are 100 µm.

The fluorescence signals and pre- and post-sorted droplet populations from an hour-long, ~30 kHz sorting run (equivalent to processing over 108 drops) are shown in FIG. 12. As the droplets passed through the excitation laser, their emitted fluorescence was detected by the PMT, which outputted a voltage proportional to the intensity of the emitted light. The semi-periodic drop fluorescences, as detected by the PMT, are shown in a time series in blue in FIG. 12, Panel (a), with the corresponding sorting pulses in red. The PMT had a bandwidth of 0-20 kHz, such that frequency components above this range were attenuated by a factor proportional to their fold-increase over 20 kHz. PMTs with higher frequency response are commercially available and can be implemented to detect droplets more quickly. The PMT voltages were recorded at 200 kHz, a sampling period of 5 μs, which was approximately the time a droplet spends in the detector region. The individual droplet signals, despite being broadened in time and attenuated in amplitude by the limited PMT bandwidth, were nevertheless still well above the noise floor and distinguishable as shown in the time trace.

Positive droplets were identified as those whose fluorescence was above a PMT threshold of 0.15 V and whose temporal width at the threshold was <50 μs, which excluded large, merged droplets. When a positive droplet was detected, the computer outputted a 1 V, 33 μs rectangular pulse amplified with edge rounding to 1 kV by the 13 kHz-bandwidth, high voltage amplifier. The detection laser was positioned ahead of the electrode so that, after identifying a droplet, an immediately-applied pulse corresponded to the moment the droplet was directly opposite the electrode, which was optimal for sorting. To estimate sorting speed, the droplet rate in the time series of an hour long run was measured by identifying peaks and, additionally, by measuring the maximum of the Fourier transform, which was centred on 29±1 kHz (FIG. 12, Panel (a), inset). The sorting rates of conventional microfluidic devices are tenfold less than this and, for comparison, fall within the red band in the left of the inset.

To confirm accurate droplet sorting, the pre- (FIG. 12, Panel (b)), positive- (FIG. 12, Panel (c)), and negative-sort (FIG. 12, Panel (d)) droplet populations were imaged with fluorescence microscopy. The pre-sort population was 6.4% bright, in agreement with the fraction of positives detected with the PMT time traces. The positive population was 99.3% and the negative 0.2% bright. The false positives (dim droplets in the positive population) were abnormally large (most were >3 times the mean droplet volume, FIG. 12, Panel (c)) and were likely merged drops that were too large for the device design. The false negatives (bright droplets in negative population) were abnormally small (<2 times the mean droplet volume), which likely led to a proportionally smaller dielectrophoretic force and inadequate deflection during sorting. In most cases, sorting errors thus resulted from polydispersity in the starting emulsion, suggesting that higher accuracy requires more uniform emulsions. This is difficult to achieve because most emulsions, no matter the care taken to generate and handle them, will contain rare instances of droplets that merged or split and are thus abnormally large or small. Filtration of the emulsion prior to sorting may improve this, but requires additional steps that can result in even more merger and splitting.

The described device achieved sorting rates that rival those of fluorescence-activated cell sorters, which can sort at tens of kilohertz. Recently, small microfluidic droplets (10-20 μm) have been sorted at 10-15 kHz using these FACS methods. However, this required a double emulsification step in which the water-in-oil droplets were suspended as water-in-oil-in-water double emulsions in an aqueous carrier compatible with FACS. This may not be appropriate for all applications since double emulsions are generally less stable than single emulsions and, in addition, tend to be more permeable to small molecules, which can leach out of the droplets over time. In instances in which these issues are important, fast microfluidic droplet sorting is valuable.

As discussed herein, the present disclosure provides a microfluidic device that accurately sorts droplets at 30 kHz, ten times faster than existing droplet sorters. Pushing the rate higher is possible but may require faster electronics. The speed of the described droplet sorter will allow sorting of emulsions with unprecedented numbers of droplets. This will be valuable for applications in protein engineering and cell biology, in which the target droplets or cells are extremely rare in the population. Such enrichment is important, for example, for enhancing enzymes through droplet-based microfluidic directed evolution or for isolating very rare circulating tumor cells from blood cells.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of delivering discrete entities to a substrate, the method comprising:
   flowing a plurality of discrete entities through a microfluidic device in a carrier fluid, wherein the discrete entities are insoluble and/or immiscible in the carrier fluid, and wherein the microfluidic device comprises a sorter comprising a flow channel comprising a gapped divider comprising a separating wall which extends less than the complete height of the flow channel;
   sorting, via the sorter, one or more of the plurality of discrete entities to be delivered through a delivery orifice to the substrate from the plurality of discrete entities;
   directing the carrier fluid and the one or more of the plurality of discrete entities through the delivery orifice to the substrate; and
   affixing the one or more of the plurality of discrete entities to the substrate.

2. The method of claim 1, wherein the one or more of the plurality of discrete entities are affixed to the substrate via a force, wherein the force is selected from a gravitational force, an electrical force, a magnetic force, and combinations thereof.

3. The method of claim 2, comprising storing the affixed entity under controlled environmental conditions for a storage period, wherein the force is maintained during the storage period.

4. The method of claim 3, wherein the controlled environmental conditions comprise a constant temperature and/or pressure.

5. The method of claim 2, wherein the force is an electrical force.

6. The method of claim 5, wherein the electrical force is a dielectrophoretic force.

7. The method of claim 1, wherein the discrete entities are droplets.

8. The method of claim 7, wherein the droplets are affixed to the substrate via wetting and/or interfacial tension.

9. The method of claim 7, wherein the droplets comprise an aqueous fluid, which is immiscible with the carrier fluid.

10. The method of claim 9, wherein the substrate comprises on a first surface a layer of fluid which is miscible with the carrier fluid and immiscible with the aqueous fluid, and wherein the droplets are affixed to the first surface of the substrate following introduction into the layer of fluid on the first surface of the substrate.

11. The method of claim 1, wherein the discrete entities have a dimension of from about 1 to 1000 μm.

12. The method of claim 11, wherein the discrete entities have a diameter of from about 1 to 1000 μm.

13. The method of claim 1, wherein the discrete entities have a volume of from about 1 femtoliter to about 1000 nanoliters.

14. The method of claim 1, wherein the plurality of discrete entities is optically scanned prior to the sorting.

15. The method of claim 14, wherein the sorting is based on results obtained from the optical scan.

16. The method of claim 1, wherein the sorter is an active sorter.

17. The method of claim 16, wherein the sorting comprises sorting via dielectrophoresis.

18. The method of claim 1, wherein the plurality of discrete entities comprises discrete entities which differ in composition.

19. The method of claim 1, wherein the microfluidic device is integrated with an automated system which either:
   selectively positions the delivery orifice relative to the substrate, and wherein the method comprises selectively positioning via the automated system the delivery orifice relative to the substrate to selectively deliver the one or more of the plurality of discrete entities to one or more locations on or in proximity to the substrate; or
   selectively positions the substrate relative to the delivery orifice, and wherein the method comprises selectively positioning via the automated system the substrate relative to the delivery orifice to selectively deliver the one or more of the plurality of discrete entities to one or more locations on or in proximity to the substrate.

20. The method of claim 19, wherein the method comprises delivering a first member of the plurality of discrete entities to a first location on or in proximity to the substrate and a second member of the plurality of discrete entities to a second location on or in proximity to the substrate.

21. The method of claim 20, wherein the first and second locations are the same.

22. The method of claim 1, wherein one or more biological assays are performed in one or more of the discrete entities before and/or after delivery to the substrate.

23. The method of claim 1, wherein one or more of the plurality of discrete entities comprises a cell.

24. The method of claim 1, wherein one or more of the plurality of discrete entities comprises a nucleic acid.

25. The method of claim 1, wherein the method comprises encapsulating or incorporating one or more reagents into the plurality of discrete entities.

26. The method of claim 25, wherein the one or more reagents comprise amplification reagents.

27. The method of claim 26, wherein the amplification reagents comprise Polymerase Chain Reaction (PCR) reagents.

* * * * *